United States Patent
Kernodle et al.

(10) Patent No.: US 8,481,056 B2
(45) Date of Patent: *Jul. 9, 2013

(54) PRO-APOPTOTIC BACTERIAL VACCINES TO ENHANCE CELLULAR IMMUNE RESPONSES

(75) Inventors: Douglas S. Kernodle, Brentwood, TN (US); Markian R. Bochan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,325

(22) Filed: Sep. 19, 2011

(65) Prior Publication Data

US 2012/0276144 A1    Nov. 1, 2012

Related U.S. Application Data

(63) Continuation of application No. 10/467,644, filed as application No. PCT/US02/03451 on Feb. 7, 2002, now Pat. No. 8,021,671.

(60) Provisional application No. 60/267,328, filed on Feb. 7, 2001, provisional application No. 60/322,989, filed on Sep. 18, 2001.

(51) Int. Cl.
*A61K 39/04* (2006.01)
*A61K 49/00* (2006.01)
*A01N 63/00* (2006.01)

(52) U.S. Cl.
USPC ......... 424/248.1; 424/9.1; 424/9.2; 424/93.1; 424/93.2; 424/184.1; 424/185.1; 424/234.1; 435/183; 435/185; 435/243; 435/252.1; 435/253.1; 435/440; 435/441; 435/471; 435/472

(58) Field of Classification Search
USPC ........... 424/9.1, 9.2, 93.1, 93.2, 184.1, 185.1, 424/234.1, 248.1; 435/183, 185, 243, 252.1, 435/440, 253.1, 441, 471, 472
See application file for complete search history.

(56) References Cited

U.S. PATENT DOCUMENTS 6,221,900 B1 * 4/2001 Uckun et al. .................. 514/457
8,021,671 B2 * 9/2011 Kernodle et al. .......... 424/248.1

* cited by examiner

*Primary Examiner* — Rodney P. Swartz
(74) *Attorney, Agent, or Firm* — Ballard Spahr LLP

(57) ABSTRACT

Whole-cell vaccines and methods for their use in producing protective immune responses in vertebrate hosts subsequently exposed to pathogenic bacteria. The present invention involves a method of enhancing antigen presentation by intracellular bacteria in a manner that improves vaccine efficacy. After identifying an enzyme that has an anti-apoptotic effect upon host cells infected by an intracellular microbe, the activity of the enzyme is reduced, thereby modifying the microbe so that it increases immunogenicity. Also, the present invention provides a method of incrementally modifying enzyme activity to produce incrementally attenuated mutants of the microbe from which an effective vaccine candidate can be selected.

16 Claims, 25 Drawing Sheets

Figure 9.

BVV-infected lungs

BCG-infected lungs (A) BVV, Anti-CD8, HRP x 20

(B) BCG, Anti-CD8, HRP x 20

PRO-APOPTOTIC BACTERIAL VACCINES TO ENHANCE CELLULAR IMMUNE RESPONSES

This application is a continuation of and claims priority to U.S. application Ser. No. 10/467,644, now U.S. Pat. No. 8,021,671, filed on Apr. 13, 2007, which is a 35 U.S.C. 371 National Stage Application of International Application No. PCT/US02/03451, filed Feb. 7, 2002, which claims the benefit of U.S. Provisional Application No. 60/322,989, filed on Sep. 18, 2001 and U.S. Provisional Application No. 60/267,328, filed on Feb. 7, 2001 all of which are hereby incorporated herein by reference in their entirety.

This invention was made with government support under NIH Grant AI 35250, NIH Grant A137871, and a Merit Review Award from the Department of Veterans Affairs. The U.S. Government may have certain rights in this invention.

BACKGROUND OF THE INVENTION

1. Field of the Invention

The present invention relates to the field of vaccine production and preventing or treating infectious diseases. Specifically, the present invention relates to methods for producing a safe and effective vaccine and methods for enhancing an effective immune response in a host animals subsequently exposed to infection by bacterial pathogens, for example, *Mycobacterium tuberculosis*.

2. Background Art

Although recombinant DNA technology promises the ability to make a new generation of rationally designed live-attenuated vaccines, there are critical problems that have limited the usefulness of traditional allelic inactivation techniques in fulfilling this promise.

A major problem common to all vaccine development including those created by using recombinant DNA technology has been the difficulty in inducing responses in specific populations of immune cells capable of rendering long-lived protection. Vaccination prepares an animal to respond to antigens of pathogenic microbes. Vaccination is more complex than immune recognition in that only some types of immune responses will be correlated with protective immunity and the responses that are important vary with different pathogens. For example, antibody responses are critical in conferring protective immunity against polio but have minimal importance in immune protection against tuberculosis.

With many pathogens a cellular immune response is more important than an antibody response. Cellular immune responses are primarily mediated by CD4+ T-lymphocytes, which secrete interferon-gamma and activate macrophages to kill intracellular microbes, and by CD8+ T-lymphocytes, which induce cytotoxic responses via death receptors (e.g., Fas, TNF-alpha receptor) or granular enzymes (i.e., perforin/granzyme), in addition to secreting interferon-gamma.

CD4+ lymphocytes and CD8+ lymphocytes are primed for an immune response using different antigen presentation pathways. With CD4+ T-cells, exogenous foreign antigens are taken up or recovered from ingested microbes within the phagosome of antigen presenting cells, degraded into fragments, and bound on the surface of these cells to MHC Class II molecules for presentation to the CD4+ T-cells. MHC Class II molecules are restricted primarily to some few types of lymphoid cells. CD8+ T-cell activation is achieved via a different mechanism that involves MHC Class I molecules, which are found on essentially all nucleated cells. Proteins produced or introduced within the nucleated cell are degraded to peptides and presented on the cell surface in the context of MHC Class I molecules to CD8+ T-cells. MHC Class I antigen presentation is generally referred to as the "endogenous antigen" pathway to differentiate it from the "exogenous antigen" pathway for presenting antigens via MHC Class II receptors to CD4+ T-lymphocytes.

Dendritic cells are specialized lymphoid cells that are especially efficient in presenting antigens. They have the capability of internalizing apoptotic macrophages or their fragments and presenting antigens from within the apoptotic macrophage via both MHC Class I and MHC Class II pathways (Albert, Sauter, and Bhardwaj, 1998; Yrlid and Wick, 2000; Wick and Ljunggren, 1999).

With many infectious diseases CD8+ T-cells appear to be the major determinant of prolonged immunity against re-infection that does not depend upon persistent antigenic stimulation (Lau et al., 1994). This has made the generation of strong CD8+ responses a critical factor for new vaccines. Some strategies such as DNA vaccination (Feigner et al., U.S. Pat. No. 5,589,466) appear to produce relatively good CD8+ responses compared to other methods of vaccination. However, a significant limitation of DNA vaccination is that antigens are derived from only a single gene or only a small portion of a bacterial genome corresponding to a minority of the microbe's immunodominant CD8+ epitopes. A method for delivering a larger repertoire of microbial antigens to dendritic cells would be useful, including techniques for directing whole-cell live-attenuated vaccines to associate with dendritic cells so that all microbial antigens could be processed.

Aside from the general problem common to all vaccines of inducing the appropriate type of protective immune responses for a specific pathogen, there are also specific problems with using allelic inactivation to construct new live-attenuated vaccines. One is that many microbial genes are essential for survival, including some of the best potential targets for attenuating a virulent microbe to produce a new vaccine candidate. Therefore, a mutant wherein the activity of a gene that is essential for in vitro growth has been inactivated cannot be cultivated in vitro. This problem can be partially overcome if exogenous substances are added to bypass the function of the essential gene, for example, supplementing in vitro culture media with amino acids or hypoxanthine to permit the identification and recovery of allelic knockout mutants in which essential genes for amino acid biosynthesis or purine biosynthesis, respectively, have been inactivated. Another strategy to overcome this limitation has been "in vivo expression technology" and other techniques for identifying differentially expressed genes (Slauch, Mahan, and Mekalanos, 1994). These techniques attempt to identify genes that are essential for the in vivo survival of a microbe but which are not essential for their in vitro cultivation. Therefore, it is anticipated that inactivating the "in vivo"-expressed gene will yield a candidate that can be cultivated in vitro but is attenuated in vivo.

However, although the exogenous supplementation of auxotrophs and the identification of genes that are essential only for in vivo microbial survival has expanded the number of genes that can be inactivated to generate new live-attenuated vaccine candidates, a large number of genes remain that are essential both for in vitro and in vivo microbial survival, and which are not amenable to exogenous supplementation to enable their in vitro survival and cultivation. Therefore, having a method that enables a partial rather than complete reduction in the gene product will permit a larger number of such essential genes to be altered for producing new live-attenuated vaccine candidates. Ideally, this method would enable the production of stable mutants with minimal potential to revert back to the virulent phenotype.

A second major problem with current attempts to create new vaccines using recombinant DNA technology has been the difficulty in finding the right balance between attenuation and immunogenicity. In most circumstances when a mutant is identified or created, it is either still too virulent to be used as a vaccine or is cleared too rapidly by the host to engender protective immunity. For example, new auxotrophic tuberculosis vaccine candidates exemplify this problem all too well. If the strain can scavenge too much of the essential nutrient in vivo, it may be able to assume the virulent phenotype. Consider that methionine-auxotrophic mutants of Bacillus Calmette-Guerin (BCG), a vaccine strain for tuberculosis that is given to more than 100 million people annually worldwide, grow as well in vivo as the parent BCG strain (McAdam et al., 1995). This suggests that the auxotroph is able to scavenge enough methionine in vivo to meet its growth needs, thereby bypassing the metabolic defect that made it auxotrophic in vitro. This makes it likely that a methionine-auxotrophic mutant of virulent M. tuberculosis would still be virulent in vivo. In contrast, if growth is restricted too severely the auxotroph might not persist long enough or make enough of the immunodominant antigens needed to drive a protective immune response. This has been observed with a lysine auxotroph, which when given as a single-dose immunization had no efficacy, but conferred some protective immunity when given as a 3-dose regimen (Collins et al., 2000). The leucine and purine auxotrophs have shown some vaccine efficacy but appear less protective than immunization with BCG (Hondalus et al., 2000; Jackson et al., 1999).

A further problem with current allelic inactivation strategies for vaccine development is the inability to subsequently modify a promising vaccine candidate. When allelic inactivation creates a mutant that is too attenuated, then it is not possible using allelic inactivation techniques for the mutant to be further adjusted to achieve the right balance between attenuation and immunogenicity. When allelic inactivation creates a mutant that is not sufficiently attenuated, then allelic inactivation can be applied to a second microbial gene in an effort to further attenuate the mutant, but there still remains a difficulty in obtaining the optimal level of attenuation for vaccine efficacy. Therefore, allelic inactivation is an unpredictable tool for fine-tuning the level of attenuation. However, achieving the right balance between attenuation and immunogenicity is recognized as being critical to the development of a new live-attenuated tuberculosis vaccine, and strategies that enable incremental adjustments of vaccine candidates are needed.

Historically one of mankind's most important infections, tuberculosis remains a major public health problem and cause of human illness. Morbidity and mortality remain high with predictions of 225 million new cases and 79 million deaths from tuberculosis between 1998 and 2030 (Murray and Salomon, 1998). This is despite the availability of effective treatment regimens and the widespread use of a live attenuated strain of Mycobacterium bovis, Bacillus Calmette-Guérin (BCG), as a vaccine. Furthermore, there is an enormous reservoir of persons latently infected with Mycobacterium tuberculosis estimated to comprise approximately one-third of the world's population (Snider, Jr. and La Montagne, 1994).

Previous investigations have shown that BCG does not induce very strong CD8+ responses (Kaufmann, 2000). However, MHC Class I pathways and CD8+ T-cells are important in the normal host containment of virulent M. tuberculosis, as mice with defects in MHC Class I antigen presentation succumb rapidly to tuberculosis (Flynn et al., 1992;Sousa et al., 2000). MHC Class I pathways and CD8+ T-cells may be particularly important in preventing latent tuberculosis infection from developing into active disease, as exposed healthy household contacts of TB cases and individuals with inactive self-healed TB exhibit vigorous CD8+ responses (Lalvani et al., 1998) (Pathan et al., 2000). CD8+ cells appear to exert their protective effect against tuberculosis in several ways including cytotoxic T-lymphocyte (CTL) activity resulting in lysis of host macrophages infected with M. tuberculosis, by killing intracellular bacilli via the release of the antimicrobial peptide granulysin, and by IFN-gamma production (Cho et al., 2000; Serbina and Flynn, 1999; Silva et al., 1999; Serbina et al., 2000). As classic concepts regarding host control of tuberculosis have emphasized the processing of antigens from M. tuberculosis within phagosomes via MHC Class II pathways to CD4+ T-cells, it has been unclear why MHC Class I-CD8+ pathways should be so critical.

Devising strategies to induce greater CD8+ responses than BCG is a major focus of tuberculosis vaccine research (Cho, Mehra, Thoma-Uszynski, Stenger, Serbina, Mazzaccaro, Flynn, Barnes, Southwood, Celis, Bloom, Modlin, and Sette, 2000; Kaufmann, 2000). Such appears to be possible via DNA vaccination, which results in greater populations of CD8+/CD44$^{hi}$ T-cells that produce IFN-gamma than is achieved with BCG vaccination (Silva, Bonato, Lima, Faccioli, and Leao, 1999). However the T-cell responses are restricted to the antigen or antigens produced by the specific gene or genes expressed by the DNA vaccine. Others have tried to improve CD8+ responses by cloning listeriolysin into BCG in hopes that its pore-forming properties would enable M. tuberculosis antigens within the phagosome to gain access to the cytosol of the macrophage and be processed via MHC Class I pathways (Hess et al., 1998).

Because of the inability of the BCG vaccine to adequately prevent pulmonary infection by M. tuberculosis, there exists a need to improve antigen presentation to the immune cells most strongly correlated with long-term protective immunity, particularly CD8+ T-lymphocytes. The present invention provides a solution to this problem by providing a method of vaccine development, wherein the pathogen is engineered so that antigen presentation is enhanced.

There also exists a great need for developing a vaccine that is derived from a bacterium that retains sufficient immunogenicity and can be modified to attenuate its pathogenicity. Accordingly, there exists a need for a method of vaccine development that provides the right balance between attenuation and immunogenicity. The present invention provides the solution to this problem by providing a method of vaccine development, wherein the pathogen is engineered so that an enzyme essential for the full expression of survival in vivo is produced at reduced levels or is a less-efficient form of the enzyme, yet the live-attenuated microbe is sufficiently immunogenic.

The invention specifically solves the problems with M. tuberculosis vaccines by providing an effective vaccine against tuberculosis.

SUMMARY OF THE INVENTION

The present invention involves a method of enhancing antigen presentation by intracellular bacteria in a manner that improves vaccine efficacy. When an enzyme of an intracellular bacterium is reduced that normally inhibits apoptosis of the host cell, a pro-apoptotic effect is rendered upon the host cell. This has the advantage of diminishing intracellular survival of the microbe, thereby contributing to the in vivo attenuation of the vaccine strain. It also increases antigen processing by dendritic cells, including increasing MHC Class I antigen presentation to CD8+ T-lymphocytes, substantially altering the manner of antigen presentation so as to enhance vaccine efficacy. Another aspect of the invention deals with circumstances in which the anti-apoptotic microbial factor is essential for viability of the bacterium. To solve this problem, a method is described for incrementally attenuating virulent strains or partially-attenuated strains of bacteria by replacing a gene encoding an essential bacterial enzyme with a mutant form of the gene or analogous gene from another species, thereby resulting in diminished enzymatic activity, thereby producing mutant bacteria with diminished disease-causing potential yet capable of inducing a protective immune response. This method can also be applied to bacterial factors that do not have an anti-apoptotic function to create attenuated strains.

Also, as the induction of strong CD8+ T-cell responses has generally been difficult to achieve with current vaccination strategies, the present modified microbes provide a surprisingly effective way to access this arm of the immune system. The microbe can be further altered by adding exogenous DNA encoding immunodominant antigens from other pathogenic microbes including viruses, bacteria, protozoa, and fungi or with DNA encoding cancer antigens, and then used to vaccinate a host animal. Therefore, the present attenuated bacterium can be used as a vaccine delivery vehicle to present antigens for processing by MHC Class I and MHC Class II pathways. And because of strong co-stimulatory signals induced by microbial antigens in the vaccine vector, this directs the host immune system to react against the exogenous antigen rather than develop immune tolerance.

The invention also describes a method for creating mutants of microbes when the anti-apoptotic factor is an essential microbial enzyme such that allelic inactivation would not permit in vitro cultivation of the microbe, or the mutant would be cleared too rapidly in vivo to be sufficiently immunogenic. When enzyme activity is diminished by replacing the wild-type gene encoding the enzyme with mutant alleles encoding incrementally less efficient forms of the enzyme, then incrementally attenuated mutant bacterial strains are produced which facilitate the identification of one or more mutant strains that is not sufficiently pathogenic to cause disease but persists long enough in vivo to induce a protective immune response in the host. Incremental attenuation can be applied to any microbial species. It can be applied to any essential microbial enzyme, including enzymes that do not exert an anti-apoptotic effect upon the host cell. However, when the activities of certain anti-apoptotic enzymes of intracellular bacteria are reduced, antigen presentation can be enhanced, by mechanisms discussed above.

The present strategy of making mutants with incremental reductions in their capacity to survive in vivo and selecting the mutant that possesses the requisite immunogenicity and attenuation has clear advantages over the hit-and-miss strategy exemplified by current allelic inactivation techniques. One advantage is the time savings and increased efficiency achieved by making multiple vaccine candidates with defects in a single enzyme as opposed to targeting multiple genes but producing only a single mutant in each. Furthermore, there is the advantage of being able to fine-tune the vaccine. For example, if the mutant exhibiting 20% of wild-type enzyme activity is too virulent and the mutant exhibiting 10% of activity is too attenuated and does not survive long enough in vivo to be immunogenic, then the strain can be modified to an intermediate activity (e.g., 15%), which yields a better vaccine.

A further advantage is the ability to tailor the vaccine to match heterogeneity in host immunity among potential vaccinees, by producing a group of mutants with incremental attenuation. For example, persons with HIV/AIDS could receive a more attenuated mutant than the strain that achieves the right balance of attenuation and immunogenicity in persons with normal immunity. This approach now enables a single-dose vaccine for the vast majority of recipients, because the ability to generate incremental attenuation alleviates the need for the vaccine to be attenuated to the level needed for the most immunosuppressed persons likely to receive it. Rather, a more attenuated version of the vaccine can easily be made for an immunosuppressed population. The invention, thus, enables the level of attenuation in vaccines to be refined and tailored to match the immune system of vaccinees.

Another advantage to this invention is realized when the essential enzyme to be mutagenized is one that detoxifies anti-microbial substances made by the host immune system. Although auxotrophy is a popular way for constructing novel vaccine candidates, there are potential problems involving gene induction in auxotrophs that might lessen their potential as useful vaccines. For example, starvation and nutrient limitation are potent stimuli for specialized gene induction in bacteria. Accordingly, even if the duration of in vivo growth of an auxotroph can be optimized such that the quantity of antigen presented to the host is not a problem, in vivo nutrient limitation can force the bacteria to produce primarily the microbial factors that help it adapt to the stress of deprivation, at the expense of producing key antigens. As a result, the types of antigen available to the immune system are not the factors needed to induce a protective immune response. In contrast, the present method can attenuate the vaccine strain by making it more susceptible to host defenses, and when used with certain enzymes, does not create a situation where starvation gene induction can have a substantial impact. In the present vaccines, the stresses the microbe encounters are an exaggeration of what it normally encounters during infection, rather than a qualitatively different type of stress.

Thus, the present invention provides a method of modifying a microbe, whereby the microbe increases immunogenicity in a subject, comprising reducing the activity of an anti-apoptotic enzyme produced by the microbe, whereby reducing the activity of the enzyme attenuates the microbe and enhances its antigen presentation.

The present invention also provides a method of attenuating a microbe, whereby the microbe retains or increases immunogenicity but has reduced pathogenicity in a subject, comprising reducing the activity of an essential enzyme produced by the microbe, whereby reducing the activity of the enzyme attenuates the microbe.

The present invention also provides a microbe attenuated according to a method whereby the microbe retains or increases immunogenicity but has reduced pathogenicity in a subject, comprising reducing the activity of an essential enzyme produced by the microbe.

The present invention also provides a microbe modified according to a method whereby the microbe increases immunogenicity but has reduced pathogenicity in a subject, comprising reducing the activity of an anti-apoptotic enzyme produced by the microbe.

The present invention further provides a composition comprising a microbe attenuated according to the methods of the present invention and a pharmaceutically acceptable carrier.

Moreover, the present invention provides a method of producing an immune response by an immune cell of a subject, comprising contacting the cell with a composition of the present invention.

The present invention also provides a method of producing an immune response in a subject, comprising administering to the subject an effective amount of a composition of the present invention.

Also, the present invention provides a method of preventing or diminishing the severity of an infectious disease in a subject, comprising administering to the subject an effective amount of a composition of the present invention.

BRIEF DESCRIPTION OF THE DRAWINGS

FIG. 3. Expression of antisense sodA mRNA. Northern hybridization of RNA from isolates of *M. smegmatis* $mc^2155$ transformed with plasmid vectors. Lane 1, *M. smegmatis* $mc^2155$; Lane 2, *M. smegmatis* $mc^2155$ transformed with pHV202-AS-SOD; Lane 3, *M. smegmatis* $mc^2155$ transformed with pLUC10-AS-SOD. Because of strong homology between sodA of *M. tuberculosis* and sodA of *M. smegmatis*, probes were made against DNA immediately downstream of the antisense *M. tuberculosis* sodA fragment in the two vectors. A 300-bp fragment of AT-rich *S. aureus* blaZ DNA was placed into pHV202-AS-SOD in the multicloning site downstream of the antisense-sodA insert for use as a probe target. In pLUC10-AS-SOD, a portion of the luciferase gene was used as the target. Northern hybridization was performed using probes for: (A) the kanamycin-resistance gene, aph, contained on both plasmid vectors; (B) a fragment of blaZ, present in pHV202-AS-SOD; and (C) the firefly luciferase gene, present in pLUC10-AS-SOD. Only low-levels of blaZ RNA were detected in the pHV202-AS-SOD transformant suggesting poor transcription of the antisense sodA fragment, and DNA sequencing detected a 4-base alteration in the −10 ribosome binding region of Pr-HSP of pHV202-AS-SOD. Although Pr-HSP in pHV202 was subsequently repaired to produce pHV203, the earlier verification of strong antisense *M. tuberculosis* sodA transcription in pLUC10-AS-SOD led us to preferentially use the pLUC10-AS-SOD construct in initial in vitro and in vivo evaluations. The revised pHV202 SOD-diminished strains [H37Rv (pHV203-AS-SOD) and BCG (pHV203-AS-SOD)] were subsequently evaluated as described below.

FIG. 4. Western hybridization of iron-cofactored superoxide dismutase (SOD) produced by *M. tuberculosis* strain H37Rv and derivatives. Lane 1, H37Rv; Lane 2, H37Rv (pLUC10); Lane 3, H37Rv(pLUC10-AS-SOD), Lane 4, recombinant *M. tuberculosis* SOD produced in *E. coli*. Samples consisting of lysed bacterial cells were adjusted to have the same total protein concentration before PAGE. Membranes were hybridized with a 1:24,000 dilution of polyclonal antisera against H37Rv whole cell lysate (E-293 antisera) obtained from Colorado State University under NIH, NIAID Contract N01 AI-75320 (Tuberculosis Research Materials and Vaccine Testing). An arrow designates the SOD band, as determined by stripping the membrane and restaining using polyclonal antisera against recombinant SOD. Recombinant SOD was purified by chromatography on a nickel-affinity column. The recombinant SOD is 3 kDa larger than SOD produced by *M. tuberculosis* because of the histidine tag fusion. H37Rv(pLUC10-AS-SOD) produced only 13% of the amount of SOD produced by control strains.

FIG. 5. Killing of SOD-diminished H37Rv by hydrogen peroxide. Inocula of approximately $2\times10^6$ cfu of H37Rv (pLUC10) (white bars) and H37Rv(pLUC10-AS-SOD) (gray bars) were incubated in PBS alone or PBS containing two concentrations of hydrogen peroxide ($H_2O_2$) for 6 hours and plated on 7H10 agar. The number of surviving bacilli (mean values from triplicate determinations) are displayed. The antisense-SOD mutant was much more susceptible than the control strain to killing by hydrogen peroxide, exhibiting about a two log-fold greater reduction in viability to both concentrations.

FIG. 6. In vivo survival of H37Rv and its transformants in a C57BL/6 mouse model. Dark symbols represent the parent and control strains; white symbols represent strains in which the activity of an enzyme has been diminished by using antisense techniques as described above. Inocula were adjusted spectrophotometrically to a standard absorbance value and administered intravenously via the lateral tail vein. Back-counts of the initial inocula are shown as Day 0 counts, with the values of the AS-SOD strains believed to be artificially low due to greater clumping of these inocula related to a longer period of growth in glycerol-containing media such that the AS-SOD bacilli were not as well dispersed as single organisms as the control strains and other mutant strains. Day 1, 7, 14, and 28 values represent colony-forming units enumerated from homogenized organs. Each data point represents a mean value±std. error from six mice. Five of the six mice in the final H37Rv(pLUC10) group had expired before 28 days, so the final data point is omitted for this group. Of note, between the time of inoculation and harvesting of the initial groups on Day 1, greater reductions in viable bacilli were seen for the AS-SOD strains than the control strains. The AS-ClpC Atpase and AS-TRX strains demonstrated intermediate reductions in viability in the first 24 hours. After this early decrease, in general some growth of the AS-SOD, AS-ClpC Atpase, and AS-TRX strains was observed in vivo up to day 14. The murine cellular immune response to *M. tuberculosis* generally manifests during the $3^{rd}$ week following infection, and probably accounts for the clear decrease in the number of AS-SOD bacilli at day 28 compared to day 14. Similarly, the number of AS-ClpC Atpase and AS-TRX bacilli either diminished modestly or stabilized between day 14 and day 28, and mice infected with these strains appeared healthy, having gained 5 gm since day 0. The control mice were either dead or very ill in appearance by day 28.

Figure 7:
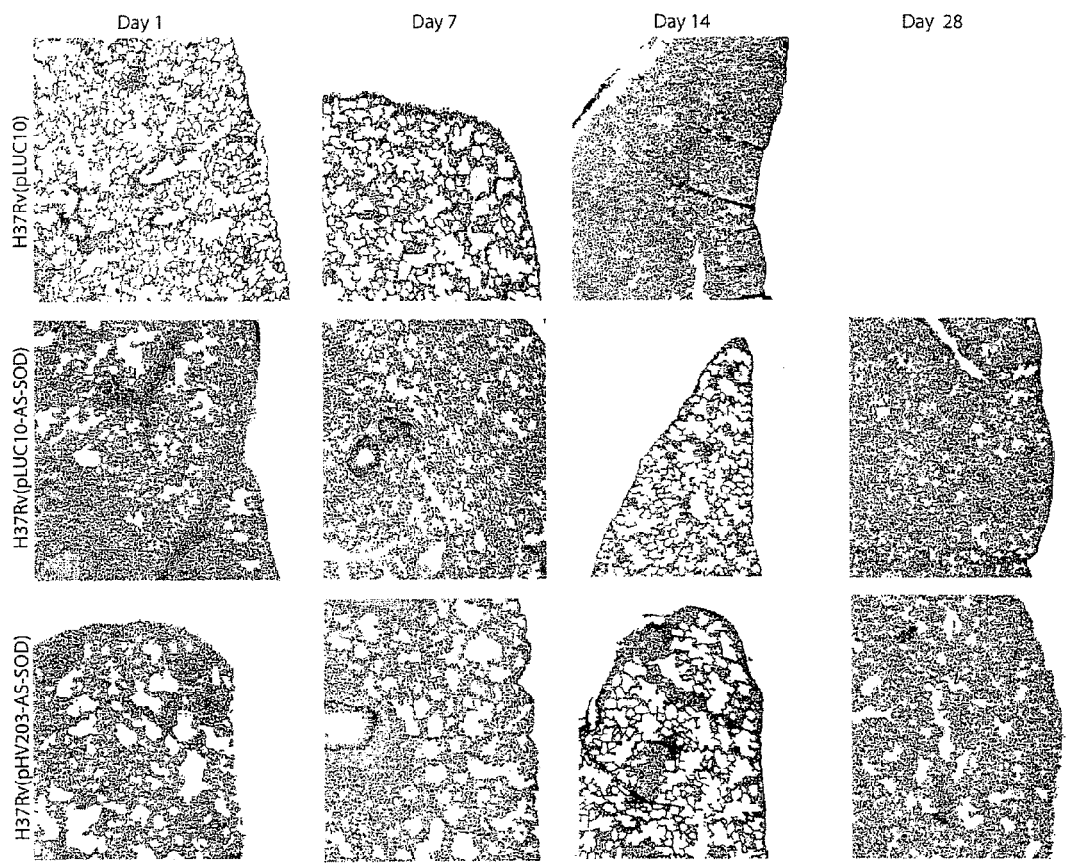

FIG. 7. Infiltration of inflammatory cells over time in mouse lungs infected with two SOD-diminished strains, H37Rv(pLUC10-AS-SOD) and H37Rv(pHV203-AS-SOD), compared to a virulent control strain, H37Rv(pLUC10). Representative H&E-stained sections at day 1, day 7, day 14, and day 28 were photographed using the 10× objective of an Olympus BX40 microscope with DP10 Microscope Digital Camera System. Mice infected with H37Rv(pLUC10) did not survive to day 28. The panels show marked early interstitial mononuclear cell infiltration of the lung of mice infected with the SOD-diminished strains, which improved by day 14 but had increased again by day 28, probably due to the development of acquired immune responses during the $3^{rd}$ and $4^{th}$ weeks following infection. In contrast, the virulent strain caused relatively less early cellular response at day 1, but by day 14 there was marked alveolar and interstitial infiltration.

Figure 8:
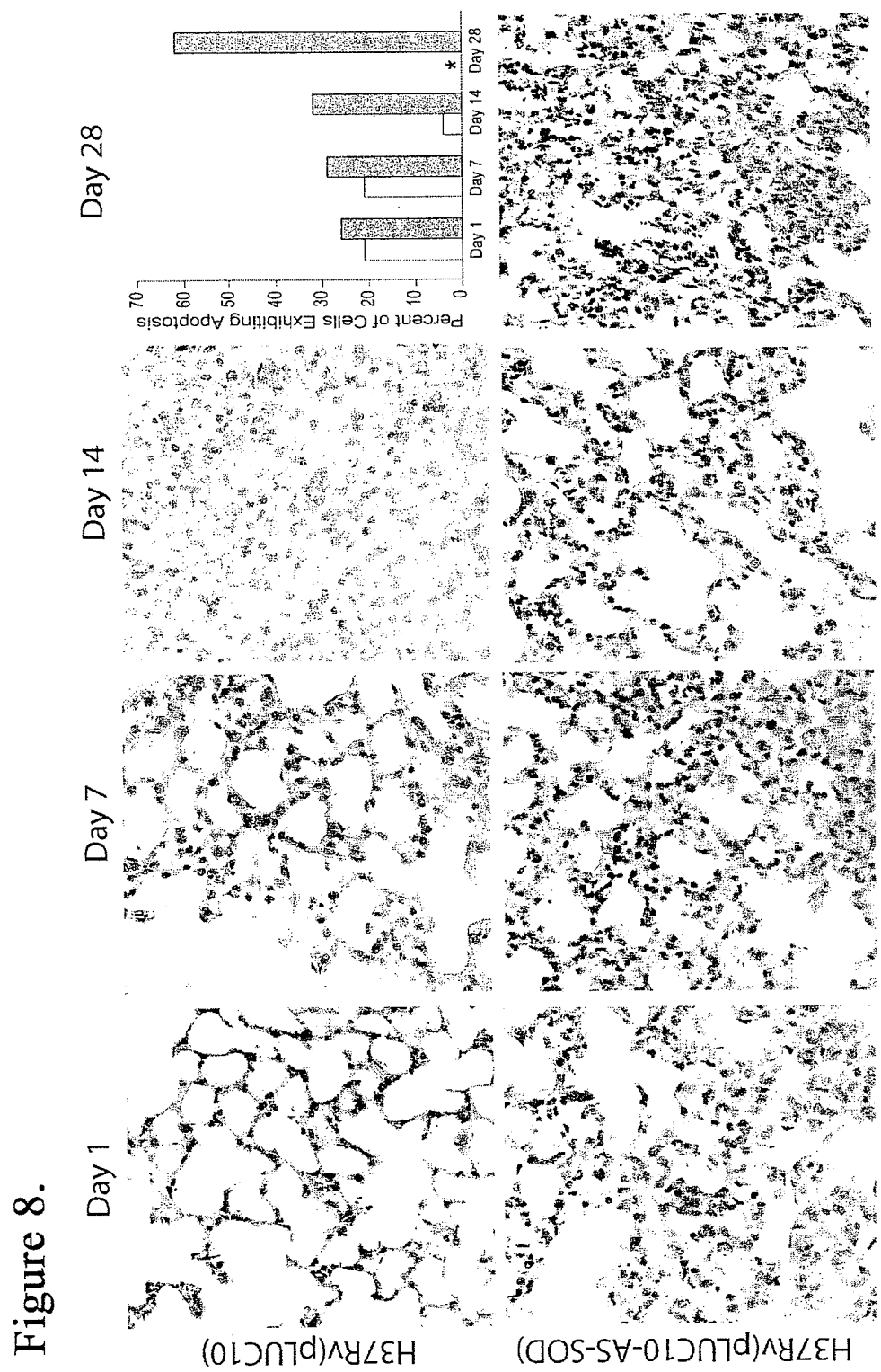

FIG. 8. Apoptosis in mouse lungs infected with the SOD-diminished strain H37Rv(pLUC10-AS-SOD) and its virulent control, H37Rv(pLUC10). Representative TUNEL-stained views were photographed using the 40× microscope objective for enlargement. Nuclei of cells undergoing apoptosis stain dark blue with TUNEL, whereas light-blue staining of extracellular amorphous material represents background (e.g., day 14 panel with H37Rv(pLUC10)). The graph plots the percent of cells that appear apoptotic over time as determined from review of multiple 40× magnification fields, H37Rv (pLUC10) (white bars) and H37Rv(pLUC10-AS-SOD) (gray bars). Mice infected with H37Rv(pLUC10) did not survive to day 28 (*). Although the percent of cells exhibiting apoptosis was comparable in the two groups of mice at day 1, there was greater interstitial infiltration with mononuclear cells and apoptosis of these cells in mice infected with H37Rv (pLUC10-AS-SOD) than in mice infected with H37Rv (pLUC10). Apoptosis had nearly ceased by day 14 in mice infected with H37Rv(pLUC10). In contrast, it increased to even higher levels by day 28 in mice infected with H37Rv (pLUC10-AS-SOD), and was associated with the renewed interstitial lung infiltration at that time [FIG. 7] that reflects the development of acquired cellular immune responses by one month post-infection, as shown in Table 5.

Figure 9:
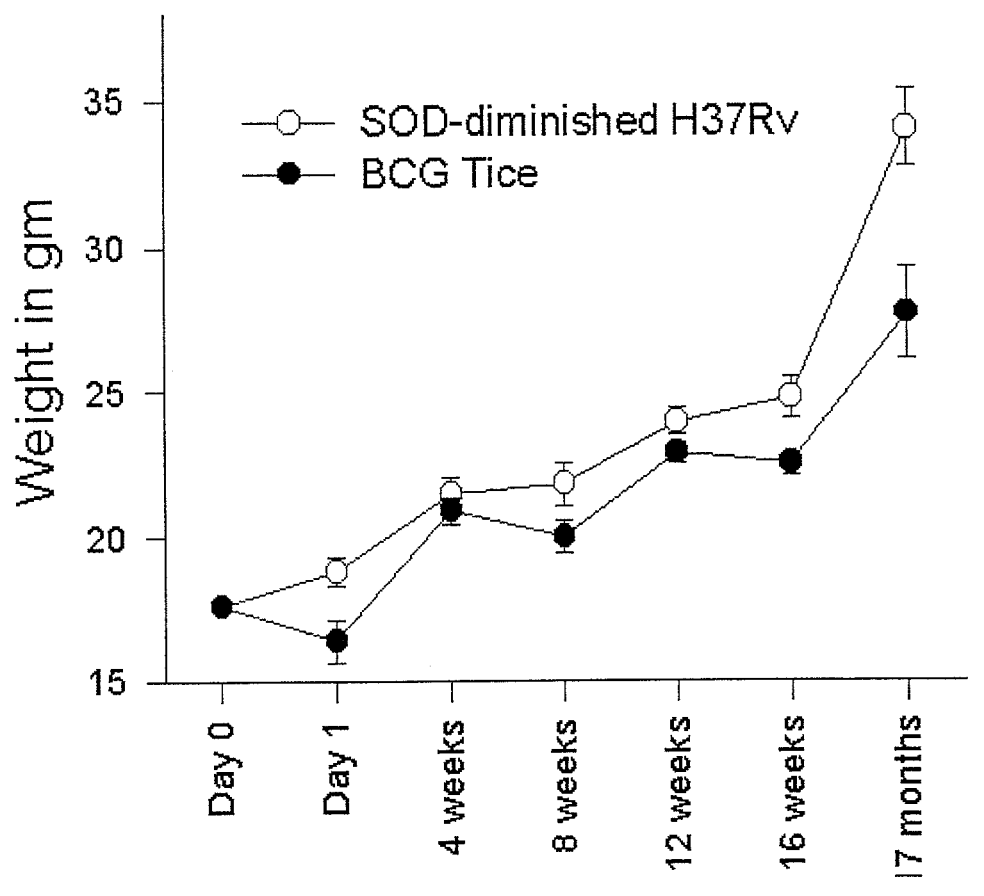

FIG. 9. Weight of mice inoculated with BCG versus SOD-diminished H37Rv. Each mouse was inoculated with $3.8 \times 10^6$ cfu of BCG or SOD-diminished H37Rv via a lateral tail vein on Day 0. The groups of mice were weighed at the indicated time points. Data points represent the mean value±std. error of weights from six to twelve mice, except for the day 0 value, which is a mean value from the whole group pre-inoculation. At 17 months the mice inoculated with BCG weighed about 6 gm less than mice inoculated with SOD-diminished H37Rv (34.1±4.6 gm versus 27.8±4.9 gm, P<0.01, two-sample Students' T-test).

Figure 10:
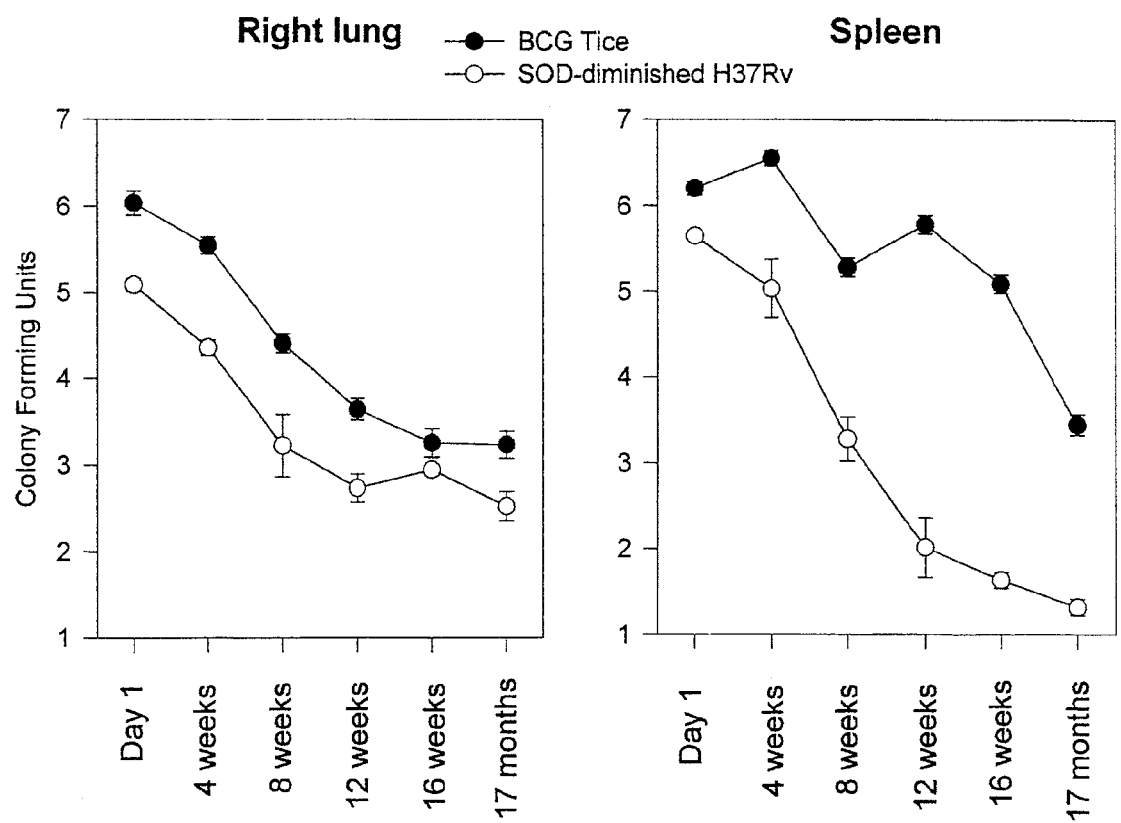

FIG. 10. Clearance of BCG versus SOD-diminished H37Rv from the spleens and right lungs of C57BL/6 mice. Each data point represents mean values±std. error from six mice, except for the 17-month values, which are from 11 mice (BCG) or 12 mice (SOD-diminished H37Rv). Initial inocula were $3.8 \times 10^6$ cfu given via a lateral tail vein on Day 0. After initial greater clearance of SOD-attenuated H37Rv in the first 24 hours, the rates of decline in counts of viable bacilli in the lungs were comparable for the two groups of mice so that approximately a 10-fold difference between strains was maintained over the 17 months of observation. In contrast, the SOD-attenuated strain was cleared more rapidly than BCG from spleens, and beyond 8 weeks a two to four log-fold difference in counts of viable bacilli was evident between the strains. At 17 months, counts of viable bacilli in the spleens were below the lower limits of detection (10 CFU) in five of 12 mice that had received H37Rv(pLUC10-AS-SOD) compared to none of 11 surviving BCG-infected mice.

Figure 11:
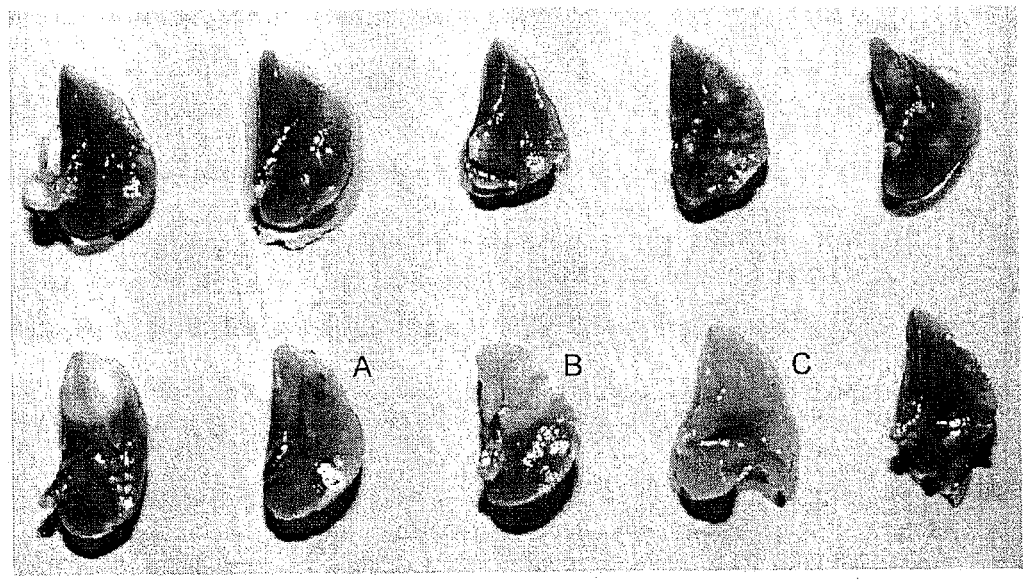
Figure 11:
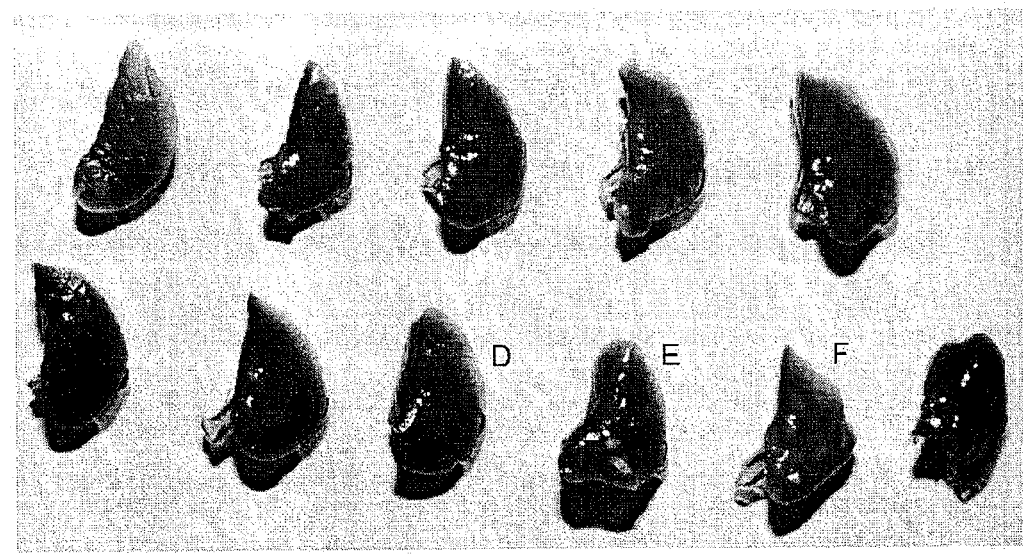

FIG. 11. Gross appearance of the left lungs of C57BL/6 mice 17 months following intravenous inoculation with attenuated strains. Upper panel, mice that received BCG; lower panel, mice that received SOD-diminished H37Rv. The white areas in the apices of the lungs of some BCG-vaccinated mice correspond to areas of alveolar consolidation with foamy macrophages by microscopy [see FIG. 12A-C, H-J]. Letters A-F indicate the lungs from which enlargement of longitudinal cross-sections are displayed in FIG. 12.

Figure 12:
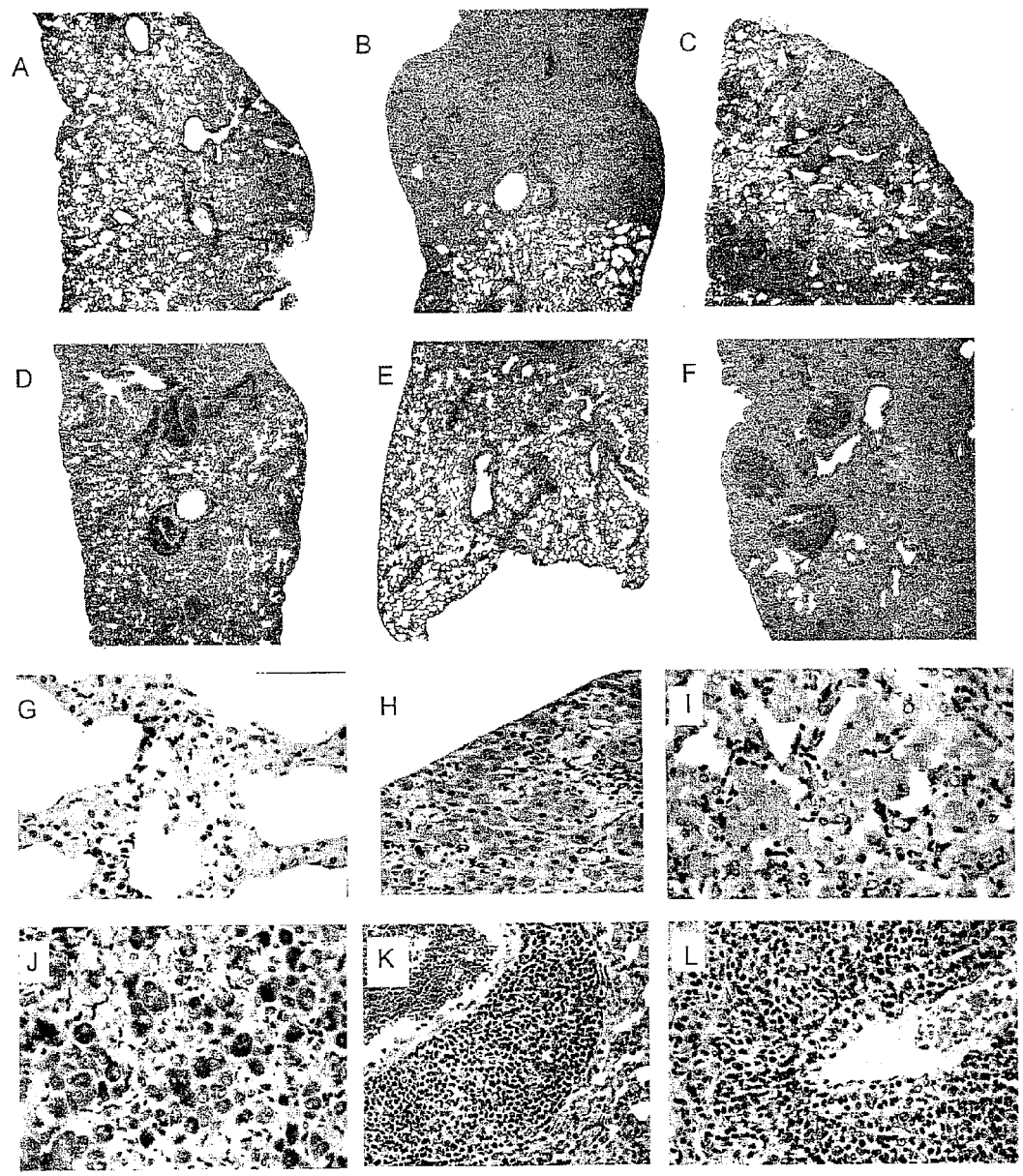

FIG. 12. Histopathologic features of mouse lungs infected with BCG and SOD-diminished H37Rv at 17 months following inoculation. Panels A-C show hematoxylin & eosin (H&E)-stained longitudinal cross-sections of three lungs from mice infected with BCG and panels D-F show lungs from mice infected with SOD-diminished H37Rv [see FIG. 11]. These were enlarged and photographed using the 4× microscope objective to display an area corresponding to about 30 to 40% of the length of the lung. Infiltration of inflammatory cells into lung interstitium, alveolar spaces, and the peribronchiolar and perivascular spaces for each lung was reviewed by a blinded observer and quantified, with results shown in Table 2. Panels G-L display and contrast some of the key microscopic features of infection with the two attenuated strains. Interstitial thickening was prominent in both groups of mice (Panel G, H&E stain). Alveolar infiltration was greatest in mice that received BCG and was characterized by large foamy macrophages [panel H & I, H&E stain; panel J, trichome stain]. AFB could sometimes be seen in these areas in BCG-infected mice on Ziehl-Neelsen staining (not shown). In contrast, mice that had received SOD-diminished H37Rv (AS-SOD) had less alveolar infiltration and greater perivascular infiltration of lymphocytes, macrophages, and plasma cells [compare the large perivascular collections of cells in Panels D & F to minimal collections in Panels A-C]. Some of these perivascular infiltrates involved the mural wall of the vessel [panels K & L, H&E stain] in a pattern suggesting lymphocyte trafficking through the vessel wall.

Figure 13:
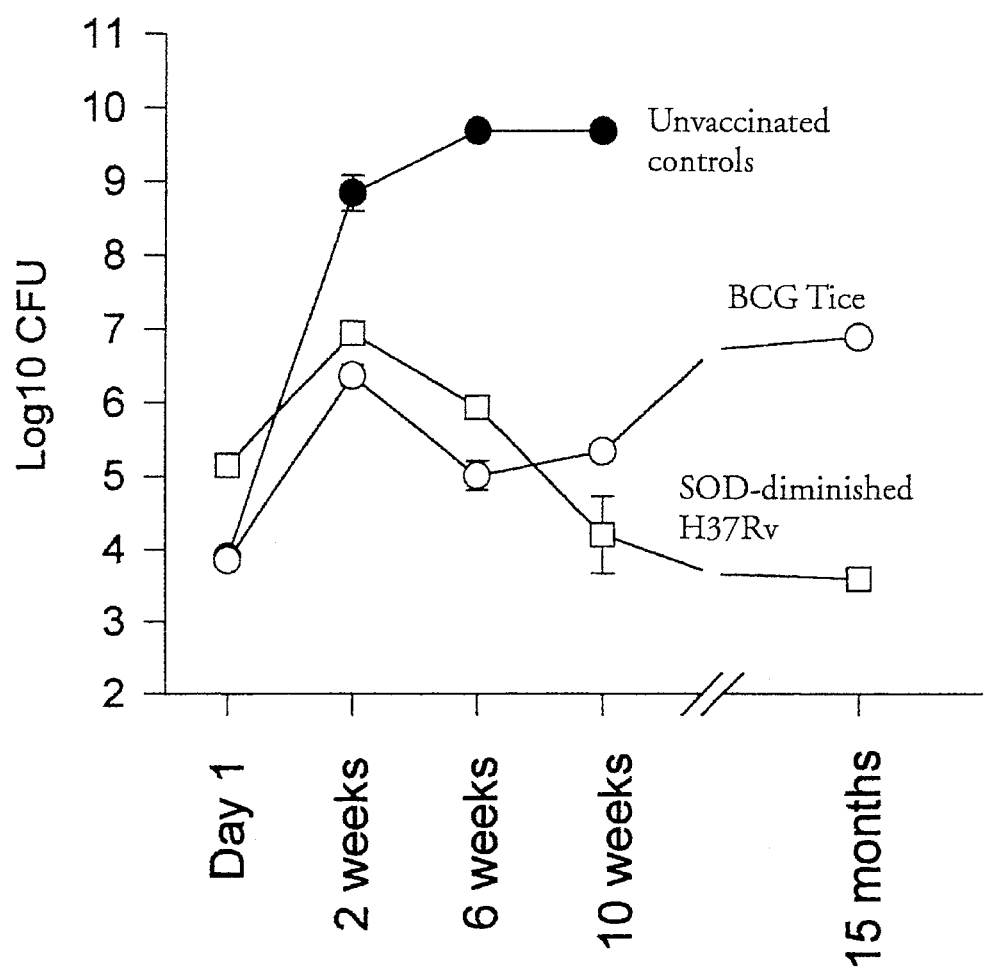

FIG. 13. Number of tubercle bacilli in the lungs of mice vaccinated with BCG (Tice) or SOD-diminished H37Rv, expressed at time points following challenge with the virulent *M. tuberculosis* Erdman strain. C57BL6 mice were immunized with either BCG (Tice) or SOD-diminished H37Rv by injecting $3.8 \times 10^6$ cfu into a lateral tail vein. After 6 weeks, the mice were challenged (on Day 0) with an intranasal inoculum of $1 \times 10^5$ cfu of strain Erdman. Mice were euthanized at selected time points and the right lungs homogenized, with bacilli enumerated on Middlebrook 7H10 agar. Values up to 10 weeks from a control group that received Erdman without prior vaccination are also shown. Each data point represents mean values±std. error from six mice, excepting the control group which comprised one to four mice for each data point, and the 15-month values which are derived from the few surviving mice at this time point. At ten weeks, there was a 40-fold difference between the numbers of bacilli recovered from mice vaccinated with BCG Tice versus SOD-diminished H37Rv (log 5.8 versus log 4.2, respectively, P<0.05). An even greater difference (3 log-fold) in counts of bacilli was noted in surviving mice at 15 months post-challenge.

Figure 14:
Figure 14:

FIG. 14. Gross appearance of the lungs of vaccinated mice 15 months after an aerogenic (intranasal) challenge with the virulent *M. tuberculosis* strain Erdman. Left panel, left lung from a mouse vaccinated with BCG Tice. Right panel, left lung from a mouse vaccinated with SOD-diminished H37Rv. In preparing this photograph, lungs were placed side-by-side and enlarged to the same degree. The lung from the mouse vaccinated with the SOD-diminished H37Rv is about the same size as the lungs of mice that were vaccinated but not challenged [FIG. 11], whereas the lung of the mouse vaccinated with BCG is much larger. This is despite the BCG vaccinated mouse weighing only 20 gm compared to 24 gm for the mouse vaccinated with SOD-diminished H37Rv. Specific enumeration of SOD-diminished H37Rv on kanamycin-containing agar at the 15-month time point showed it to be at the lower limits of sensitivity of our assay (10 cfu) compared to nearly $5\times10^2$ cfu still being present at the comparable time point in mice that had been vaccinated but not challenged [FIG. 10]. However, there were still $>10^3$ cfu of the virulent strain Erdman in this lung [FIG. 13] despite the absence of lung necrosis. This shows that vaccination with SOD-diminished H37Rv led to the containment of infection and was more effective than BCG in preventing lung damage despite the continued presence of the virulent *M. tuberculosis* strain.

FIG. 15. Histopathologic appearance of lungs of vaccinated mice 15 months after intranasal challenge with the virulent *M. tuberculosis* strain Erdman. Key histopathologic features of the lungs in FIG. 14 are displayed after staining with H&E and enlargement by microscopy. The panels on the left show longitudinal cross-sections spanning about 20-40% of the lungs of mice that had been vaccinated with BCG Tice [Panel A] or SOD-diminished H37Rv [Panel B], and were enlarged using the 4× microscope objective. Panels C-E show enlargements (25× or 40× microscope objective) of features in the lung of the BCG-vaccinated mouse. The lung of the mouse vaccinated with SOD-diminished H37Rv strain showed some regions with moderate interstitial infiltration but otherwise looked relatively healthy with prominent hilar lymph nodes, normal bronchi, and in most regions only minimal alveolar infiltration [Panel B]. In contrast, the lung from the mouse vaccinated with BCG exhibited diffuse alveolar infiltration including areas of intense necrosis within bronchi with numerous neutrophils that filled the bronchi [Panels A and C], and ulcerative bronchiectasis [Panel D]. Some regions showed squamous metaplasia of the alveolar spaces with keratinization and intraalveolar exudates [Panel E].

FIG. 16. Development of CD4+ and CD8+ T-lymphocyte responses following vaccination with BCG Tice versus SOD-diminished H37Rv, hereafter also referred to as *Bacillus* Vanderbilt-VA, or "BVV". The figure shows FACS of lymphocytes recovered from lungs of vaccinated mice 16-weeks post-challenge with *M. tuberculosis* strain Erdman. Results are grouped according to whether the mouse had been vaccinated with BCG Tice or BVV, and vaccinations occurred six weeks prior to the Erdman challenge. The control mouse had not been vaccinated or challenged. Percentages of CD4+ and CD8+ T-cells are shown in the Figure and are reported as a percent of the total lymphocyte gate. This showed 13.2% CD4+ and 6.5% CD8+ T-cells for the unvaccinated controls, 38.3% CD4+ and 18.0% CD8+ T-cells for the mouse vaccinated with BCG Tice, and 39.9% CD4+ and 38.4% CD8+ T-cells for the mouse vaccinated with BVV.

FIG. 17. Interstitial infiltration in the lungs of mice 24 hours following intravenous administration of BCG Tice and BVV. H&E-stained views of approximately 40% of a longitudinal cross-section of the left lung were photographed using the 4× microscope objective for enlargement. BCG-infected lungs showed minimal interstitial mononuclear cell infiltration, in a pattern more similar to virulent H37Rv than BVV. Photographs of H&E-stained tissue were taken using the 4× microscope objective.

FIG. 18. Proposed models of antigen presentation and immune responses following phagocytosis of (A) typical *M. tuberculosis* and BCG strains versus (B) BVV. (A) *M. tuberculosis* and BCG secrete large amounts of SOD, which blocks macrophage apoptosis and thereby enables the *bacillus* to replicate intracellularly. SOD also blunts the rapid infiltration of mononuclear and dendritic cells to the site of infection, presumably by inhibiting cytokine production triggered by the activation of NF-κB in response to stimulation of Toll-like receptors by mycobacterial factors. As the bacilli multiply in the phagosome, their antigens are presented via MHC Class II pathways to CD4+ T-cells. CD4+ T-cells activated in this fashion are now capable of secreting IFN-gamma upon interaction with other macrophages presenting tubercular antigens, thereby activating the macrophages to produce nitric oxide and reactive oxygen intermediates. This gives the host has some capacity to control infection, however the predominant reliance on nitric oxide and reactive oxygen intermediates to kill bacilli also harms other cells, causing necrosis of lung tissue. (B) SOD-diminished H37Rv (BVV) does not make enough SOD to block macrophage apoptosis, thereby unmasking apoptosis as a mechanism for killing bacilli. Furthermore, because SOD is not present to inhibit the activation of NF-κB, cytokine production is enhanced and induces the rapid influx of mononuclear and dendritic cells to the site of infection [as shown in Table 7 and Table 9]. The apoptotic bodies containing mycobacterial antigens are endocytosed by dendritic cells and presented to CD8+ T-cells via MHC Class I pathways. CD8+ T-cells contribute to the immune response by death receptor- and perforin/granzyme-related mechanisms. Dendritic cells are also very effective in presenting antigens to CD4+ T-cells. Therefore, host containment of infection is achieved by a combination of CD4+ and CD8+ responses [as shown in FIG. 16, Tables 4-6], achieving greater control with minimal necrosis [as shown in FIG. 14 and FIG. 15].

FIG. 19. Possible early mechanisms of apoptotic and cytokine signaling within the macrophage induced by intracellular tubercle bacilli and how they are inhibited by SOD. (A) Cartoon showing how SOD produced by virulent H37Rv and BCG might inhibit NF-κB activation and apoptosis. In this model, both apoptosis and the early inflammatory response are triggered by an interaction between microbial factors and Toll-like receptors (TLR). It has been shown that TLR2 and TLR4 are involved with responses to mycobacteria (Means et al., 1999; Means et al., 2001; Flynn and Chan, 2001). These Toll-like receptors (TLR) are recruited to the phagosome and activate myeloid differentiation factor 88 (MyD88). MyD88 is bi-functional, and able to initiate apoptosis by unclear mechanisms that might involve direct dimerization with fas-associated death domain (FADD) (Aliprantis et al., 2000) and/or phospholipase A2-mediated effects on ROI production via-arachidonic acid intermediate pathways. It also initiates a cascade of intracellular signaling that results in NF-κB activation and translocation to the nucleus. This causes immune response (IR) gene activation and the production of cytokines and chemokines. TNF-α binds to receptors and mediates pro-apoptotic effects via BID and the increased generation of reactive oxygen intermediates (ROIs). As NF-κB activation and apoptosis are redox-sensitive processes with superoxide being a potent catalyst of both, the extracellular SOD produced by bacilli in the phagosome may raise the threshold of the macrophage for both events. In essence, SOD blocks the innate immune responses triggered by Toll-like receptors. Furthermore, the capability of virulent M. tuberculosis to block both an early cellular infiltrate and apoptosis is likely central to its ability to establish chronic infection, effectively blocking the MHC Class I-CD8+ arm of the immune response by preventing at the onset of infection the recruitment of cells and presentation of microbial antigens needed to induce that response. Homologs of other prominent extracellular factors of M. tuberculosis including thioredoxin and glutamine synthetase have anti-apoptotic effects (Powis, Mehl, and Oblong, 1995; Saitoh et al., 1998; Tumani et al., 2000), suggesting that these M. tuberculosis enzymes may similarly serve to blunt the effect of intracellular signaling processes initiated by Toll-like receptors. (B) Apoptosis gene expression in cultured mouse macrophages infected with BVV versus H37Rv. RNAse protection assays (RPAs) show that both BVV and H37Rv induce greater early activation of FADD and TRADD (TNF receptor-associated death domain) than in uninfected control macrophages. However, after 2 to 3 days, TRADD and FADD expression falls in H37Rv-infected macrophages, remains strong in BVV-infected macrophages, and increases in uninfected macrophages. Whereas early gene expression might reflect a more generalized and inoculum-related effect of pro-apoptotic mycobacterial moieties including cord factor, after a few days SOD produced by intra-phagosomal bacilli reduces TRADD and FADD expression in the macrophage cultures infected with H37Rv. In effect, virulent M. tuberculosis inhibits apoptosis of its host cell so that it can continue to replicate within it. In contrast, since SOD production is diminished in the cultures infected with BVV, this inhibition does not occur and TRADD and FADD expression increases over time. Therefore, apoptosis is more likely to occur in cells infected with BVV than cells infected with virulent M. tuberculosis, as illustrated in vivo in FIG. 8.

Figure 20:
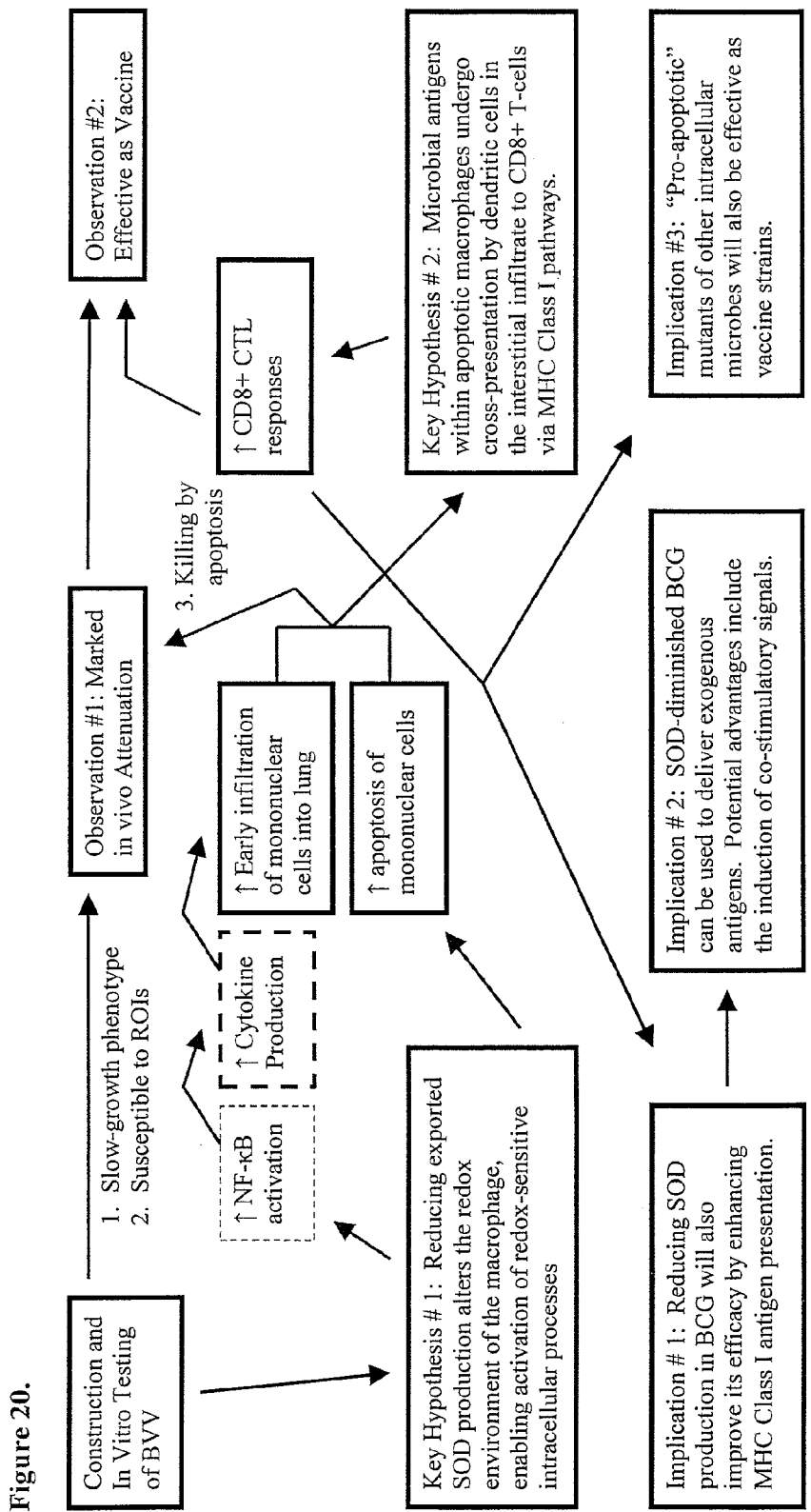

FIG. 20. Summary of the key observations, mechanisms, hypotheses, and implications associated with the vaccine efficacy exhibited by BVV.

Figure 21:
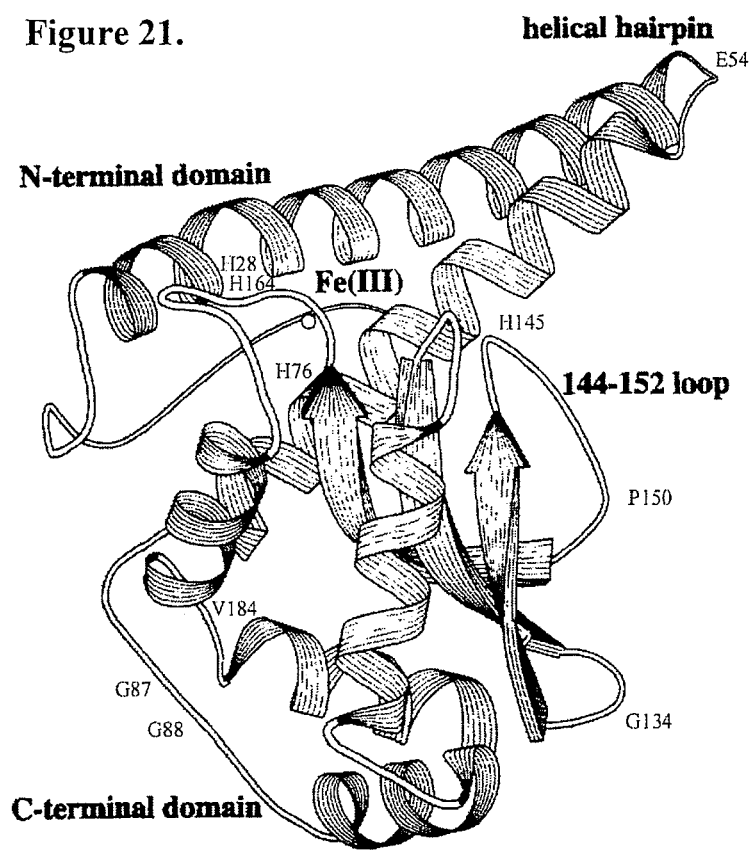

FIG. 21. Ribbon figure of SOD monomer showing positions of deleted and substituted amino acids in the present SOD mutants.

Figure 22:
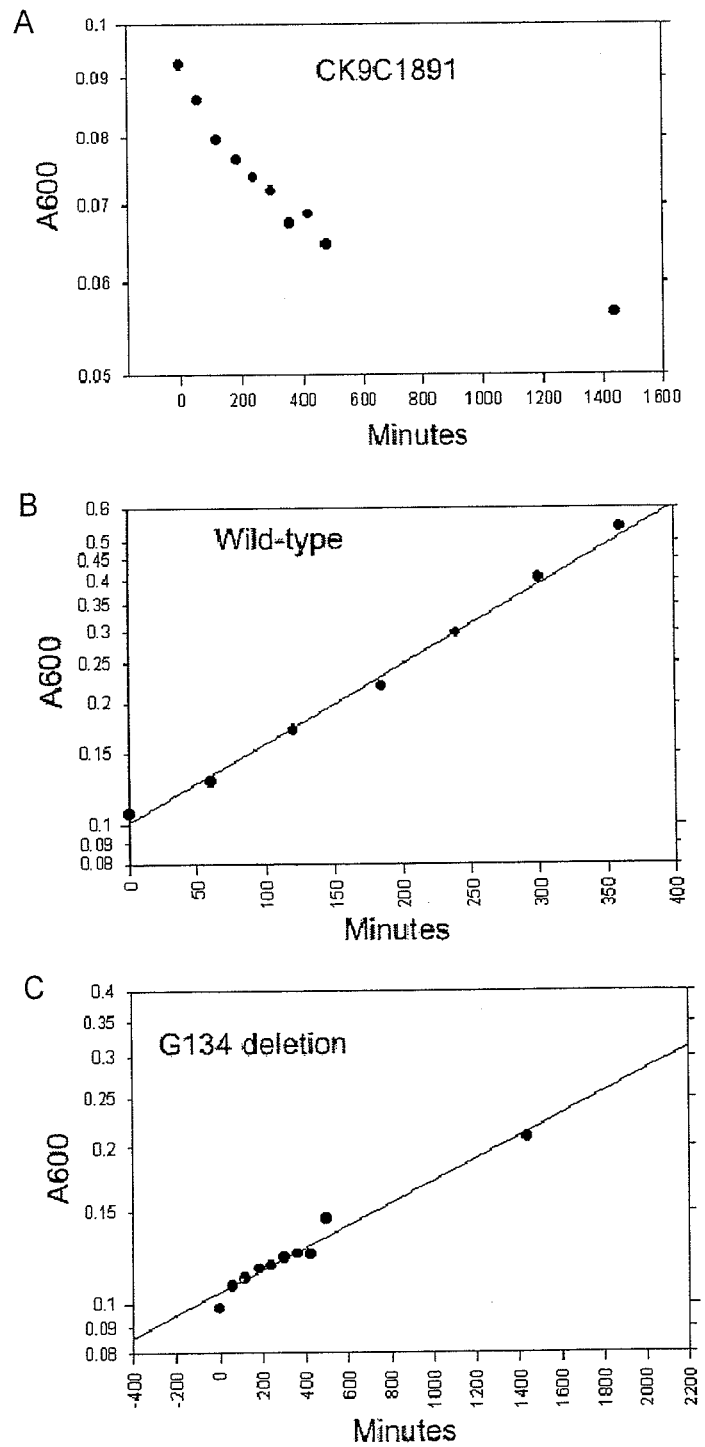

FIG. 22. Bacterial density versus time plots, used to estimate the enzymatic activity of M. tuberculosis SOD mutants, as determined by their ability to complement the growth of SOD-deficient E. coli in minimal media. Mutants were created by deleting amino acids in inter-domain regions of SOD or by substituting critical histidine residues associated with binding of the metal co-factor by lysine [see Table 11]. SOD-deficient E. coli cannot grow in minimal media due to the sensitivity of some metabolic pathways to an adverse intracellular redox environment, but growth is restored in the presence of SOD. (A) Growth curve of the SOD double-negative E. coli strain CK9C1891 in minimal media as reflected by bacterial density (absorbance at 600 nanometers [A600]) over time of incubation in minimal media. The inoculum was made by transferring colonies from nutrient agar to minimal media, so the fall in A600 value reflects autolysis induced by abrupt cessation of growth in a strain that previously was growing vigorously. (B) Growth curve of CK9C1891 complemented with the wild-type M. tuberculosis sodA allele, showing restored growth and a doubling rate of every 155 minutes. (C) Growth curve of CK9C1891 complemented with a mutant M. tuberculosis sodA allele in which G134 has been deleted, showing slow growth and a calculated doubling time of 1,360 minutes. Therefore, the G134 mutant grows at 13% the rate of CK9C1891 containing the wild-type sodA allele, suggesting that the mutant SOD has about 13% of the activity of the wild-type M. tuberculosis SOD [FIG. 10].

Figure 23:
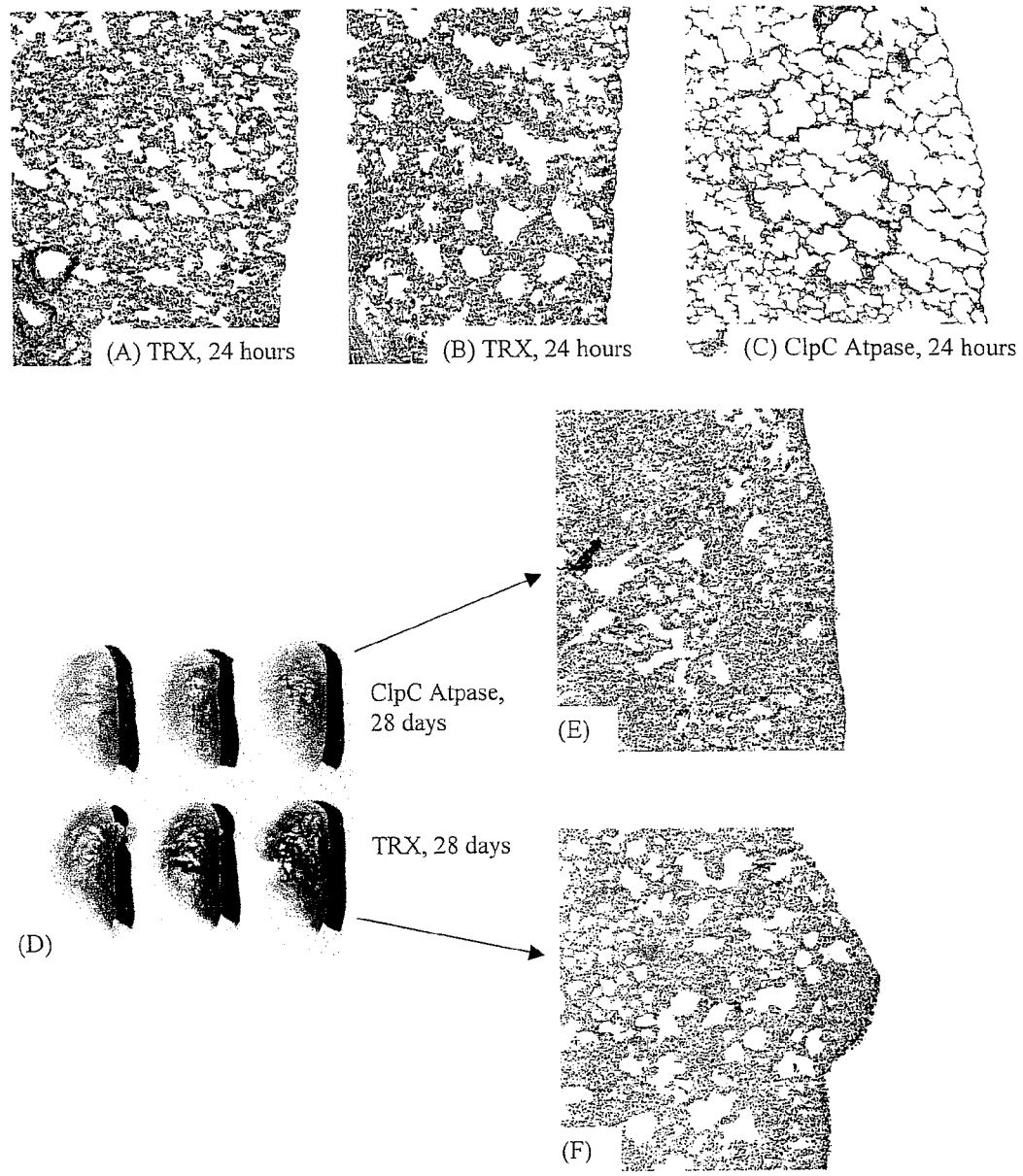

FIG. 23. Lung inflammation induced by a TRX-diminished mutant of M. tuberculosis. Panels A and B show rapid interstitial infiltration of the lungs of two mice with mononuclear cells at 24 hours post infection with H37Rv(pHV203-AS-TRX). This was in contrast to less interstitial infiltration induced by H37Rv(pHV203-AS-ClpC Atpase) (Panel C), although both mutant strains had comparable bacillary counts in the lung [FIG. 6]. However, by 28 days, lungs infected with H37Rv(pHV203-AS-ClpC Atpase) showed much greater alveolar infiltration than lungs infected with H37Rv (pHV203-AS-TRX), as evidenced by greater lung consolidation upon gross inspection of the lungs (Panel D, the whiter appearance indicates greater alveolar infiltration with leukocytes), and histopathologic appearance (Panels E and F). Both H37Rv(pHV203-AS-TRX) and H37Rv(pHV203-AS-ClpC Atpase) were attenuated relative to virulent H37Rv [FIG. 6], however the TRX-diminished strain exhibited histopathologic findings similar to those exhibited by the SOD-diminished strain at both day 1 and day 28, suggesting that both innate and adaptive immune responses were enhanced by reduction of an anti-apoptotic and anti-inflammatory microbial factor.

Figure 24:
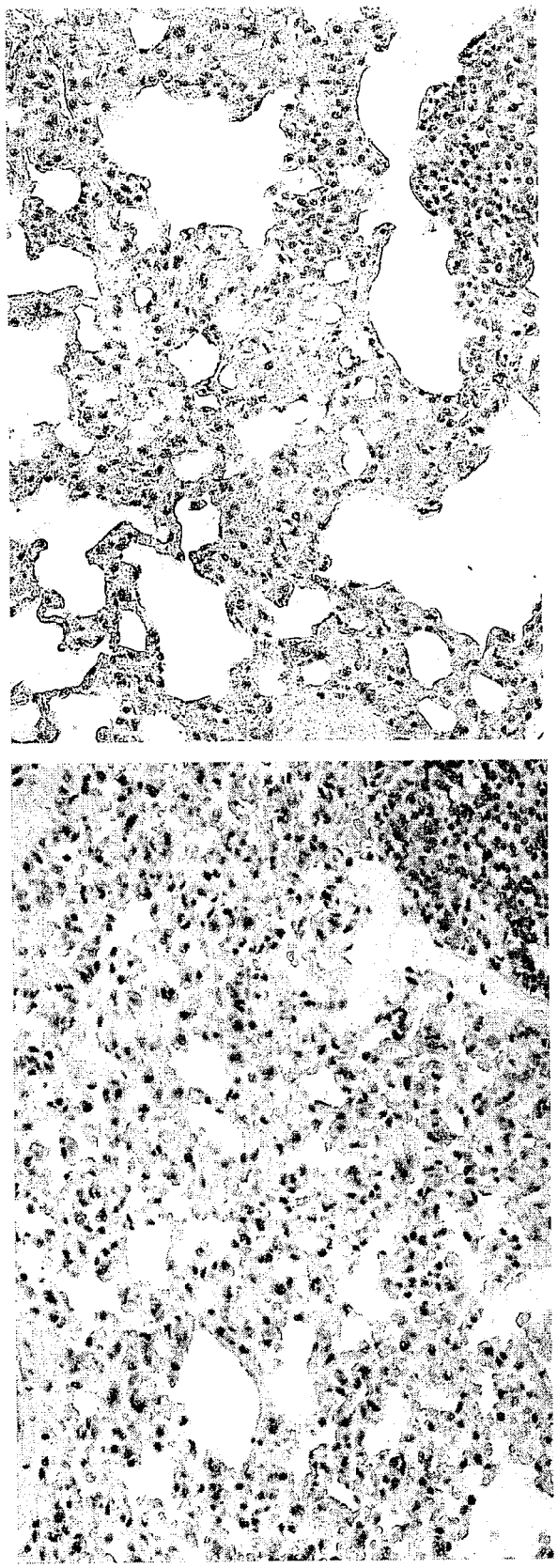

FIG. 24. CD8+ T-cells in lungs at 17 months following vaccination with BVV versus BCG. Tissue sections were incubated with anti-CD8 antisera and reactive cells were identified with horseradish peroxidase (HRP). CD8+ T-cells stain brown with dense blue nuclei, whereas other cell types are clear to gray/blue with dense blue nuclei. Both photomicrographs are representative of what was observed throughout the lung, and were enlarged with the 20× microscopic objective. Panel A shows numerous CD8+ T-cells in a BVV-vaccinated mouse in the interstitial spaces of the lung. Panel B shows relatively few CD8+ T-cells in a BCG-vaccinated mouse.

Figure 25:
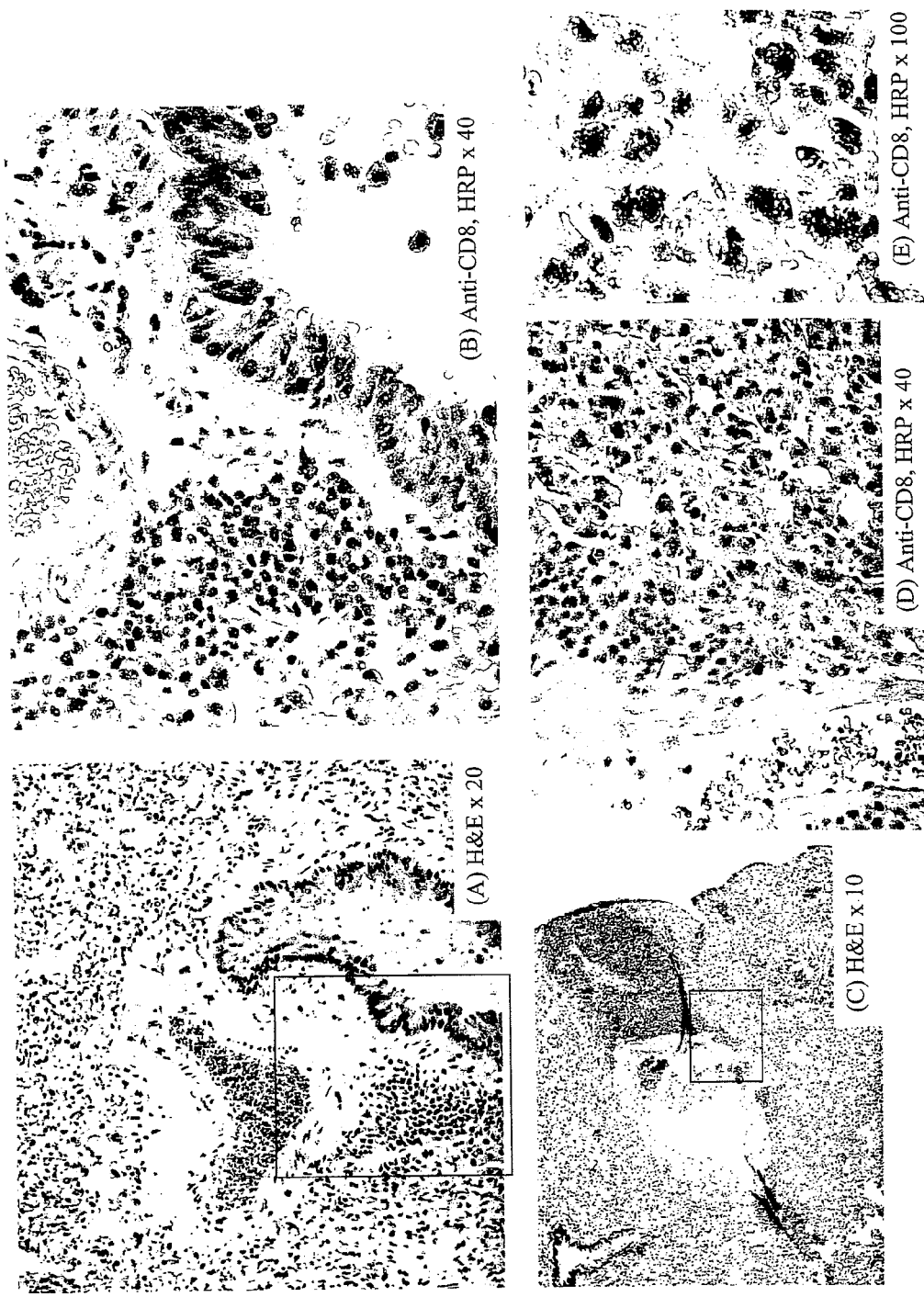

FIG. 25. CD8+ T-cells in the interstitial spaces and within peribronchovascular lymphoid aggregates of lungs of mice vaccinated with BVV. Panel A shows an H&E-stained section of lung that includes a typical peribronchovascular lymphoid aggregate. The portion of Panel A within the box is enlarged in Panel B and staining with anti-CD8 antisera and horseradish peroxidase (HRP) shows multiple CD8+ T-cells within the lymphoid aggregrate. Panel C is stained with H&E and shows a large vein, a large perivascular lymphoid aggregate and areas of interstitial infiltration. The portion within the box is enlarged in Panels D and E (×40 and ×100, respectively) and stained with anti-CD8 antisera and HRP. It shows numerous CD8+ T-cells in the perivascular infiltrate and in the lung interstitium.

DETAILED DESCRIPTION OF THE INVENTION

It must be noted that, as used in the specification and the appended claims, the singular forms "a," "an," and "the"

include plural referents unless the context clearly dictates otherwise. Thus, for example, reference to "an enzyme" includes multiple copies of the enzyme and can also include more than one particular species of enzyme.

The present invention teaches that reducing an anti-apoptotic enzyme produced by *M. tuberculosis* results in profoundly greater vaccine efficacy. Thus, the invention provides a method for facilitating antigen presentation via construction of pro-apoptotic vaccines made by reducing the production of microbial anti-apoptotic enzymes including SOD, thioredoxin, thioredoxin reductase, glutamine synthetase, and possibly other redox related enzymes such as glutathione reductase (glutaredoxin), other thioredoxin-like proteins, other thioredoxin reductase-like proteins, other glutaredoxin-like proteins, other thiol reductases, and other protein disulphide oxidoreductases. Many of these enzymes are highly conserved in all cellular life forms and many overlap or are identical to the enzymes that detoxify reactive oxygen intermediates due to the central role of reactive oxygen intermediates as a trigger for apoptosis. The premise of making pro-apoptotic vaccines relates to the capability of the enzyme from the intracellular pathogen to block apoptosis when the pathogen is within the host cell, as is the case with virulent strains of *M. tuberculosis*. Accordingly, by reducing the activity of these specific enzymes it is possible to simultaneously attenuate the microbe and enhance the presentation of its antigens, as dendritic and other immune cells process the apoptotic macrophages containing microbial antigens.

The iron-cofactored superoxide dismutase (SOD) of *M. tuberculosis* inhibits host cell apoptosis as well as the recruitment of mononuclear cells to the site of infection. By reducing the activity of SOD in mutant strains of *M. tuberculosis*, both the rapid recruitment of mononuclear cells and apoptosis of these cells were enhanced, such that the mutant strain was markedly attenuated. Furthermore, the mutant strain was highly effective as a vaccine in a mouse model, surpassing the efficacy of the current vaccine for tuberculosis, BCG. The mechanism of enhanced vaccine efficacy involves the induction of greater CD8+ T-cell responses following vaccination with SOD-diminished *M. tuberculosis* than after vaccination with BCG. The greater CD8+ T-cell response occurs because by reducing SOD production by *M. tuberculosis*, innate immune responses were facilitated which achieved the co-localization of apoptotic macrophages with antigen-presenting cells, effectively creating the conditions for apoptosis-associated antigen cross-presentation in vivo. In effect, by producing large amounts of extracellular SOD, *M. tuberculosis* inhibits the development of conditions conducive to the development of strong acquired immune responses. This is advantageous to *M. tuberculosis* in that blunting apoptosis-associated antigen cross-presentation (by preventing the in vivo conditions needed to achieve it) enables chronic infection to become established by inhibiting the full development of acquired host immune responses. By reducing SOD, not only did our *M. tuberculosis* mutants become markedly attenuated and more susceptible to innate immunity, but also the "cross-talk" between the innate and acquired immune responses was allowed to proceed such that strong acquired cellular immune responses developed. In effect, we have learned how to achieve apoptosis-associated antigen cross-presentation in vivo by reducing the production of anti-apoptotic microbial factors which block it. The result is a highly effective live-attenuated whole-cell vaccine in which essentially all microbial antigens can be processed by the host immune system to induce strong cellular immune responses. More specifically, the present invention involves a whole-cell vaccine for tuberculosis made by diminishing the activity of iron-manganese superoxide dismutase in a strain of *M. tuberculosis* or *M. bovis*, including *M. bovis* BCG and other strains that have been already attenuated using physical, chemical, or molecular genetic methods.

Although one example of a vaccine was derived from *M. tuberculosis*, the invention teaches how vaccines of other intracellular pathogens can be developed by reducing or eliminating the production of anti-apoptotic bacterial factors, as well as bacterial factors that inhibit the activation of host intracellular processes involved in the rapid recruitment of inflammatory cells.

Some anti-apoptotic microbial enzymes can be eliminated without adversely affecting the ability to cultivate the microbe as a vaccine strain. For such enzymes, traditional molecular genetic techniques including allelic inactivation can be used to construct the modified microbe. However, some enzymes are absolutely essential for the viability of the microbe, such that they cannot be eliminated entirely. For these enzymes, methods are needed to construct mutants with a partial rather than complete reduction in the activity of the anti-apoptotic enzyme. Anti-sense RNA overexpression (Coleman, Green, and Inouye, 1984) is one such strategy for constructing mutant strains with partial phenotypes, and is particularly useful as a tool to screen and identify which essential enzymes can be reduced to render a pro-apoptotic phenotype.

Previously work with microorganisms has yielded a few publications wherein enzymes associated with apoptosis have been altered. Modifications to the Fe, Mn SOD have already been documented for *Salmonella* species (Tsolis et al., 1995, which is incorporated herein by reference in its entirety), and found to occur in nature for *Shigella* species (Franzon et al., 1990, which is incorporated herein by reference in its entirety) and *M. tuberculosis* (Mang et al., 1992, which is incorporated herein by reference in its entirety). Modifications for Zn, Cu SOD have also been documented in *M. tuberculosis* (Dussurget et al., 2001, which is incorporated herein by reference in its entirety), *Legionella pneumophila* (St. John and Steinman, 1996, which is incorporated herein by reference in its entirety), *Salmonella* species (Fang et al., 1999; Farrant et al., 1997; De Groote et al., 1997, which are incorporated herein by reference in their entirety), *Actinobacillus pleuropneumoniae* (Sheehan et al., 2000, which is incorporated herein by reference in its entirety), and *Brucella abortus* (Tatum et al., 1992; Latimer et al., 1992, which are incorporated herein by reference in their entirety). Though not through direct manipulation, decreased Glutathione reductase activity has been shown in *Salmonella* species (Storz and Tartaglia, 1992, which is incorporated herein by reference in its entirety). Additionally, both auxotrophs and null mutants of Glutamine synthetase have also been disclosed in *Salmonella* species (Funnage and Brenchly, 1977; Klose and Mekalanos, 1997, which are incorporated herein by reference in their entirety).

The present invention provides a method of stably modifying a microbe, whereby the microbe retains or increases immunogenicity but loses or reduces pathogenicity in a subject, comprising reducing but not eliminating an activity of an enzyme produced by the microbe, whereby reducing the activity of the enzyme attenuates the microbe or further attenuates the microbe.

One way of accomplishing the modifications of the invention involves the application of a process of targeted incremental attenuation, hereafter referred to as "TIA." This method includes the following steps: a) identifying an enzyme that is essential for the full expression of in vivo survival of the microbe, b) mutating a gene encoding the essential microbial enzyme or obtaining from another species a homologous gene, c) replacing in a microbe the gene encoding the essential microbial enzyme with one or more of the mutated genes or homologous genes from step b), thereby reducing but not eliminating in the microbe the activity of the essential enzyme identified in step a), and d) identifying an attenuated microbe of step c) that survives to confer protective immunity in vivo. As TIA is described and exemplified below, it will be apparent that each of the steps of the process may be practiced independently of the other steps to accomplish the goal of that step. For example, the step of replacing or mutating a pro-apoptotice enzyme can be practiced independent of the TIA process.

There are two critical factors in TIA. First, it is clear that there are some amino acid residues that are not entirely essential for the function of the enzyme. Most enzymes have evolved from other enzymes and only gradually did their enzymatic activity become optimized for the task they currently perform. Therefore, most minor mutations (e.g., single amino acid deletions, substitutions) introduced into an enzyme will be more likely to diminish rather than eliminate enzymatic activity unless they are directed at a critical region. Starting initially with regions of the enzyme likely to be non-critical based on assessment of X-ray crystal data and consensus sequence data will identify regions where amino acids can be deleted sequentially (i.e., one amino acid, then two amino acids, then three amino acids), resulting in progressive reductions in enzyme activity before it is abolished entirely. It should be feasible to practice TIA as a means to construct attenuated mutants of pathogenic bacteria and other microbes with every essential enzyme. Examples of such mutants are provided below.

Second, when the enzyme mutants are used to replace the wild-type enzyme that they will result in changes in pathogenicity that correlate with changes in their enzymatic activity. It is likely that there will be a range of enzymatic activity over which there is a rough direct correlation between activity and virulence. Thus, using SOD as an example, mutants with greater than 30% SOD activity may be fully virulent in vivo, mutants with 10% to 30% SOD activity will exhibit growth rates and disease-causing capability in vivo that ranges from minimal to almost full virulence, and mutants with less than 10% SOD activity are expected to be completely avirulent.

Step 1: Identification of Essential and Anti-Apoptotic Enzymes

Types of Essential and Anti-Apoptotic Enzymes

A person of skill can identify an enzyme that is essential for the full expression of microbial survival in vivo and/or confers an anti-apoptotic effect upon the host cell. Guidance as to how to identify essential and anti-apoptotic enzymes for use in TIA, is provided below and in Examples 1 and 13.

The essential enzyme can be an enzyme involved in an essential metabolic pathway of the microbe. For example, it can be an enzyme involved in basic cell metabolism and respiration including enzymes necessary for glycolysis, the pentose phosphate pathway, the tricarboxylic acid cycle, or glyoxylate cycle. It can be an enzyme involved in amino acid biosynthesis, or nucleic acid biosynthesis including those that synthesize purines. It can be an enzyme involved in the replication of nucleic acids, including DNA and RNA polymerases, and nucleic acid repair enzymes. It can be an enzyme involved in lipid biosynthesis including acyl-CoA synthases, acyl-CoA dehydrogenases, acetyl-CoA C-acetyltransferases and synthetic carboxylases. Other categories of probable essential enzymes include oxidoreductases, oxygenases, and dehydrogenases, as well as enzymes for the ubiquinone cytochrome b reductase complex, cytochrome c oxidase, as well as aerobic and anaerobic phosphorylative electron transport chains. Some microbes have unique essential enzymes such as those involved in mycobacterial mycolic acid synthesis and polyketide synthesis. Some microbes including *M. tuberculosis* require iron and have special enzymes for the production of iron-scavenging siderophores, the mycobactins and the exochelins. Other microbes produce specialized enzymes that act as virulence factors due to their effect on host cell structures. These include phospholipases, lipases and esterases, which might attack cellular or vacuolar membranes, as well as proteases. In addition, enzymes involved in signal transduction including sensor histidine kinases and response regulators are potential targets for TIA.

The essential enzyme targeted in the present method can be an enzyme that helps protect the microbe against the normal host immune response, such that when less enzymatic activity is present, the host's immune system becomes more efficient in controlling and eradicating the pathogen. For example, for an intracellular bacterial pathogen, microbial enzymes that detoxify the reactive oxygen intermediates (ROIs) and reactive nitrogen intermediates (RNIs) that neutrophils and macrophages make to mediate killing of the microbe are essential for the full survival of certain microbes. Other types of enzymes that might be expected to specifically affect the ability of the microbe to survive in vivo are those normally induced under conditions of stress, including heat-shock stress-regulatory enzymes. Thus, they are good targets for modification by the methods of the present invention.

An enzyme of an intracellular bacterium that normally has an anti-apoptotic effect upon the host cell can be targeted in the present method. Reducing the activity of an anti-apoptotic enzyme increases apoptosis of macrophages and other cells in which an intracellular bacterium resides, thereby resulting in increased host cell apoptosis with concomitant killing of the microbe. This has the advantage of enhancing innate immune responses and fundamentally altering antigen presentation pathways in a manner than improves vaccine efficacy.

Specific examples of the latter categories of enzymes include iron-manganese superoxide dismutases (SOD), zinc-copper superoxide dismutases, catalases, nitrate reductases, and other microbial enzymes that affect the intracellular redox environment including the thioredoxin system, glutathione reductases (glutaredoxin), other thioredoxin-like proteins, other thioredoxin reductase-like proteins, other glutaredoxin-like proteins, other thiol reductases, and other protein disulphide oxidoreductase. Also, ClpC Atpases are natural targets as they are stress-induced enzymes that are involved in the induction of microbial redox-related enzymes. Specific approaches to developing mutants of these enzymes are discussed below.

Methods for Identifying Essential and Anti-Apoptotic Enzymes

Figure 1:
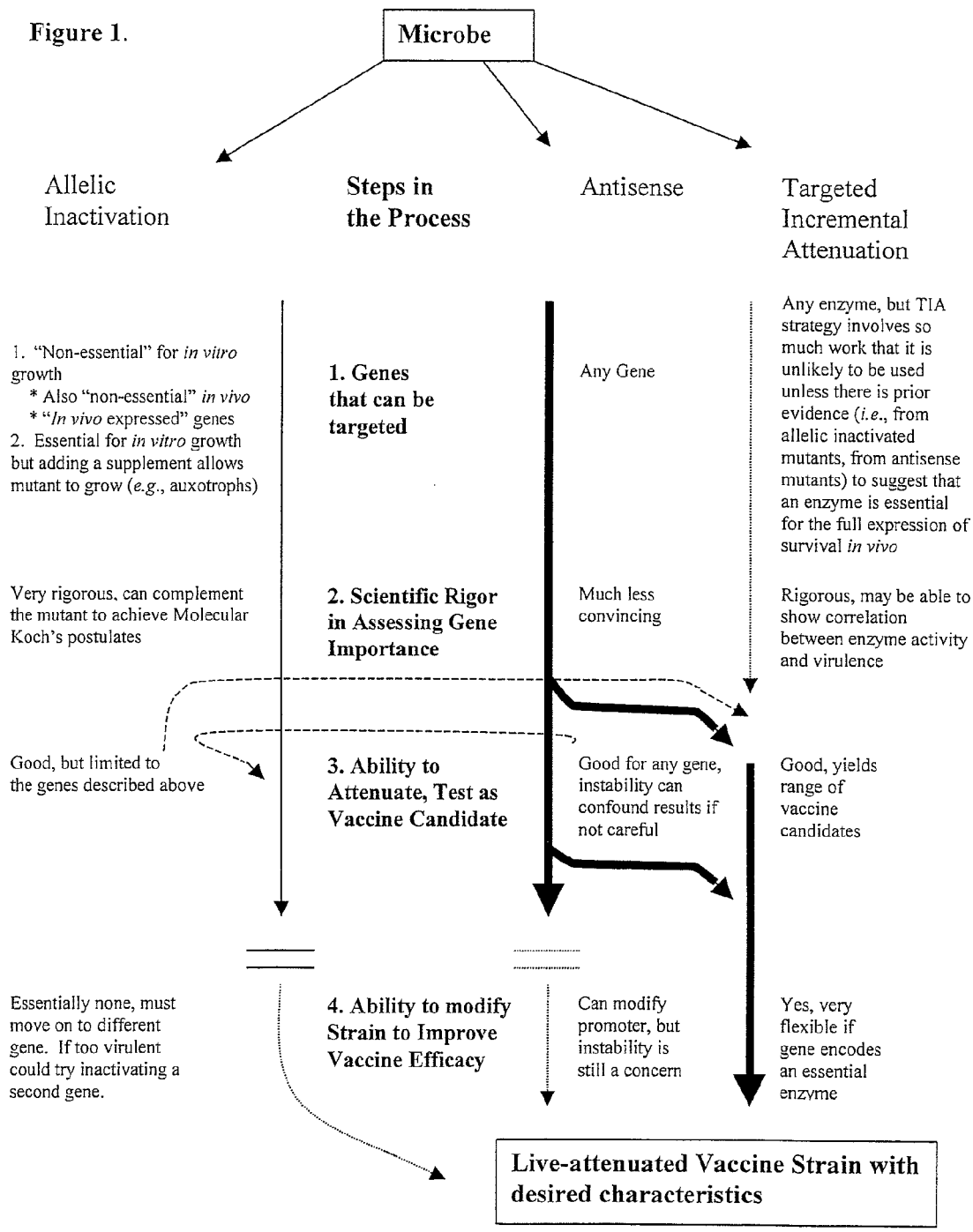
FIG. 1. Flowsheet outlining the key steps in developing new live-attenuated vaccines and comparing the strengths and weaknesses of the various genetic techniques that can be used to modify microbes and reduce the activity of essential and anti-apoptotic enzymes. The key features of the current paradigm (Allelic Inactivation, also called "Gene Knockout") are contrasted with Antisense (AS) RNA expression and a new strategy (Targeted Incremental Attenuation, or "TIA"). AS techniques and TIA have an advantage over allelic inactivation in that they can be used to construct mutants with a partial phenotype, thereby allowing microbial genes that are essential for in vitro growth to be targeted. TIA can be used to generate mutant enzymes covering a range of enzymatic activity, and the allele encoding the wild-type enzyme can be replaced by mutant alleles to yield incrementally attenuated mutants. Both allelic inactivation mutants and TIA mutants have stability advantages over AS mutants. Unless exceptionally fortunate with allelic inactivation, the most time-efficient method (as indicated by bold lines and arrows) for using recombinant DNA technology to make novel live-attenuated microbes for use as vaccines involves using AS to identify the important genes for mediating microbial survival in vivo and determining whether mutants with reduced expression of that gene are effective as a vaccine (through step #3). Then, TIA can be used to build a more stable version of the vaccine. The AS/TIA strategy offers advantages over the traditional allelic inactivation strategy and over AS techniques alone, permitting fine-tuning of the vaccine to achieve the right balance between attenuation and immunogenicity while still producing a stable vaccine with minimal risk for reverting back to the original phenotype. TIA can be practiced on a microbe that has already been attenuated by other means to reduce the activity of an anti-apoptotic microbial factor, and render a pro-apoptotic effect upon the microbe that enhances its immunogenicity and efficacy as a vaccine.

Essential enzymes for in vivo growth can be identified by making mutants with reduced enzyme activity and determining that they survive less well than the parent strain in vivo. A variety of techniques can be used to directly identify essential enzymes including allelic inactivation, antisense techniques, or the creation of enzyme mutants with reduced enzymatic activity [FIG. 1]. Anti-apoptotic enzymes can be identified by making mutants of an intracellular pathogen with reduced enzyme activity and determining that there is increased apoptosis of the host cells either in vivo [Example 4] or in cell culture. Some enzymes will be both essential and anti-apoptotic in nature and it is with these enzymes that the dual aspects of the invention are needed, teaching how to construct stable pro-apoptotic mutants for use as vaccines.

In some circumstances it may be inferred that an enzyme is essential for in vivo survival based on the vital role of an homologous or analogous enzyme in other microbial species or in eukaryotic species. When this is the case, it is possible to proceed directly to step (b) of TIA to make less efficient mutants of the enzyme.

In many circumstances, especially with pathogenic microbes in which allelic inactivation is time-consuming or when assessing the importance of a gene that is essential for in vitro cultivation, antisense techniques offer the most time-efficient way to identify an essential in vivo gene, including genes that render anti-apoptotic effects upon their host cell. For example, the amount of enzyme produced by the microbe can be reduced by transforming the microbe, for example a bacterium or fungus with an anti-sense nucleic acid that reduces the efficiency of translation of the nucleic acid. The antisense nucleic acids can be complementary to a region of messenger RNA transcribed from the coding sequence of the gene for the enzyme. A person of skill in the art can produce and use an antisense nucleic acid, as described in Example 1 below.

Antisense methods (Coleman, Green, and Inouye, 1984) have been shown to be useful in attenuating virulent strains of bacteria and assessing the importance of specific microbial genes for in vivo pathogenicity (Kernodle et al., 1997; Wilson et al., 1998). They can also be used to assess the potential of an enzyme-diminished mutant as a vaccine candidate before using TIA to make a single safe, non-reverting form of the vaccine, or to construct multiple vaccine candidates covering a range of attenuation. Therefore, the most time-efficient way to practice the TIA invention for enzymes for which there is no prior evidence to demonstrate that they are essential in vivo, is to use antisense techniques to demonstrate attenuation of the enzyme-diminished mutant or possibly even to show preliminary evidence of vaccine efficacy before practicing TIA to make the final vaccine candidate [FIG. 1].

Figure 2:
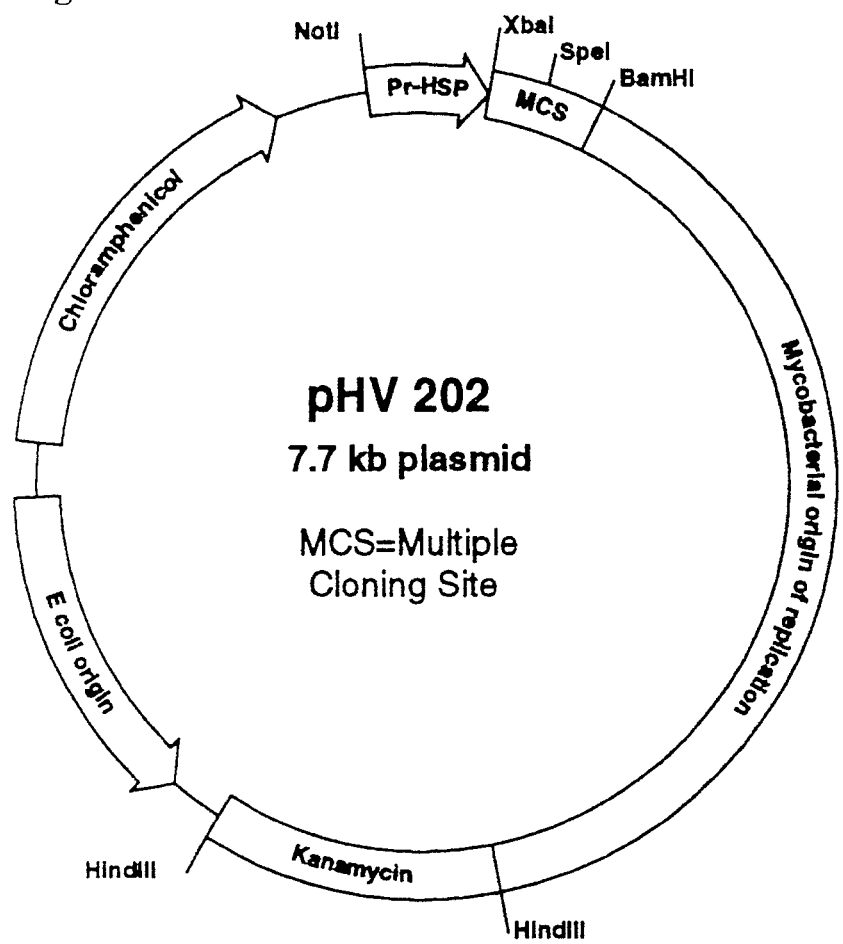
FIG. 2. Map and features of the antisense expression and shuttle vector pHV202. The *E. coli* origin of replication and mycobacterial origin of replication enable the plasmid to replicate both in *E. coli* and mycobacterial species, including *M. tuberculosis*. The chloramphenicol and kanamycin resistance genes are used as selectable markers to identify transformants. Antisense DNA fragments are cloned into restriction sites in the multi-cloning site (MCS) behind the promoter of the 65-kDa heat-shock protein (Pr-HSP). The MCS includes the following unique sites: XbaI, SpeI, MluI, and BamHI. Genetic manipulations to construct the antisense plasmids are performed in *E. coli* with subsequent electroporation into *M. tuberculosis* strains.

For example, to identify essential in vivo genes of *M. tuberculosis*, antisense mutants have been constructed either in a novel pHV202 plasmid [FIG. 2], in pLUC10 (Cooksey et al., 1993), or in both vectors. [Note: throughout this document, the terms pHV202 and pHV203 are used interchangeably: pHV203 was derived from pHV202 by repairing a mutation in the promoter region of the 65 kDa heat-shock protein that drives expression of the antisense fragment. Strains and plasmids are summarized in Table 1]. Both pHV202 and pLUC10 are *E. coli*-Mycobacterial shuttle vectors that can replicate in *E. coli* and as well as Mycobacterial species including *M. tuberculosis*. In general a 150- to 300-bp DNA fragment of the gene encoding the protein to be suppressed is taken and cloned into either the multicloning site of pHV202 or a HindIII site upstream of the luciferase gene in pLUC10 (Cooksey, Crawford, Jacobs, Jr., and Shinnick, 1993). The HindIII site in pLUC10 is not unique; therefore, some additional manipulations and verification were needed with this vector to confirm that the ligation product had the correct orientation and reassembly of the various DNA fragments. In both cases, the DNA fragment is oriented behind the promoter of the 65 kDa heat-shock protein (Pr-HSP) in a direction antisense to its orientation behind its endogenous promoter on the *M. tuberculosis* chromosome. Therefore, expression of Pr-HSP on the plasmid generates an antisense mRNA transcript that anneals with the mRNA transcript of the chromosomal gene, stimulating degradation by RNase and causing diminished translation with reduced synthesis of the gene product. DNA fragments in the mid-region of the open reading frame (ORF) are selected to enhance the specificity of the effect because although fragments closer to the 5' end of the ORF likely would yield stronger inhibition, in some proteins, such regions might be more apt to be similar to unrelated proteins (e.g., because of similar leader peptide regions).

Antisense constructs have been made for the following *M. tuberculosis* genes: SOD (sodA), thioredoxin (trx), and a ClpC Atpase (gene Rv3596c). The role of SOD in tuberculosis has been debated but appears important in the pathogenesis of some other infections (Igwe et al., 1999; Fang et al., 1999). *M. tuberculosis* makes two superoxide dismutases, a iron-manganese co-factored enzyme encoded by sodA, and a copper-zinc enzyme encoded by sodC. It was recently reported that allelic inactivation of sodC makes *M. tuberculosis* more susceptible to reactive oxygen intermediates (ROIs) but does not reduce virulence in guinea pigs (Dussurget et al., 2001). The authors also reported that they were unable to inactivate sodA and suggested that it might be essential for viability, supporting the value of the present strategy of using anti-sense techniques to determine its importance in vivo. Of note, in *Legionella pneumophila*, iron co-factored SOD is essential for viability and allelic inactivation of the chromosomal gene is not possible unless a second episomal copy of the allele is present (Sadosky et al., 1994). Thioredoxin (TRX) is a 12 kDa protein encoded by trx with similar ROI scavenging activities as SOD (Powis, Briehl, and Oblong, 1995). The TRX of *M. leprae*, which shares 85-90% identity with *M. tuberculosis* TRX, has been cloned into *M. smegmatis* and confers resistance to killing by human macrophages (Wieles et al., 1995; Wieles et al., 1997). As the genes for thioredoxin and thioredoxin reductase are on a polycistronic genomic element, the antisense element is expected to reduce the expression of both thioredoxin and thioredoxin reductase. ClpC Atpase was selected on the basis on its importance in the pathogenesis of infections caused by other intracellular pathogens (Rouquette et al., 1998; Nair, Milohanic, and Berche, 2000). The SOD-diminished mutants grow slowly, taking 4 weeks or more to produce pinpoint colonies and 7 to 8 weeks to reach the size of a 3-week colony of the parent *M. tuberculosis* strain.

Figure 3:
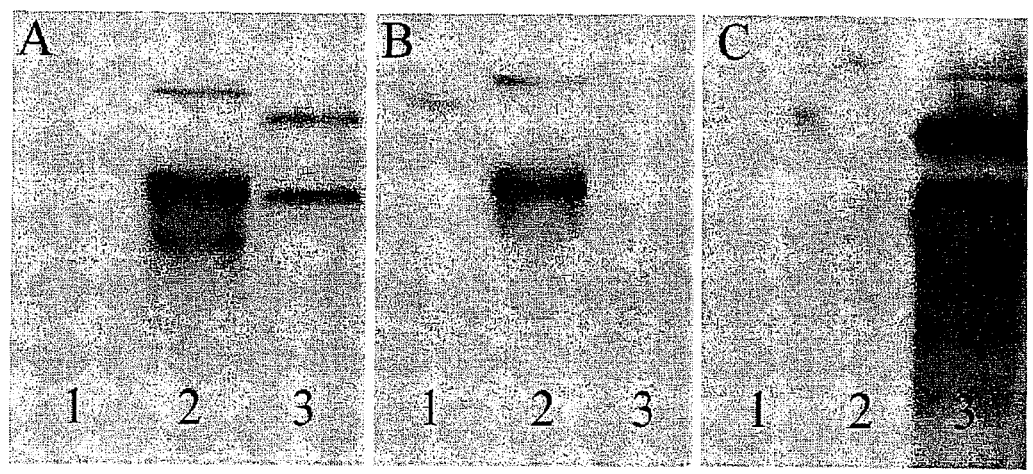
Figure 4:
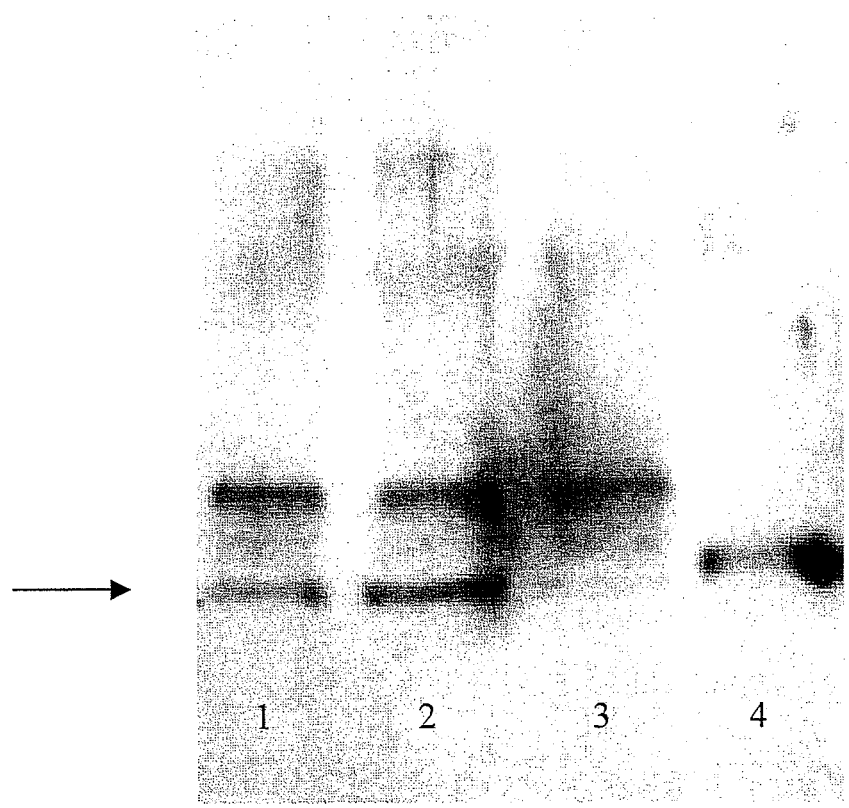
Figure 5:
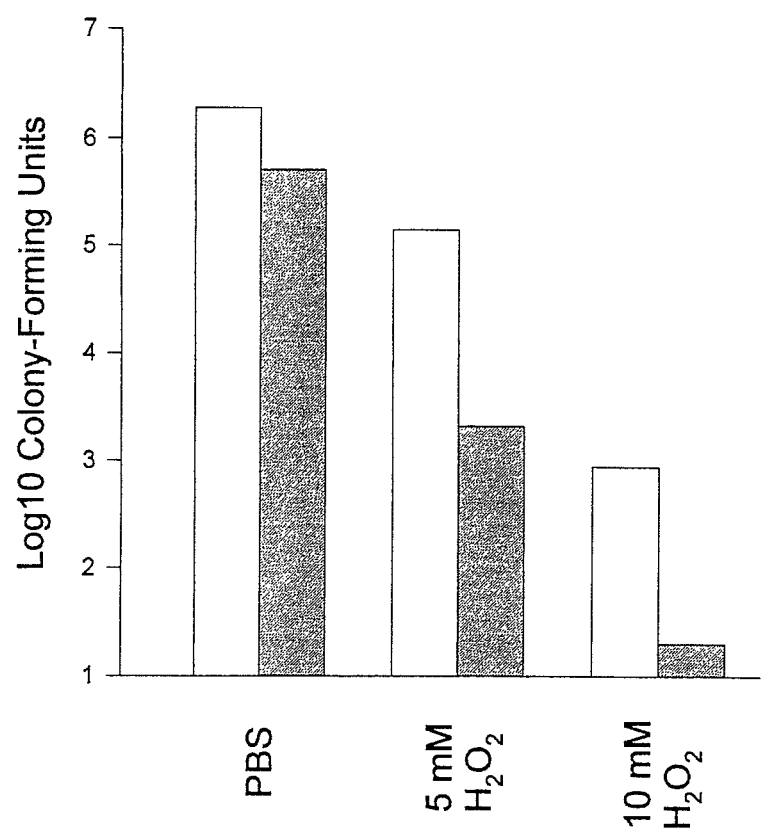

Initial evaluation of the AS-SOD expression vector suggested strong expression of the 151-bp AS-sodA RNA in mycobacteria [FIG. 3]. *M. smegmatis* was used to test the function of Pr-HSP as Northern hybridization is even more difficult to perform in slow-growing mycobacteria, and the Pr-HSP is recognized by both *M. tuberculosis* and *M. smegmatis* (DasGupta et al., 1998), enabling the latter to be used as a surrogate for expression in the former. Following electroporation of the AS-SOD vectors into H37Rv, diminished production of SOD was observed [FIG. 4]. Also, the SOD-diminished H37Rv strain exhibited greater susceptibility to hydrogen peroxide [FIG. 5].

Figure 6:
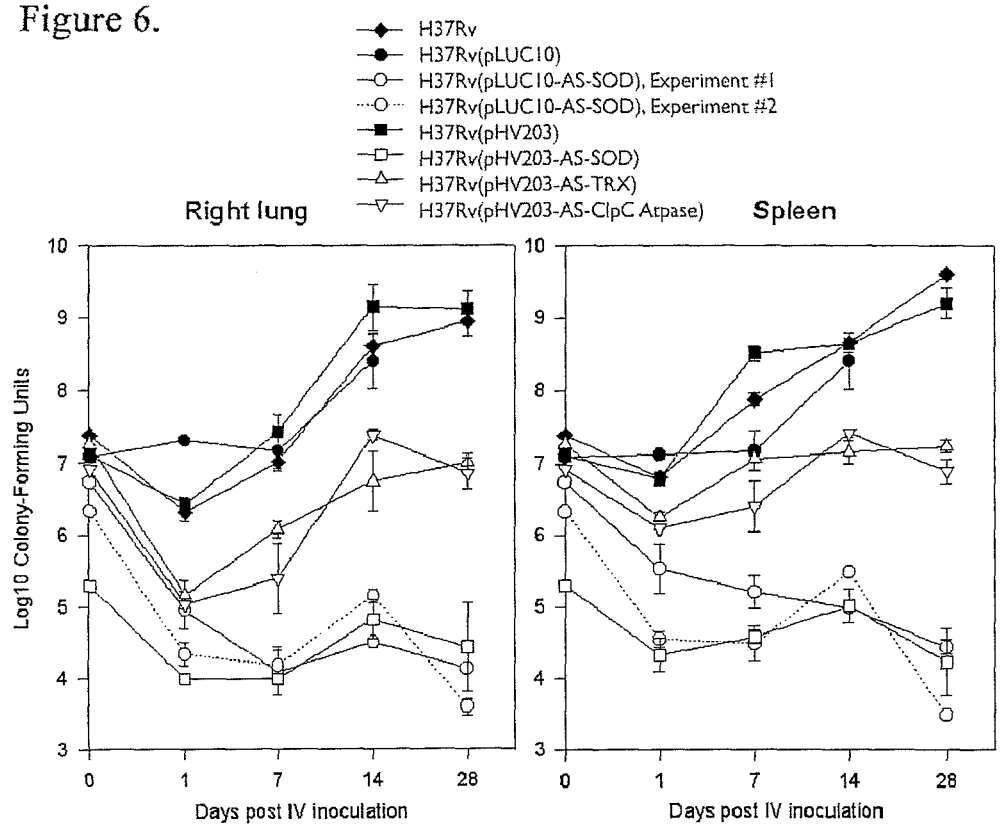

In vivo experiments show that the SOD-diminished strains are markedly attenuated in C57Bl/6 mice compared to the control strains [FIG. 6]. Mutants with diminished TRX and clpC Atpase production were also attenuated, but not to the same degree as the SOD-diminished strains. Therefore, each of these three enzymes was identified as being essential for the full expression of in vivo survival of *M. tuberculosis*.

Lung infection with the SOD-attenuated H37Rv strains and their virulent controls produced markedly different histopathologic findings [FIG. 7]. Especially notable was the greater interstitial infiltration with mononuclear cells, mostly macrophages, at 24 hours in mice infected with SOD-attenuated H37Rv, despite the smaller numbers of viable bacilli at this time. Furthermore, the microscopic features evolved differently over time for the two groups. The early interstitial mononuclear cell infiltrate diminished over the first two weeks in mice infected with SOD-attenuated H37Rv, and again became prominent by day 28, likely due to the development of a cellular immune response in the $3^{rd}$ and $4^{th}$ weeks post-infection. In contrast, lungs of mice infected with virulent H37Rv control strains showed minimal interstitial infiltration at 24 hours with a modest increase in septal thickening by day 7. However, by day 14 there was marked interstitial mononuclear cell infiltration as well as alveolar polymorphonuclear and mononuclear cell infiltration with prominent necrosis. If the mouse survived, the infiltration and necrosis were even more intense at day 28.

TUNEL (TdT [terminal deoxynucleotidyltransferase]-mediated dUTP nick end labeling) assessment of DNA fragmentation in the lungs of mice infected with SOD-diminished H37Rv showed that about 30 percent of the interstitial mononuclear cells were apoptotic at day 1, day 7, and day 14 [FIG. 8]. Apoptosis increased markedly to involve 60 percent of total cells at 28 days, coinciding with the renewed interstitial mononuclear cell infiltration at this time [FIG. 7]. In contrast, although apoptosis was identified at day 1 and day 7 in mice infected with virulent *M. tuberculosis*, it appeared to primarily involve cells lining the alveolar spaces and only rare apoptotic mononuclear cells were observed in the interstitial space. By day 14, mice infected with virulent bacilli exhibited minimal apoptosis (<5 percent), despite the development of marked interstitial and alveolar infiltration. Apoptosis of mononuclear cells in the interstitial inflammatory infiltrate occurred almost exclusively in the lungs of mice infected with SOD-attenuated H37Rv.

Another experiment was set up to compare how mice respond to infection with SOD-diminished H37Rv versus BCG Tice over a longer duration of time, with frequent sampling over the initial 16 weeks followed by terminal sacrifice and cultures. Compared to mice receiving BCG, mice receiving the SOD-diminished H37Rv strain gained 6.3 gm more weight over 17 months [FIG. 9] and exhibited better eradication of bacilli from the spleen [FIG. 10]. Furthermore, at 17 months there were distinct differences in the gross appearances of the lungs of mice [FIG. 11]. Scoring of various histopathologic features by a-blinded reviewer showed that in general there was greater alveolar infiltration among mice that had received BCG, resulting in consolidation of portions of the lung [Table 2; FIG. 12]. This is an undesired outcome and the SOD-diminished strain caused less of it than BCG, which is the current vaccine for tuberculosis. Also, there was greater perivascular infiltration with lymphocytes, macrophages, and plasma cells among mice that had received SOD-diminished H37Rv [Table 2; FIG. 12]. This suggests that there are differences in the immune responses induced by SOD-diminished H37Rv compared to BCG, and similar perivascular collections have been correlated with protective immunity in some animal model studies involving vaccines. Combined, these results show that prolonged infection with SOD-diminished H37Rv was tolerated better than the current vaccine for tuberculosis, BCG.

Next, the efficacy of SOD-diminished H37Rv and BCG Tice as vaccines was compared. Six weeks following intravenous vaccination, C57Bl/6 mice were challenged with an intranasal inoculum of the virulent Erdman strain of *M. tuberculosis*, delivering an inoculum of $10^4$ to $10^5$ cfu to the lungs as assessed by backcounts of homogenates from the lungs of mice sacrificed on Day 1 post-challenge. This was a very rigorous challenge, as vaccinated mice are much more susceptible to virulent *M. tuberculosis* administered aerogenically than by the IV route (North, LaCourse, and Ryan, 1999) and a large inoculum was used. For example, in other recent trials involving new vaccine candidates, Jackson et al. used an IV challenge (Jackson, Phalen, Lagranderie, Ensergueix, Chavarot, Marchal, McMurray, Gicquel, and Guilhot, 1999) whereas Hondulas et al. challenged with only 5 to 10 cfu by aerosol (Hondalus, Bardarov, Russell, Chan, Jacobs, Jr., and Bloom, 2000). Detailed enumeration was performed over the first 10 weeks, showing marked restriction of growth of the virulent Erdman strain in both vaccinated groups of mice compared to unvaccinated controls [FIG. 13]. By the time of terminal sacrifice of surviving mice at 15 months post-challenge, the lungs of mice that had been vaccinated with SOD-diminished H37Rv were markedly healthier than those of mice that had received BCG [FIG. 14, FIG. 15].

To determine the immune correlates of vaccine efficacy, repeat experiments were performed that included fluorescence activated cell sorting (FACS) of single-cell suspensions of mouse lungs to monitor the CD4+ and CD8+ T-cell responses that developed over time. In the first T-cell experiment, vaccination with either BVV or BCG produced an increase in the percent of cells exhibiting CD4+ surface antigens to eventually comprise 40% of total lymphocytes [FIG. 16]. In contrast, marked differences were noted in CD8+ T-cell responses, with BVV-vaccinated mice exhibiting more than double the percent of lymphocytes expressing CD8+ surface antigens at 4 months post-challenge compared to BCG-vaccinated mice [FIG. 16]. Additional experiments reproduced the observation of induction of greater CD8+ T-cell responses by BVV than by BCG, as well as a dose-dependent response to vaccination [Tables 3-6]. Immunohistochemical staining for CD8+ T-cells [FIG. 24] confirmed the results of FACS, providing confirmation via an independent assay that BVV induces stronger CD8+ T-cell responses than BCG. It also provided information about the location of CD8+ T-cells within the lung, showing that they were present in high number in the interstitial spaces and in the large perivascular collections of lymphoid cells [FIG. 25] that are so prominent in BVV-vaccinated mice [FIG. 12].

Next, we focused on the relationship between innate immune responses and the development of acquired T-cell responses. We have shown above that mice infected with BVV exhibit rapid mononuclear cell infiltration into the lung [FIG. 7] and apoptosis of these cells [FIG. 8], whereas the host response to infection with virulent H37Rv develops more slowly. As with H37Rv, BCG also produces abundant amounts of SOD (Florio et al., 1997) and is attenuated by other means (Behr et al., 1999). To assess the early host response to infection that underlies the development of strong cellular immune responses, C57Bl/6 mice were inoculated intravenously with either BCG or SOD-diminished H37Rv, and lungs were harvested at 24 hours and examined microscopically. As had been shown previously with H37Rv, mice infected with BCG exhibited minimal early mononuclear cell infiltration of the lungs, in sharp contrast to the early interstitial inflammation present in the lungs of BVV-infected mice [FIG. 17]. Single-cell suspensions prepared from the lungs of mice three days after intravenous inoculation with BCG, BVV, or H37Rv showed that cells expressing F4/80 surface antigens indicating predominant monocytic derivation were greatest in the BVV-infected mice [Table 7]. In contrast, T-cell populations were similar among the vaccination groups at this early time-point [Table 8], providing additional evidence that it is the early influx of cells of mononuclear derivation that leads to the subsequent development of enhanced CD8+ responses by several weeks post-vaccination. Another experiment showed that dendritic cells were also present in the lungs of mice infected with BVV to a greater extent than in mice infected with H37Rv [Table 9]. Finally, SOD-diminished BCG induced robust CD8+ T-cell responses that were much greater than the CD8+ T-cell responses observed following vaccination with BCG [Table 10], being comparable in magnitude to the CD8+ T-cell responses induced by BVV [FIG. 16, Tables 4-6]. The generation of much greater CD8+ T-cell responses in mice vaccinated with SOD-diminished BCG compared to its isogenic parent BCG strain establishes that it is the reduction of SOD activity that is responsible for enhancing CD8+ T-cell responses. This indicates that bacterial strains, including BCG, that are already attenuated sufficiently to be used as a vaccine can be modified to enhance their immunogenicity by reducing the activity of an anti-apoptotic microbial factor.

The above exemplifies how the expression of antisense nucleic acids can be used to identify which enzymes are essential for microbial survival in vivo and demonstrate that such an attenuated microbe is useful as a vaccine. Thus, the invention provides a highly effective tuberculosis vaccine that owes its efficacy to the presence of a greater initial innate host response (i.e., greater rapid infiltration of inflammatory cells with apoptosis of host cells) when SOD production by *M. tuberculosis* is reduced. The greater innate host response establishes the conditions (i.e., apoptotic macrophages containing microbial antigens that are then processed by antigen-presenting cells, including dendritic cells to achieve apoptosis-associated antigen cross-presentation in vivo) that permit the development of stronger adaptive immune responses than are achieved following vaccination with BCG [FIG. 18]. Furthermore, these experiments show that the iron-cofactored SOD of *M. tuberculosis* is central to its ability to cause disease. It inhibits innate immune responses, including apoptosis, which are needed to develop strong adaptive immune responses [FIG. 19]. A summary of the key observations, mechanisms, hypotheses, and implications associated with the vaccine efficacy of BVV are illustrated in FIG. 20.

Since the importance of SOD to the pathogenesis of tuberculosis has been demonstrated herein, TIA can be applied to this essential enzyme to construct additional stable, non-reverting vaccine candidates covering a range of attenuation. And as noted above, attempts to make *M. tuberculosis* deficient in the production of iron co-factored SOD using allelic inactivation have been described to be unsuccessful (Dussurget, Stewart, Neyrolles, Pescher, Young, and Marchal, 2001), because iron co-factored SOD is either absolutely essential for the growth of *M. tuberculosis* or because iron co-factored SOD-inactivated mutants grew too slowly to be identified and cultivated. The antisense nucleic acids of this invention can be useful directly as a means of further attenuating a partially attenuated bacterium or to reduce the production of microbial anti-apoptotic enzymes, thereby modifying antigen presentation in vivo in a manner that improves immunogenicity. For example, reduction of SOD production in BCG improves its immunogenicity as demonstrated herein [see Example 10].

Identification of an enzyme produced by an intracellular bacterium that exerts an anti-apoptotic effect upon the host cell when the bacterium is inside of the host cell can be performed by making mutants of the microbe with reduced production of one or more enzymes that have biological activity related to the oxidation-reduction (redox) status of a cell or which interact directly with apoptosis signaling within the cell. Preferred enzymes that are involved in cellular redox status or interact directly with apoptosis signaling within a host cell can be taken from a list including iron-manganese SOD, zinc-copper SOD, thioredoxin, thioredoxin reductase, glutathione reductase (glutaredoxin), glutamine synthetase, other thioredoxin-like proteins, other thioredoxin reductase-like proteins, other glutaredoxin-like proteins, other thiol reductases, and other protein disulphide oxidoreductases.

Mutants with diminished enzyme activity can be made by using TIA, or well known molecular protocols, including, allelic inactivation, antisense techniques. Then the mutant can be compared to the parent strain for its ability to induce apoptosis of a macrophage or other eukaryotic cell in which the microbe exists intracellularly, using in vitro and in vivo assays that are well-known to a person of skill in the art. For example, the parent bacterium and modified bacterium can be used to infect macrophage cell cultures derived from mice, other mammals, or a human host, using monocyte-derived macrophages from the bone marrow or peripheral blood. Alternatively, a macrophage or other cell lines such as human U-937 cells in which the bacterium exists intracellularly can be used. Apoptosis can be identified using DNA fragmentation assays (for species such as mice in which DNA fragmentation can be readily identified) or specific stains for apoptosis. Apoptosis stains include TUNEL (TdT [terminal deoxynucleotidyltransferase]-mediated dUTP nick end labeling) and can be used to assess and compare the amount of DNA fragmentation found in cells infected by the parent versus modified bacterium. Alternatively, the induction of eukaryotic genes associated with apoptosis can be compared, using RNAse protection assays as illustrated in Example 9 [see FIG. 19B], RNA hybridization membranes, microarray gene chips, or other technologies known to those skilled in the art. In vivo models can also be used to determine whether reducing the production of a microbial enzyme increases host cell apoptosis. For example, microscopic examination of lung tissue stained by TUNEL showed that SOD-diminished H37Rv induced much greater apoptosis of mononuclear cells in the interstitium of the lung compared to infection with a virulent H37Rv control [FIG. 8].

Different species of intracellular bacteria will vary in the specific anti-apoptotic enzyme they produce to help keep their host cell from undergoing apoptosis. As bacteria use extracellular factors to control their environment, a strong clue suggesting that a specific enzyme exerts an anti-apoptotic function for a specific bacterial species is the extracellular production of the enzyme by the bacterial species. In Grain-negative species of bacteria, an enzyme secreted into the peri-plasmic space might have a similar significance. An example of a secreted enzyme exerting an anti-apoptotic effect upon a host cell is the production of large amounts of iron-cofactored SOD by the pathogenic mycobacteria. The secretion of iron-cofactored SOD suggested that this enzyme was important to mycobacterial survival and we found its effect to be mediated primarily by inhibition of host cell apoptosis and the infiltration of mononuclear cells to the site of infection. Pathogenic mycobacteria also produce extracellular thioredoxin and extracellular glutamine synthetase (synthase), which are also believed to exert an anti-apoptotic effect [see below]. This illustrates that there may be more than one anti-apoptotic enzyme produced by a bacterium that can be altered to render a pro-apoptotic effect. In contrast, some of the enzymes listed above may not render a pro-apoptotic phenotype for specific bacterial species. For example, the zinc-copper superoxide dismutase of *M. tuberculosis* is not extracellular and its inactivation did not affect the pathogenicity of *M. tuberculosis* when null mutants were created and tested (Dussurget et al., 2001).

Anti-apoptotic enzymes of bacteria do not have to exhibit a direct anti-apoptotic effect upon their host cell, but may instead be involved in either the synthesis or maintenance of a anti-apoptotic factor that is not an enzyme but that is secreted by the microbe. For example, *Salmonella* species secrete large amounts of extracellular glutathione, which is a reducing agent that affects the redox status of a cell and is composed of the three amino acids glycine, glutamine, and cysteine. This suggests that reducing the activity of glutathione reductase (glutaredoxin), which helps to maintain glutathione in a reduced form, or glutamine synthetase, which is involved in the biosynthesis of glutamine that is a component of glutathione, would render a pro-apoptotic phenotype upon *Salmonella* species, thereby enhancing antigen presentation.

Step 2: Generating Mutants of Essential Enzymes

In the steps of mutating the enzyme-encoding genes or replacing the wild-type gene with a mutated gene or homologous gene, standard molecular methods are used. Examples of these methods are described below.

A person of skill can then make mutants of the essential enzyme by altering its primary structure or by modifying the nucleotides that encode it or regulate its transcription and translation. These mutations should produce a reduction in enzymatic activity by incremental reduction in enzymatic efficiency, reductions in enzyme production, or in some circumstances, changes in enzyme localization. In some circumstances the virulent microbe's enzyme can be replaced by a less efficient enzyme from another species, rather than by introducing mutations into the enzyme of the virulent microbe. These mutants can exhibit enzymatic activity that is only, for example, 95%, 90%, 85%, 80%, 75%, 70%, 65%, 60%, 55%, 50%, 45%, 40%, 35%, 30%, 25%, 20%, 15%, 10%, 5%, 2%, etc. of the activity of the parent, natural enzyme. A series of mutant enzymes can be produced that have activities that fall within this range of reduction in activity.

Reducing The Amount of the Native Enzyme

The activity of the enzyme can be reduced by reducing the amount of the enzyme produced by the microbe. In one embodiment, the amount of enzyme produced by the microbe is reduced by altering a promoter in the microbe to decrease expression of a nucleic acid that encodes the enzyme, thereby reducing the amount of enzyme produced by the microbe. Mutations can be introduced into a naturally occurring promoter to make it less efficient. For example, one skilled in the art will appreciate that mutations that affect the −35 or −10 ribosomal binding sites, such that ribosomal binding and transcription of the gene is diminished relative to that exhibited with the normal promoter can be introduced into the promoter that will diminish bacterial enzyme production. Alternatively, the naturally occurring promoter can be replaced with a weaker promoter from the same microbe, or from a different microbial species or with a promoter for another microbial factor that is not as well expressed. Those skilled in the art will appreciate that different proteins are expressed to varying degrees by the same bacterium, and that by replacing the promoter of a highly-expressed enzyme with the promoter of a less well expressed protein, that reduced enzyme activity can be achieved.

For example, in *M. tuberculosis*, altering the sodA promoter can cause less expression of the enzyme, SOD. Weaker promoters from *M. tuberculosis* and other Mycobacterial species can be used to replace the natural SOD promoter. Thus, altering a promoter can cause decreased expression of SOD in a bacterium, thereby producing a modified bacterium with less likelihood of full survival in vivo.

In another embodiment of the present invention, the amount of enzyme produced by the microbe can be reduced by replacing codons in a naturally occurring nucleic acid that encodes the enzyme, with codons that reduce the efficiency of translation of mRNA for the enzyme. It is well known that bacterial species use some codons more efficiently than others. Thus, a person of skill in the art can replace the efficiently used codons with less efficiently used codons so that translation of an altered mRNA for an essential enzyme becomes less efficient. Thus, by reducing the efficiency of translation of the mRNA, less enzyme is produced, without altering the amino acid sequence of the enzyme. For example, with leucine (Leu): the UUG, CUC, and CUG codons are used relatively frequently whereas the UUA, CUC, and CUA codons are used infrequently. By replacing a large number of the high-usage leucine codons throughout the SOD gene with low-usage leucine codons, the efficiency of translation can be reduced and thereby the quantitative production of *M. tuberculosis* SOD will be diminished, without changing the primary structure of SOD. Codon usage tables are available for *M. tuberculosis* and other microbes to help guide codon substitutions. Similar substitutions could be made for other amino acids. Another strategy to reduce translation is to put several low-usage codons in a row within the open reading frame. There is a strong retarding effect upon translation when low-usage codons are placed side-by-side (Lakey et al., 2000). Presumably this causes ribosomal pausing that leads to disassociation between the mRNA transcript and the ribosome, thereby affecting translation and causing reduced gene product formation. Accordingly, the insertion of low-usage codons in a row (2, 3, 4, etc.) early in the SOD reading frame achieves incremental decreases in translational efficiency.

The success of this strategy in improving the synthesis of *M. tuberculosis* gene products including SOD in *E. coli* has been shown (Lakey, Voladri, Edwards, Hager, Samten, Wallis, Barnes, and Kernodle, 2000). Reducing the formation of a gene product by the same strategy is highly feasible. Differences in the transcription/translation of the codon-altered genes in a mycobacterial background are determined by expressing each mutant SOD gene in *M. vaccae*, as described for the wild-type *M. tuberculosis* allele (Zhang et al., 1992; Cooper et al., 1994) and assaying for the relative amount of *M. tuberculosis* SOD tetramers on agarose gel assays. This should provide a comparative ranking of the expression of the various mutant SOD alleles and the amount of translated SOD that can be used to select which mutant alleles to use for allelic replacement in *M. tuberculosis*.

Reducing the Efficiency of the Enzyme

In another embodiment of the present invention, the activity of an enzyme, for example, superoxide dismutase (SOD), can be reduced by reducing the efficiency of the enzyme. For example, the efficiency of the enzyme can be reduced by altering a naturally occurring nucleic acid that encodes the enzyme, comprising deleting, inserting and/or substituting codons in the naturally occurring nucleic acid, wherein the nucleic acid with the deletion, insertion or substitution encodes an enzyme with reduced efficiency. There are PCR-based methods known to a person of skill in the art for rapidly making deletion, insertion and substitution mutants of an enzyme (Ho et al., 1989). Other genetic strategies for remodeling of enzymes involving internal deletions of portions of the enzyme have been described (Ostermeier, Nixon, and Benkovic, 1999).

X-ray crystallographic data, either directly determined from *M. tuberculosis* enzymes, or from highly homologous enzymes (as determined by amino acid sequence alignment with the *M. tuberculosis* enzyme) from other species are available for many of these enzymes. Such data can be an invaluable guide for guiding mutations to introduce during TIA. Knowledge of the crystal structure enables amino acid deletions, insertions, and substitutions to be targeted to regions away from the active site where it is less likely that the alteration will completely inactivate the enzyme. And as practiced in the *M. tuberculosis* SOD example [Example 11, Table 11, and FIGS. 21-22], deleting amino acids in inter-domain regions is expected to be less likely to severely alter the enzyme structure than making changes within a domain.

In the absence of X-ray crystal data to help guide specific amino acid deletions, substitutions, and insertions, the substitution of an amino acid or amino acids of an enzyme to produce a modified enzyme in a microbe having immunogenicity and decreased pathogenicity can be carried out by a systematic approach comprising replacement of each of the amino acids in the enzyme sequentially, starting from the amino terminus of the enzyme. A microbe having an enzyme having a single amino acid substitution and which shows immunogenicity and decreased pathogenicity can be identified, and a second amino acid substitution can be introduced into the amino acid sequence of the singly-substituted enzyme sequentially, starting from the amino terminus of the singly-substituted enzyme. A microbe comprising a doubly-substituted enzyme can then be tested for immunogenicity and attenuated pathogenicity, and those bacteria which show such immunogenicity and attenuated pathogenicity can have further amino acid substitutions made by the systematic, sequential method described herein. Thus, a plurality of bacterial strains can be produced with varying levels of pathogenicity. See Examples 11 & 12, below.

A similar systematic approach comprising deletion of one or more amino acids in the enzyme sequentially, starting from the amino terminus of the enzyme can be utilized to construct deletion mutants. A microbe having an enzyme having a single amino acid deletion and which shows immunogenicity and decreased pathogenicity can be identified, and a second amino acid deletion can be made in the amino acid sequence of the singly-deleted enzyme sequentially, starting from the amino terminus of the singly-deleted enzyme. A microbe comprising a doubly-deleted enzyme can then be tested for immunogenicity and attenuated pathogenicity, and those bacteria which show such immunogenicity and attenuated pathogenicity can have further amino acid deletions made by the systematic, sequential method described herein. Thus, a plurality of bacterial strains can be produced with varying levels of attenuation [see Examples 11 & 12, Table 11, and FIG. 22].

Altering the Localization of the Enzyme

In another embodiment of the present invention, the activity of the enzyme can be reduced by altering the localization of the enzyme, whereby altering the localization of the enzyme reduces activity of the enzyme. With some enzymes, export from the cell is mediated by a leader peptide, which if altered, may interfere with the export of the enzyme from the microbe to the extracellular environment. Thus, altering a leader peptide in an enzyme can alter the localization of the enzyme, thereby reducing the activity of the enzyme. For example, substituting one or more amino acids close to the cleavage site in the pro-enzyme, and in particular the two amino acids that comprise the cleavage site, can alter the localization of the enzyme. A microbial protease normally acts on the cleavage site to release the mature form of the enzyme. Thus, substituting the amino acids alters the cleavage site so that it is not recognized by the protease; therefore, cleavage does not occur; and the mature enzyme is produced but cannot be released to its proper location.

Substituting the Enzyme with a Similar Enzyme

In another embodiment of the present invention, the efficiency of the enzyme can be reduced by substituting from another bacterial species a nucleic acid that encodes a less efficient version of the enzyme for a naturally occurring nucleic acid.

For example, SOD is a ubiquitous enzyme produced by a large number of prokaryotes and eukaryotes. The iron-manganese SOD gene from several Mycobacterial species including M. avium (Escuyer et al., 1996), M. smegmatis (Harth and Horwitz, 1999), and M. fortuitum (Menendez et al., 1995) along with the allele from unrelated bacterial species including E. coli and S. aureus can be cloned directly or amplified by PCR to provide DNA for allelic replacement. The latter two differ markedly in G&C % (guanosine & cytosine) from M. tuberculosis (about 50%, 28%, and 65% respectively) as well as codon usage, whereas the former three are highly homologous to M. tuberculosis SOD except they each use manganese as the metal co-factor rather than iron. Only one of these, the SOD of M. avium, is secreted to any significant degree (Escuyer, Haddad, Frehel, and Berche, 1996), whereas the others are intracellular or membrane-associated. The differences between these enzymes in metal cofactor, translational efficiency secondary to codon usage, and localization produce the differences in the activity of the respective enzymes. These differences in activity are used to advantage in the present method.

Step 3: Replacing the Native Enzyme with a Mutant Allele

The gene replacement step of the present invention involves standard nucleic acid manipulations well known to the skilled artisan. "Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art. Moreover, a nucleic acid can be an antisense nucleic acid.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. A "cell" can be a cell from any organism including, but not limited to, a bacterium. The isolation of nucleic acids can therefore be accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the enzyme encoded by the nucleic acid are maintained. However, it is contemplated that modifications of the nucleic acid encoding an enzyme of the present invention will decrease the activity of the enzyme.

The nucleic acid containing a promoter or other regulatory sequence and/or encoding an enzyme of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding an enzyme to be modified by this invention.

The nucleic acid sequences can be expressed in hosts after the sequences have been positioned to ensure the functioning of an expression control sequence. In most applications of TIA, allelic replacement vectors will be used to replace the gene encoding the native enzyme on the bacterial chromosome with the mutant form of the gene. The appropriate vectors and techniques to use with specific bacterial species are known to one skilled in the art. For example, in *M. tuberculosis*, a system for rendering unmarked replacement of alleles that does not leave antibiotic resistance genes in the final strain has been described (Parish and Stoker, 2000). Alternatively, the mutant gene can be inserted into the chromosome via a phage integration site and then the gene encoding the native form of the enzyme inactivated using allelic inactivation techniques, such that only the mutant gene is expressed in the final strain. Or the gene encoding the native form of the enzyme can first be inactivated using allelic inactivation techniques and then the mutant gene introduced back into the microbe on a plasmid vector.

The nucleic acid of this invention can be in a cell, which can be a cell expressing the nucleic acid whereby an enzyme of this invention is produced in the cell. In addition, the vector of this invention can be in a cell, which can be a cell expressing the nucleic acid of the vector whereby an enzyme of this invention is produced in the cell.

A nucleic acid encoding an enzyme of this invention can be any nucleic acid that functionally encodes an enzyme of this invention. To functionally encode an enzyme (i.e., allow the nucleic acids to be expressed), a nucleic acid of this invention can include, for example, expression control sequences, such as an origin of replication, a promoter, an enhancer and necessary information processing sites, such as ribosome binding sites, RNA splice sites, and transcriptional terminator sequences.

A nucleic acid encoding a selected enzyme can readily be determined based upon the genetic code for the amino acid sequence of the selected enzyme and many nucleic acids will encode any selected enzyme. Modifications in the nucleic acid sequence encoding the enzyme are also contemplated. Such methods are standard in the art. The nucleic acid of this invention can be generated by means standard in the art, such as by recombinant nucleic acid techniques and by synthetic nucleic acid synthesis or in vitro enzymatic synthesis.

Step 4: Identifying Mutants to Use as Vaccine

As described above, the gene encoding the naturally occurring enzyme in a virulent microbe is replaced with one or more of the mutated genes or homologous genes to produce a microbe with attenuated virulence. A mutant that achieves the right balance between attenuation of the microbe's pathogenicity and its immunogenicity for use as a vaccine strain can then be identified.

As used herein, "attenuated," means having a reduced ability to cause disease. Thus, attenuation refers to any reduction in the ability of the mutant strain constructed using TIA to cause disease compared to the parent microbe from which the mutant was derived. Attenuation of a microbe is generally evidenced by one or more of three characteristics.

First, there may be diminished (or absent) mortality among animals infected with the attenuated mutant compared to the parent virulent strain.

Figure 15:
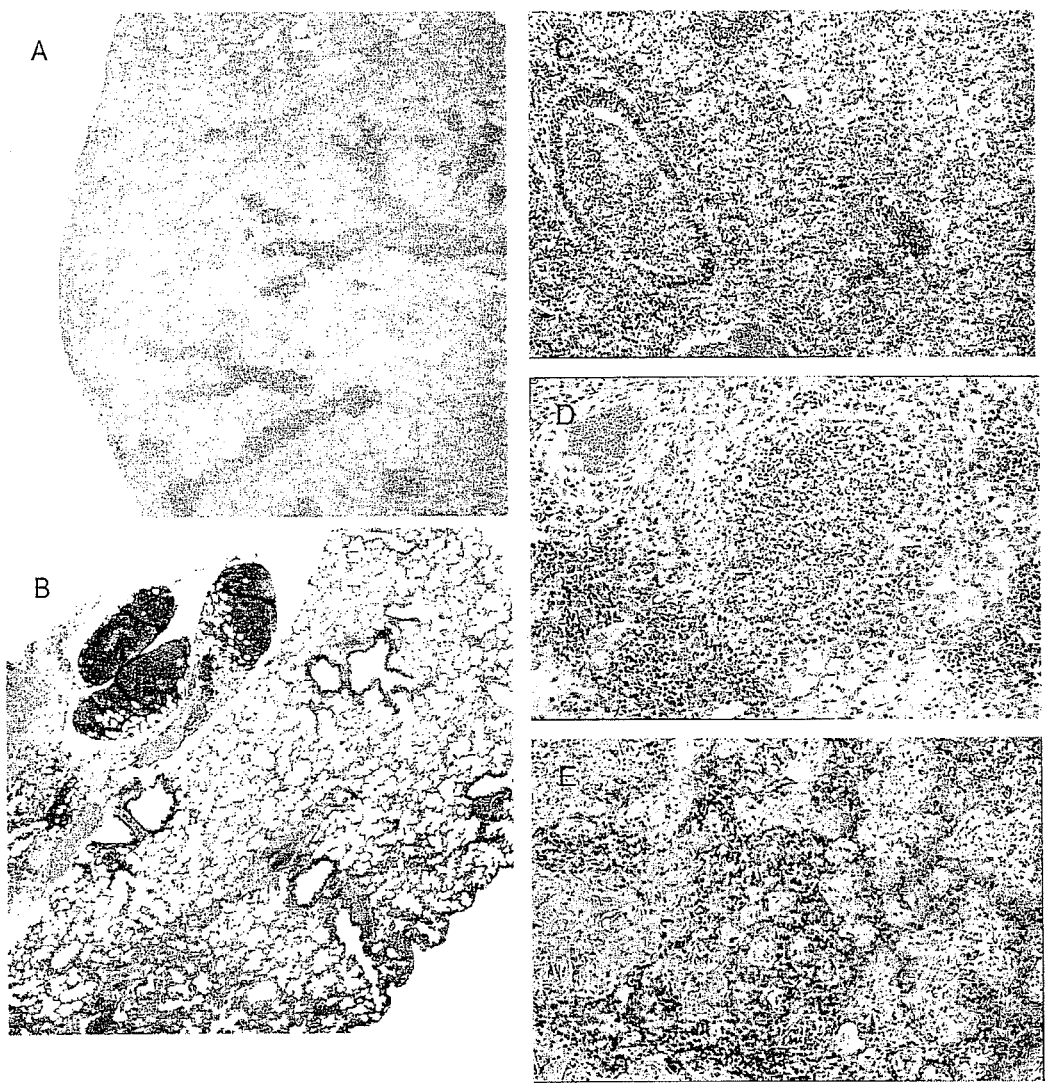

Second, attenuation will usually be reflected in a more rapid fall in the number of mutant microbes surviving over time when organs from infected animals are homogenized and the microbes enumerated compared to the kinetics of survival of the parent strain [for example, FIG. 6]. Depending upon the nature of the enzyme target, the fall in the number of viable organisms of the mutant strain compared to the parent strain may be exhibited early or not become apparent until a host immune response has developed. For example, reducing the activity of an essential biosynthetic enzyme might have an immediate impact on the ability of the microbe to replicate in vivo, such that microbial counts of the mutant are less than those of the parent strain almost immediately after inoculation and progressively fall over time. In contrast, altering the expression of an enzyme associated with protection against a host immune response, such as SOD, may not cause a progressive reduction in counts of some microbial species from the onset, but will become evident only after a strong host immune response has developed. For example, note in FIG. 6 that the SOD-diminished strains exhibited some growth in vivo between day 1 and day 14 but uniformly had fallen to lower organ counts by day 28, and in FIG. 10 that the number of viable SOD-diminished bacilli continued to fall for at least 17 months post-infection. Based upon the demonstration of a marked increase in apoptosis by day 28 [FIG. 8] along with the increase in the proportion of CD8+ T-cells [FIG. 15, Tables 4-6] and their localization in the interstitial spaces [FIG. 25], this continued fall in bacterial counts appears to be related to the development of a host cellular immune response involving cytotoxic T-lymphocytes during the $3^{rd}$ and $4^{th}$ weeks of infection. So, although in this case it is clear that diminishing SOD had an immediate impact upon the survival of *M. tuberculosis* in vivo, it also impaired the ability of the microbe to prevent the development of strong adaptive cellular immune responses and protect itself against such responses. Attenuation achieved by TEA may result in the complete eradication of the microbe; however, this is not necessary and in some circumstances the mutant strain will persist indefinitely. For example, viable SOD-diminished H37Rv could still be detected 17 months after infection, however it survived in lower numbers than the current vaccine strain for tuberculosis, BCG [see FIG. 10], which has a well-established record of safety.

Third, attenuation of the mutant strain will also generally be manifested by a reduced inflammatory response over time and/or less damage to the host organs that the microbe normally infects. Gross and histopathologic examination of organs from animals infected with the mutant and parent strains will generally be useful in making these determinations [see FIGS. 11 and 12]. Differences in organ damage may not be evident initially, as an initial host inflammatory response may be needed to limit in vivo growth of the attenuated microbe.

Additional indicators can be used to verify that attenuated microbes have pro-apoptotic qualities that enhance cellular immune responses. An early clue is the observation that a greater proportion of the host cells in which the vaccine strain typically reside (e.g., macrophages) undergo apoptosis in the first few days post-infection. If the mechanism of rendering a vaccine strain pro-apoptotic also alters the host cell redox status, the vaccine strain may also induce the rapid infiltration of mononuclear cells, including monocytes and dendritic cells, to an organ or tissue where the vaccine strain was delivered [see FIG. 7 and FIG. 23]. In these circumstances, some of the infiltrating cells may undergo apoptosis. This is illustrated in FIG. 8 and explained in FIG. 19, where the reduction of iron-cofactored SOD production by *M. tuberculosis* is believed to have altered the redox status of the macrophage such that activation of nuclear factor-kappa B (NF-kappaB) and possibly activating protein-1 (AP-1) was favored with the result of increased cytokine production that led to increased infiltration of inflammatory cells into the lung. In essence, the combination of inflammatory cell infiltration and apoptosis of host cells sets the stage for apoptosis-associated antigen cross-presentation to occur in vivo. Accordingly, attenuated mutants that induce both cell infiltration and apoptosis are likely to be the most effective in inducing strong cellular immune responses, and the construction of mutants that alter host cell redox status to favor both NF-kappaB activation and apoptosis are especially preferred.

Another indicator that an attenuated mutant has pro-apoptotic qualities is a redistribution of the lymphocytes towards increased CD8+ T-cell responses. In vitro studies show that dendritic cells acquire microbial antigens from apoptotic macrophages and induce strong CD8+ cytotoxic T-lymphocyte responses (Albert, Sauter, and Bhardwaj, 1998; Yrlid and Wick, 2000). An increased percentage of CD8+ T-cells following vaccination with SOD-diminished *M. tuberculosis* compared to vaccination with BCG was consistently observed [FIG. 16 and Tables 3-6], and similar differences were noted when SOD-diminished BCG and BCG were compared [Table 10]. CD8+ cytotoxic T-lymphocytes generally work by inducing apoptosis, killing the infected cell as a means to control the pathogen within them. An enhancement of apoptosis was evident by four weeks post-vaccination with the present SOD-diminished vaccine strain and coincided with increased infiltration of inflammatory cells into the lung interstitium [FIG. 8], and large numbers of CD8+ T-cells have been observed in the interstium of lungs of mice vaccinated with BVV [FIG. 24 and FIG. 25]. This shows that vaccination had produced enhanced cytotoxic T-lymphocyte activity, a highly desired response.

As used herein, "immunogenicity" means the ability of an attenuated microbe to generate an immune response in a host, for example, an immune response that reduces the severity of illness when the host is subsequently challenged with a virulent microbe of the same or closely related species.

Animal models are valuable in assessing immunogenicity, as shown in FIG. 13, where both BCG and SOD-diminished H37Rv provided strong protection against challenge with a virulent *M. tuberculosis* strain compared to unvaccinated animals. Correlates of immunogenicity and protective immunity can often be measured in vitro. The appropriate test to measure immunogenicity in vitro will depend upon the pathogen and the type of host immune mechanism that is normally involved in controlling the microbe in vivo. However, as this invention teaches how to enhance cellular immunity by altering microbes to facilitate apoptosis-associated antigen cross-presentation in vivo, assays of T-cell function are emphasized and are well known to those skilled in the art. For example, with *M. tuberculosis*, in vitro assays comparing the magnitude of interferon gamma production after exposure to *M. tuberculosis*-specific antigens along with determinations of the number of T-lympocytes capable of reacting with *M. tuberculosis*-specific antigens (by Elispot or FACS assessment of interferon-gamma expression) may correlate with vaccine efficacy and can help determine whether vaccination with a specific vaccine candidate induces beneficial T-cell responses. Also as exemplified in FIGS. 16, 24, 25, as well as Tables 4-6 and 10, FACS and tissue immunohistochemistry can be used to demonstrate CD8+ T-cell responses post-vaccination. Such in vitro assays are especially useful in comparing vaccine candidates in humans or other subjects in which challenge experiments with virulent bacteria cannot be done to directly measure vaccine efficacy. Thus, the invention provides guidance as to the selection of attenuated microbes with the right balance of attenuation and immunogenicity, and which induce the desired cellular immune responses. This selection can be tailored to the particular patient population as needed.

The microbe attenuated by the present methods can be a bacterium, protozoan, virus, or fungus. When the microbe is a bacterium, the bacterium can be, but is not limited to, for example, a *Mycobacterium* species. Examples of species of *Mycobacterium* include, but are not limited to, *M. tuberculosis, M. bovis, M. bovis* strain BCG including BCG substrains, *M. avium, M. intracellulare, M. africanum, M. kansasii, M. marinum, M. ulcerans* and *M. paratuberculosis*. It could also be a *Nocardia* species, including *Nocardia asteroides* or *Nocardia farcinica*. The construction of SOD-diminished mutants of these species can achieve both attenuation and confer the pro-apoptotic quality that enhances the development of strong cellular immune responses in a manner analogous to the present SOD-diminished *M. tuberculosis* vaccine and the present SOD-diminished BCG vaccine, as secretion of iron-manganese SOD is a common and distinctive attribute of many of the pathogenic species of mycobacteria (Raynaud et al., 1998) and *Nocardia*. Accordingly, SOD-diminished vaccines of these other mycobacterial species and *Nocardia* are expected to also be highly effective vaccine strains. Examples of other obligate and facultative intracellular bacterial species contemplated within the present invention include, but are not limited to, *Legionella pneumophila*, other *Legionella* species, *Salmonella typhi*, other *Salmonella* species, *Shigella* species, *Listeria monocytogenes, Staphylococcus aureus, Staphylococcus epidermidis, Bacteroides fragilis*, other *Bacteroides* species, *Chlamydia pneumoniae, Chlamydia trachomatis, Chlamydia psittaci, Coxiella burnetii*, other *Rickettsial* species, and *Ehrlichia* species.

Moreover, bacteria that cause diseases in livestock, animals and pets can be the targets of the methods of the present invention. Examples of veterinary bacterial pathogens include, but are not limited to, *Brucella abortus* and other *Brucella* species, *Yersinia pestis, Pasteurella haemolytica, Pasteurella multocida* and other *Pasteurella* species, *Actinobacillus pleuropneumomia, Cowdria ruminantium, Mycobacterium avium* subspecies *paratuberculosis*, and *Listeria ivanovii*.

Other intracellular microbes such as protozoa and fungi that exert an anti-apoptotic effect upon their host cell are likely to become both attenuated and pro-apototic, and therefore useful as vaccine strains, when the activity of a microbial enzyme that primarily mediates the anti-apoptotic effect is reduced. Thus, the invention provides a method of modifying a protozoan to enhance the immunogenicity of the protozoan, comprising reducing the activity of an anti-apoptotic enzyme produced by the protozoan, whereby the protozoan has enhanced immunogenicity in a subject and a method of modifying a fungus to enhance the immunogenicity of the fungus, comprising reducing the activity of an anti-apoptotic enzyme produced by the fungus, whereby the fungus has enhanced immunogenicity in a subject. Examples of protozoan and fungal species contemplated within the present invention include, but are not limited to, *Plasmodium falciparum*, other *Plasmodium* species, *Toxoplasma gondii, Pneumocystis carinii, Trypanosoma cruzi*, other trypanosomal species, *Leishmania donovani*, other *Leishmania* species, *Theileria annulata*, other *Theileria* species, *Eimeria tenella*, other *Eimeria* species, *Histoplasma capsulatum, Cryptococcus neoformans, Blastomyces dennatitidis, Coccidioides immitis, Paracoccidioides brasiliensis, Pneunzocystis carinii, Penicillium marneffei*, and *Candida* species. Methods have been described for creating recombinant and attenuated mutants of protozoa and yeast species, and are known to a person of skill in the art. For example, transfection techniques and vectors for insertional mutagenesis and the expression of heterologous antigens have been described in *Toxoplasma gondii* (Chiang et al., 1999; Charest et al., 2000). As an iron-cofactored SOD of *Toxoplasma gondii* has been described (Odberg-Ferragut et al., 2000), such vectors and methods can be used to reduce its production, or that of another anti-apoptotic enzyme, by using allelic inactivation, antisense techniques, or TIA. Similarly, *Trypanosoma* and *Leishmania* species are susceptible to transformation and chromosomal integration of DNA (Brooks et al., 2000; Dumas et al., 1997), thereby enabling similar manipulations. Methods for performing genetic manipulations in fungal pathogens have also become recently available (Retallack et al., 1999; Woods, Heinecke, and Goldman, 1998; Varma and Kwon-Chung, 2000; Enloe, Diamond, and Mitchell, 2000; Wilson et al., 2000). A protozoan made in accordance with the method of the invention is provided, as is a fungus made in accordance with the method of invention.

Viral pathogens might also be modified to become pro-apoptotic, yet viruses differ from most of the microbes cited above in that viral replication in the cytoplasm of their host cells already provides a mechanism for viral antigens to be presented via MHC Class I pathways to induce strong CD8+ T-cell responses. Accordingly, whereas reduction in the activity of a viral anti-apopototic enzyme might be expected to enhance CD8+ T-cell responses, the effect may not be as profound as that exhibited by SOD-diminished *M. tuberculosis*. However, TIA can be employed to introduce mutations in essential enzymes resulting in incremental differences in pathogenicity, thereby facilitating the creation of an appropriately attenuated mutant that achieves the right balance between attenuation and immunogenicity. Techniques for performing genetic manipulations have been described for many viral species (Heider et al., 2002; Durbin et al., 1999). The molecular manipulations required to reduce the activity of an essential or anti-apoptotic viral enzyme are routine. Thus, a virus modified according to the teaching of the application is provided.

Most of the bacteria (including *chlamydia, rickettsia*, and *ehrlichia*), protozoa, and fungi identified above are either obligate or facultative intracellular pathogens or reside within the phagolysosome and do not have access to the cytoplasm of the cell for MHC Class I antigen presentation. For these pathogens, apoptosis-associated cross-presentation might provide the only mechanism for inducing strong CD8+ T-cell responses. Although rendering a pro-apoptotic quality upon extracellular pathogens that are controlled predominantly by neutrophils, antibodies, complement, and other components of the immune system rather than macrophages and lymphocytes is not expected to have the same immune-enhancing effect that it will have for the organisms listed above, TIA can be used with extracellular bacteria to fine-tune their level of attenuation and construct novel live-attenuated vaccines. Examples of bacterial species upon which TIA can be practiced that are contemplated within the present invention include, but are not limited to, all of the bacteria listed above, *Streptococcus pyogenes, Streptococcus pneumoniae, Streptococcus agalactiae, Bacillus anthracis, Escherichia coli, Vibrio cholerae, Campylobacter* species, *Neiserria meningitidis, Neiserria gonorrhea, Pseudomonas* species, and *Haemophilus influenzae*. TIA can also be used to fine-tune the level of attenuation of viruses.

The present invention thus provides a method of attenuating a microbe, whereby the microbe retains the full repertoire of antigens that stimulate a host immune response, but loses pathogenicity in a subject, comprising reducing the activity of an enzyme produced by the microbe.

The present invention provides a microbe attenuated according to the methods described in this application. Specifically, the present invention provides a microbe which retains or increases immunogenicity but loses or reduces pathogenicity in a subject, wherein the microbe has a modified enzyme with reduced activity, compared to the level of activity of a naturally occurring enzyme. The microbe can be a bacterium, protozoan, virus, or fungus.

A method of modifying a microbe to enhance the immunogenicity of the microbe is provided, comprising reducing the activity of an anti-apoptotic enzyme produced by the microbe, whereby the bacterium has enhanced immunogenicity in a subject. Thus, also provided is an intracellular microbe, modified to reduce the activity of an anti-apoptotic enzyme of the microbe.

The invention also provides a method of modifying an attenuated microbe to enhance the immunogenicity of the attenuated microbe, comprising reducing the activity of an anti-apoptotic enzyme produced by the attenuated microbe, whereby the attenuated bacterium has enhanced immunogenicity in a subject. Thus, also provided is an attenuated intracellular microbe, further modified to reduce the activity of an anti-apoptotic enzyme of the microbe.

As noted above, the microbe can be any microbe described herein. The microbe can be an intracellular pathogen or an obligate intracellular pathogen. The invention also contemplates an embodiment of the method and the microbe in which the bacterium in not *Yersinia enterocolitica*.

Thus, a specific embodiment of the invention provides a live vaccine against tuberculosis, derived by diminishing the activity of iron-manganese superoxide dismutase (SOD) in a strain of *M. tuberculosis*. Reducing SOD produces a mutant mycobacterium that grows slowly, is highly susceptible to killing by hydrogen peroxide, and is attenuated in its pathogenicity in mammalian hosts. SOD-diminished *M. tuberculosis* complex strains can be produced by using antisense techniques or targeted incremental attenuation as described herein. This invention anticipates the possibility that it may eventually be feasible to produce SOD-deficient mutants of *M. tuberculosis* complex strains by allelic inactivation if an exogenous SOD-mimetic or anti-oxidant that permits in vitro growth of the SOD-deficient mutant is identified.

Examples of the microbes made by deletion mutation include, but are not limited to the following: a mutant *M. tuberculosis* in which glutamic acid is deleted at position 54 of superoxide dismutase; a mutant *M. tuberculosis* in which glycine is deleted at position 88 of superoxide dismutase; a mutant *M. tuberculosis* in which glycine is deleted at positions 87 and 88 of superoxide dismutase; a mutant *M. tuberculosis* in which glycine is deleted at position 134 of superoxide dismutase; a mutant *M. tuberculosis* in which proline is deleted at position 150 of superoxide dismutase; and a mutant *M. tuberculosis* in which valine is deleted at position 184 of superoxide dismutase.

Examples of the microbes made by substitution mutation include, but are not limited to the following: a mutant *M. tuberculosis* in which lysine is substituted for histidine at position 28 of superoxide dismutase; a mutant *M. tuberculosis* in which lysine is substituted for histidine at position 76 of superoxide dismutase; a mutant *M. tuberculosis* in which lysine is substituted for histidine at position 145 of superoxide dismutase; and a mutant *M. tuberculosis* in which lysine is substituted for histidine at position 164 of superoxide dismutase.

The present invention also provides mutants of *M. tuberculosis* complex strains in which antisense techniques have been used to diminish the production of SOD, thioredoxin, and ClpC Atpase, thereby attenuating the strain. The invention also provides for these or similar antisense plasmid constructs to be introduced into strains of *M. tuberculosis* and *M. bovis* which are already attenuated, including BCG. Therefore, a further example of a bacterium of the invention is a BCG strain that also expresses antisense-SOD (AS-SOD).

This has the advantage over SOD-diminished *M. tuberculosis* in that BCG is already sufficiently safe to administer to man, while the AS-SOD construct confers advantages in antigen processing. Other methods of reducing the activity of SOD or other enzymes involved in protection against reactive oxygen species or reactive nitrogen species can be used in the already attenuated strains.

The present invention further provides the attenuated microbes of the invention, further expressing a heterologous antigen. The pro-apoptotic, attenuated bacteria of the present invention are optionally capable of expressing one or more heterologous antigens. As a specific example, heterologous antigens are expressed in SOD-diminished BCG bacterium of the invention. Live-attenuated vaccines have the potential to serve as vectors for the expression of heterologous antigens from other pathogenic species (Dougan et al, U.S. Pat. No. 5,980,907; Bloom et al, U.S. Pat. No. 5,504,005). Thus, the microbes of the present invention having a reduction in the expression or activity of an anti-apoptotic or essential enzyme can further be modified to express an antigen from a different microbe. Such antigens may be from viral, bacterial, protozoal or fungal microorganisms. The recombinant pro-apoptotic microorganisms then form the basis of a bi- or multivalent vaccine. In this manner, multiple pathogens can be targeted by a single vaccine strain. The invention provides a method of making a multivalent vaccine comprising transforming the pro-apoptotic microbe of the invention a nucleic acid encoding a heterologous antigen. For example, antigens of measles virus containing immunodominant CD4+ and CD8+ epitopes could be expressed in SOD-diminished BCG, with expression achieved by stably integrating DNA encoding the measles antigen of interest into genomic DNA of the pro-apoptotic BCG of the invention using techniques taught by Bloom et al (U.S. Pat. No. 5,504,005, which is hereby incorporated by reference in its entirety). Alternatively, the gene encoding the antigen could be expressed on a plasmid vector, for example, behind the promoter of the 65 kDa heat-shock protein of pHV203 using standard techniques for expressing recombinant antigens that are well-known to those skilled in the art. A recombinant pro-apoptotic BCG vaccine expressing measles antigens could replace regular BCG as a vaccine for administration at birth in developing countries with a high incidence of infant mortality from measles. The recombinant vaccine stimulates cellular immune responses to measles antigens that would protect the infant in the first few months of life when mortality from measles is the greatest. Recombinant pro-apoptotic BCG expressing measles antigens have advantages over the current live-attenuated measles vaccines, as the presence of maternal antibodies interferes with vaccination before 6 months of age, leaving the infant susceptible to measles during a period of life when they are at high risk of dying from measles. Instead, recombinant pro-apoptotic BCG expressing measles antigens will not be inactivated by maternal antibodies, and can induce protective cellular immune responses at an earlier point in life. Other heterologous antigens of infectious pathogens contemplated by this invention include, but are not limited to, antigens of malaria sporozoites, antigens of malaria merozoites, human immunodeficiency virus antigens, influenza virus antigens, and *leishmania* antigens. Also, the microbes of the present invention can further be modified to express cancer antigens for use as immunotherapy against malignant neoplasms. Heterologous cancer antigens contemplated by this invention include, but are not limited to, melanoma-melanocyte differentiation antigens (MART-1, gp100, tyrosinase and tyrosinase related proteins-1 and -2), cancer-testes antigens (MAGE-1, -2, -3, -12, BAGE, GAGE), β-catenin, MUM-1, CDK-4, α-fetoprotein, telomerase, G-250, MUC-1, p53, Her-2/neu, and carcinoembryonic antigen.

The present invention also provides a method for producing the enzyme of this invention, comprising producing the cells of this invention which contain the nucleic acids or vectors of this invention as exogenous nucleic acid, culturing the cells under conditions whereby the exogenous nucleic acid in the cell can be expressed and the encoded enzyme can be produced, and isolating the enzyme from the cell. A person of skill in the art can measure the amount of an enzyme produced by a cell modified by the methods of the present invention and compare it to the amount of an enzyme produced by a naturally occurring cell and detect a reduction in the amount of enzyme produced by the modified cell.

The invention provides a method of making a microbial vaccine, comprising reducing the activity of an anti-apoptotic enzyme produced by the microbe, wherein the reduction in the activity of the anti-apoptotic enzyme attenuates the mcrobe, whereby a microbial vaccine is produced.

The invention provides a method of making a microbial vaccine, comprising reducing in an attenuated microbe the activity of an anti-apoptotic enzyme produced by the microbe, whereby a microbial vaccine is produced.

The present invention provides a composition comprising a microbe comprising an enzyme modified by the methods of the present invention. The composition can further comprise a pharmaceutically acceptable carrier or a suitable adjuvant. Such a composition can be used as a vaccine.

The present invention additionally provides a method of producing an immune response in a subject by administering to the subject any of the compositions of this invention, including a composition comprising a pharmaceutically acceptable carrier and a microbe comprising an enzyme necessary for in vivo viability that has been modified according to the methods taught herein. The composition can further comprise a suitable adjuvant, as set forth herein. The subject can be a mammal and is preferably a human.

The present invention provides a method of preventing an infectious disease in a subject, comprising administering to the subject an effective amount of a composition of the present invention. In addition to preventing bacterial diseases, for example, tuberculosis, it is contemplated that the present invention can prevent infectious diseases of fungal, viral and protozoal etiology. The subject can be a mammal and preferably human.

It is contemplated that the above-described compositions of this invention can be administered to a subject or to a cell of a subject to impart a therapeutic benefit or immunity to prevent infection. Thus, the present invention further provides a method of producing an immune response in an immune cell of a subject, comprising contacting the cell with a composition of the present invention, comprising a microbe in which an enzyme necessary for in vivo viability has been modified by any of the methods taught herein. The cell can be in vivo or ex vivo and can be, but is not limited to, an MHC expressing antigen presenting cell, such as a dendritic cell, a macrophage or a monocyte. As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The invention, therefore, provides a method of enhancing the immunogenicity of an attenuated bacterium, comprising reducing the activity of an anti-apoptotic enzyme produced by the bacterium, whereby the bacterium has enhanced immunogenicity in a subject. The bacterium modified by reducing the activity of an anti-apoptotic enzyme can be selected from the group consisting of *M. tuberculosis, M. bovis, M. avium, M. intracellulare, M. africanum, M. kansasii, M. marinum, M. ulcerans, M. paratuberculosis, Legionella pneumophila*, other *Legionella* species, *Salmonella typhi*, other *Salmonella* species, *Shigella* species, *Listeria monocytogenes, Nocardia asteroides, Listeria ivanovii, Brucella abortus*, other *Brucella species*, and *Cowdria ruminantium*. For example, live-attenuated strains of *Salmonella* could be further modified using this invention to enhance their immunogenicity and increase their usefulness as vaccines against *Salmonella* infection and to enhance their ability to induce protective cellular immune responses to heterologous antigens, including antigens from other infectious organisms and cancer antigens. Examples of attenuated *Salmonella* that can be improved by the present pro-apoptotic modification are listed in the following table.

| PAT. No. | | |
|---|---|---|
| 5,843,426 | Miller et al. | *Salmonella* vaccines |
| 5,804,194 | Dougan et al. | Vaccines containing a *salmonella* bacteria attenuated by mutation of the htra gene |
| 5,792,452 | Linde | Live *salmonella* vaccine having an increased stability |
| 5,770,214 | Dougan et al. | Vaccines containing *salmonella* bacteria attenuated by mutations in two genes of the aromatic amino acid biosynthetic pathway |
| 5,733,760 | Lu et al. | *Salmonella* vectors encoding truncated pag fusion protein, method of making, and uses thereof |
| 5,695,983 | Miller et al. | *Salmonella* vaccines |
| 5,580,557 | Kramer | Live, avirulent *salmonella choleraesuis* vaccine used for inducing an immune response in animals |
| 5,527,529 | Dougan et al. | Vaccines comprising attenuated *salmonella* having mutations in the ompr genes |
| 5,436,001 | Kramer | Live, avirulent *Salmonella choleraesuis* vaccine used for inducing an immune response in pigs |
| 5,387,744 | Curtiss, III | Avirulent microbes and uses therefor: *Salmonella typhi* |
| 5,294,441 | Curtiss, III | Avirulent microbes and uses therefor: *salmonella typhi* |
| 5,110,588 | Morona | Composite *salmonella E. coli*, *Vibrio cholerae* vaccine strains |
| 4,764,370 | Fields et al. | Vaccine utilizing an avirulent strain of *Salmonella typhimurium* |
| 4,735,801 | Stocker | Novel non-reverting *salmonella* live vaccines |
| 4,550,081 | Stocker | Non-reverting *salmonella* |
| 4,350,684 | Pardon et al. | Preparation of *Salmonella abortus ovis* strains and vaccine compositions containing them |

The enzyme targeted for this modification can be iron-manganese superoxide dismutase, zinc-copper superoxide dismutase, thioredoxin, thioredoxin reductase, glutathione reductase (glutaredoxin), glutamine synthetase, other thioredoxin-like proteins, other thioredoxin reductase-like proteins, other glutaredoxin-like proteins, other thiol reductases, and other protein disulphide oxidoreductases. Other anti-apoptotic enzymes now known or later identified as anti-apoptotic can also be targeted for reduction in activity according the methods described herein.

The step of reducing the activity of the anti-apoptotic enzyme can comprise transforming the microbe with an antisense nucleic acid that reduces the efficiency of translation of the nucleic acid encoding the anti-apoptotic enzyme. Similarly, the TIA method described herein can be used to reduce activity of the anti-apoptotic enzyme, as can allelic inactivation, which is well known in the art. The step of reducing the activity of an anti-apoptotic enzyme can occur either before or after the bacterium is attenuated by other means. In some cases, reducing the activity of an anti-apoptotic enzyme alone will simultaneously achieve both enhanced antigen presentation and sufficient attenuation, such that additional measures to attenuate the bacterium are not needed.

Although reducing the activity of a microbial anti-apoptotic enzyme that affects the redox status of the host cell is the preferred way to simultaneously achieve a pro-apoptotic effect coupled with the rapid influx of mononuclear cells to the site of infection, other ways to achieve the same effect become obvious in the context of the present invention. Apoptosis is under the control of multiple intracellular factors that either inhibit or activate apoptosis. Similarly, cytokine production that leads to the influx of mononuclear cells is under the control of signaling pathways that cause the activation of NF-kappa B. One skilled in art can create recombinant intracellular bacteria that dually stimulate apoptosis and NF-kappa B activation. For example, recombinant vectors that overexpress the genes encoding bax and IL-1-receptor-associated kinase (IRAK) have been reported to induce apoptosis and the activation of NF-kappa B, respectively (Arafat et al., 2000; Maschera et al., 1999). It is within the teaching of the invention to construct recombinant intracellular bacteria producing one or both factors, thereby achieving the same effect that occurs when the activity of a microbial enzyme is reduced that affects the redox status of the host cell. Thus, the invention provides intracellular microbes modified to contain an expression construct that reduces expression of an anti-apoptotic enzyme and an expression construct that increases expression levels of NF-kappaB and/or a pro-apoptotic factor. The present invention also provides for a microbe having both a reduction in activity of a native anti-apoptotic enzyme and overexpression of a pro-apoptotic factor and/or an NF-kappaB activating factor.

Figure 18:
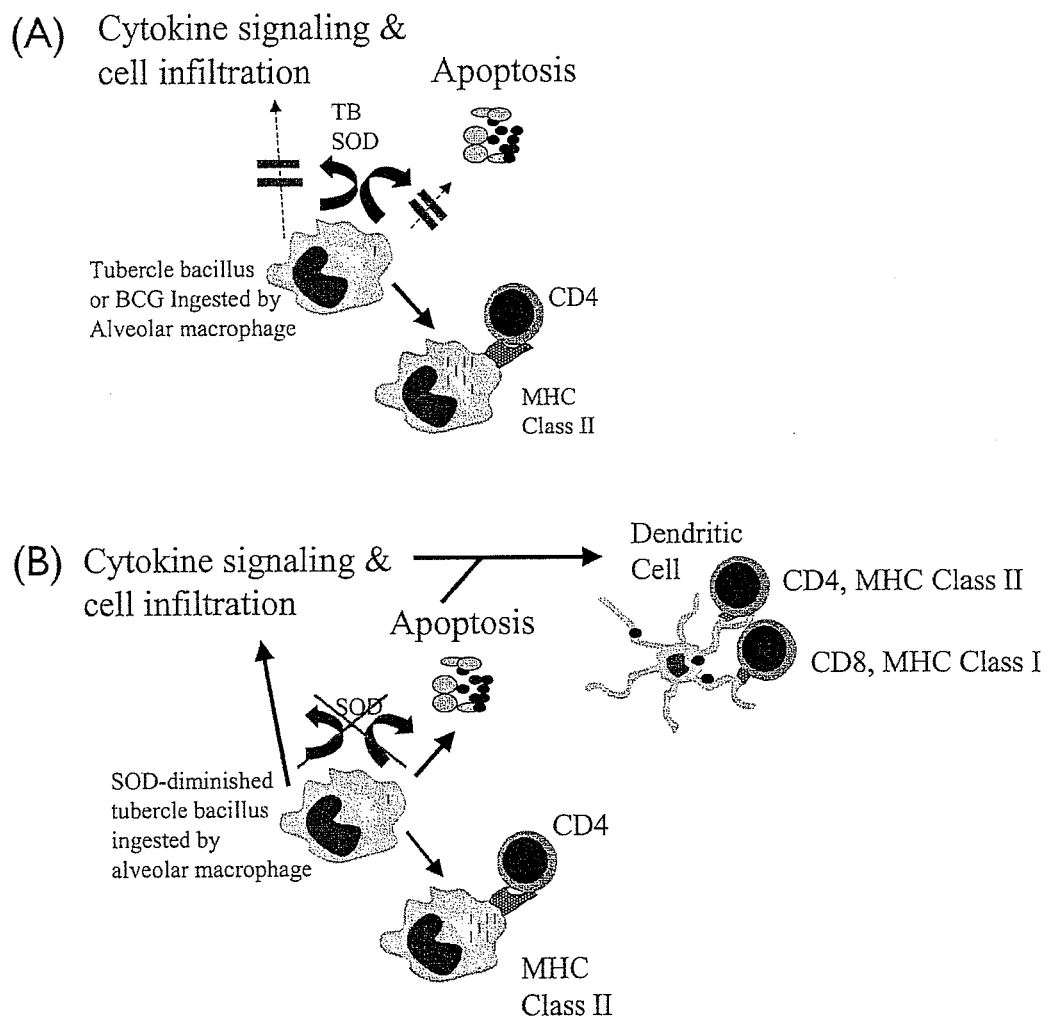
Figure 19:
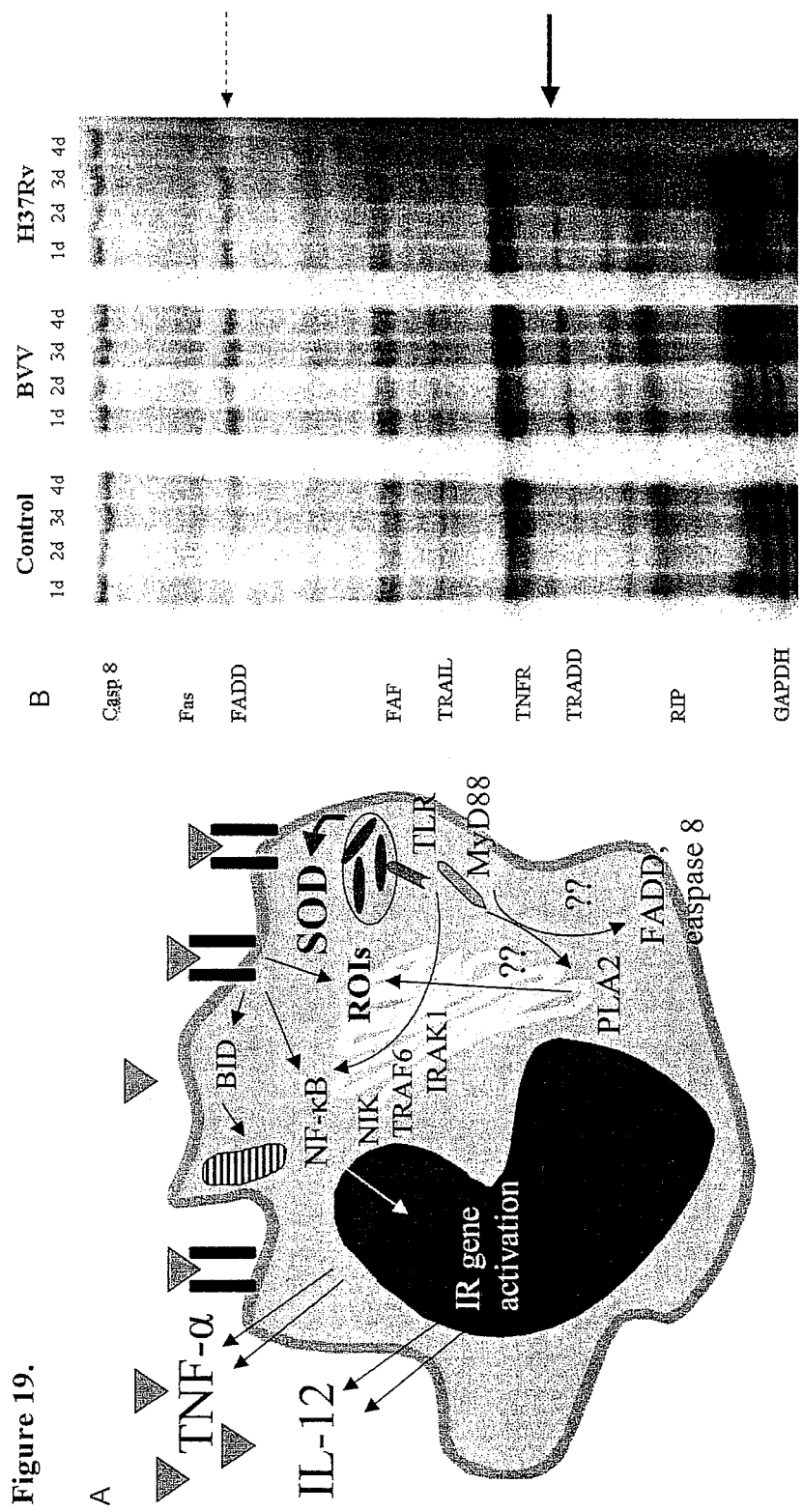

An SOD-diminished *M. tuberculosis* and SOD-diminished BCG vaccines will give the subject greater immunity to tuberculosis than the currently available BCG vaccine. Both *M. tuberculosis* and BCG secrete large amounts of SOD which blocks macrophage apoptosis, thereby allowing the *bacillus* to grow and divide intracellularly. Mycobacterial antigens in phagosomes are usually presented via MHC Class II pathways to CD4+ T cells, which secrete IFN-gamma, thereby activating CD4+ T cells to produce nitric oxide (NO). The host has some capacity to control infection, but the predominant reliance on NO to kill the bacilli also induces necrosis in bystander cells. In contrast, SOD-diminished *M. tuberculosis* and SOD-diminished BCG do not make enough SOD to block macrophage apoptosis. Thus, when macrophages containing bacilli undergo apoptosis, the apoptotic bodies containing mycobacterial antigens are endocytosed by dendritic cells and subsequently presented to CD8+ T-cells via MHC Class I pathways. Thus, in the SOD-diminished bacterium, host containment of *M. tuberculosis* is achieved by a combination of CD4+ and CD8+ responses, achieving greater control with minimal necrosis. This improved antigen processing is illustrated in FIG. 18. The improvement is taken advantage of in the present SOD-diminished BCG strain described in Example 10.

In a preferred method of improving the immunogenicity of a bacterium, the bacterium is a partially- or fully-attenuated strain of *M. tuberculosis* or *M. bovis*, for example BCG, which has been transformed, electroporated, or transduced with an AS-SOD construct, for example, the pHV203-AS-SOD constructs described in Example 1.

In accordance with the method described above for improving immunogenicity, a modified attenuated intracellular bacterium is provided, wherein the activity of an anti-apoptotic enzyme of the pathogen is reduced. The bacterium so modified can be selected from the group consisting of *Mycobacteria* species, BCG, *Legionella* species, *Salmonella* species, *Shigella* species, *Listeria* species, *Brucella* species, and *Cowdria ruminantium*. The targeted enzymes are those described above. In a specific example of the present modified bacterium, the bacterium is a partially- or fully-attenuated strain of *M. tuberculosis* or *M. bovis*, for example BCG, which has been transduced with an AS-SOD construct, for example, the pHV203-AS-SOD constructs described in Example 1.

The compositions of the present invention can be administered in vivo to a subject in need thereof by commonly employed methods for administering compositions in such a way to bring the composition in contact with the population of cells. The compositions of the present invention can be administered orally, parenterally, intramuscularly, transdermally, percutaneously, subcutaneously, extracorporeally, topically or the like, although oral or parenteral administration are typically preferred. It can also be delivered by introduction into the circulation or into body cavities, by ingestion, or by inhalation. The vaccine strain is injected or otherwise delivered to the animal with a pharmaceutically acceptable liquid carrier, that is aqueous or partly aqueous, comprising pyrogen-free water, saline, or buffered solution. For example, an *M. tuberculosis* vaccine would most likely be administered similar to methods used with US BCG Tice strain, percutaneously using a sterile multipuncture disk.

Parenteral administration of the compositions of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intra-articular and intratracheal routes.

The dosage of the composition varies depending on the weight, age, sex, and method of administration. In one embodiment, the dosage of the compound is from $0.5 \times 10^2$ colony-forming units to $5 \times 10^8$ colony-forming units of the viable live-attenuated microbial strain. More preferably, the compound is administered in vivo in an amount of about $1 \times 10^6$ colony-forming units to $5 \times 10^7$ colony-forming units of the viable live-attenuated microbial strain. The dosage can also be adjusted by the individual physician as called for based on the particular circumstances.

The compositions can be administered conventionally as vaccines containing the active composition as a predetermined quantity of active material calculated to produce the desired therapeutic or immunologic effect in association with the required pharmaceutically acceptable carrier or diluent (i.e., carrier or vehicle). By "pharmaceutically acceptable" is meant a material that is not biologically or otherwise undesirable, i.e., the material may be administered to an individual along with the selected composition without causing any undesirable biological effects or interacting in a deleterious manner with any of the other components of the pharmaceutical composition in which it is contained.

Specific Details to Facilitate the Practice of TIA with Preferred Enzymes for Diminishing Microbial Protection Against Host Defenses, and Enhancing Macrophage Apoptosis with Intracellular Pathogens Those skilled in the art will appreciate further benefits of TIA. The advantages of reducing microbial enzymes that are normally involved in protecting the pathogen against killing by reactive oxygen intermediates, reactive nitrogen intermediates, and other stresses the microbe normally encounters in the macrophage have been outlined above. Living organisms have developed mechanisms to protect themselves against oxidative stress, with enzymes such as catalase, superoxide dismutase, and various hydroperoxidases, small proteins like thioredoxin and glutaredoxin, and molecules such as glutathione. Similarly, reactive nitrogen intermediates that are toxic to intracellular pathogens can be generated by macrophages and other host cells, and these substances interact with reactive oxygen intermediates to produce additional toxic molecules such as peroxynitrite. Accordingly, various nitric oxide reductases, peroxynitrite reductases including alkylhydroperoxidase C, and other denitrification enzymes are good examples of enzymes to target using TIA. Enzymes produced by microbes that alter the oxidation-reduction (redox) status of the host cell they infect towards the "reduction" end of the continuum, are particularly favored as targets for TIA. Microbes use such enzymes to control the redox status of their host cells, thereby inhibiting both apoptosis and the rapid influx of mononuclear cells to the site of infection, as multiple intracellular signaling processes are influenced by the cell's redox status.

The enzymes listed above and below are found in most bacterial species, evolving from common ancestors and remaining highly conserved in their amino acid sequence and tertiary configuration. Accordingly, X-ray crystal structure from an enzyme produced by one microbial species can be used not only to help guide deletion and replacement mutations for the specific microbe but also for the homologous enzyme in another species. On occasion, the enzyme is so highly conserved among all life forms that X-ray crystal structure data from eukaryotes can be used. One skilled in the art should be able to make enzymatically less efficient forms of any of these enzymes using X-ray crystal data and the amino acid deletion strategy outlined above and further exemplified in Example 11. Specific sources of information that be used to help guide the generation of less efficient mutants of the various enzymes include:

Iron-Manganese Superoxide Dismutase:

The use of TIA to make incremental mutants of SOD is described in Example 11. The amino acid sequence and crystal structure of iron-manganese superoxide dismutase is highly conserved among microbial species such that the deletions and substitutions that are listed for *M. tuberculosis* SOD in Example 11, or near approximations of these changes, can also be used to construct incremental mutants of Fe,Mn SODs from other bacterial species. Alignment of the amino acid sequences of multiple Fe,Mn superoxide dismutases and correlation with the structural features of the enzyme have been reported by Lah (Lah et al., 1995) and Ursby (Ursby et al., 1999).

Zinc-Copper Superoxide Dismutases:

Cu,Zn superoxide dismutases also catalyze the dismutation of superoxide. Alignment of the amino acid sequence of multiple Cu,Zn superoxide dismutases and correlation with the structural features of the enzyme have been reported by Pesce (Pesce et al., 2000) and Forest (Forest et al., 2000).

Catalases:

Catalase is present in most eukaryotic and aerobic prokaryotic organisms. It can utilize hydrogen peroxide both as an electron donor and receptor in a dismutation reaction that yields water and molecular oxygen. Several catalases have been analyzed by X-ray crystallography and all possess a core structure of about 470 residues with closely related conformation (Bravo et al., 1999). Alignment of the amino acid sequences of multiple catalases and correlation with the structural features of the enzyme has been reported by Gouet (Gouet, Jouve, and Dideberg, 1995).

Thioredoxin System:

Thioredoxin (TRX), thioredoxin reductase (TR) and NADPH comprise the thioredoxin system, which is ubiquitous and operates via redox-active disulphides, providing electrons for a wide variety of different metabolic processes (Powis, Briehl, and Oblong, 1995). TRX also functions as a general protein disulphide reductase. Therefore, the activities of these enzymes are important in maintaining an optimal intracellular redox environment for the microbe. In addition to a general anti-apoptotic effect rendered by its effect on the redox status of the host cell, TRX also directly inhibits apoptosis by binding to and inhibiting apoptosis signal-regulating kinase (ASK-1) (Saitoh, Nishitoh, Fujii, Takeda, Tobiume, Sawada, Kawabata, Miyazono, and Ichijo, 1998). A mutant of M. tuberculosis with diminished thioredoxin production was constructed by using antisense techniques and demonstrated that it is attenuated in vivo [FIG. 6]. It also induced the rapid infiltration of mononuclear cells into the lung [FIG. 23] in a manner similar to that observed with SOD-diminished M. tuberculosis. Having taught how to make a TRX-diminished M. tuberculosis mutant, the activity of this enzyme can also be diminished in a mutant already partially attenuated by either allelic inactivation or TIA of another enzyme to permit fine-tuning to improve the balance between attenuation and immunogenicity, and render a pro-apoptotic effect.

The X-ray crystal structure of thioredoxin from E. coli and many other prokaryotic and eukaryotic species has been determined and there is a high degree of identity between thioredoxin of different species (Eklund, Gleason, and Holmgren, 1991) including identification of highly conserved and functionally important amino acids. Similar data are available for thioredoxin reductase (Dai et al., 1996). Such data can be used to guide the construction of mutants with diminished activity.

Glutathione Reductases:

Glutathione reductases and glutaredoxin are important in maintaining the intracellular redox environment, and although they emerged evolutionarily distinct from the thioredoxin system, they perform many of the same functions for the cell. Alignment of the amino acid sequences of multiple glutathione reductases (glutaredoxin) and correlation with the structural features of the enzyme has been reported by Mittl (Mittl and Schulz, 1994).

Glutamine Synthetases:

Glutamine synthetase is a key enzyme in nitrogen metabolism and catalyzes the formation of glutamine from ammonia, glutamate, and ATP. Glutamine starvation selectively activates specific caspases, which leads to the induction of apoptosis (Papaconstantinou et al., 2000). Furthermore, the inhibition of a eukaryotic glutamine synthetase has been associated with apoptosis (Tumani, Smirnov, Barchfeld, Olgemoller, Maier, Lange, Bruck, and Nau, 2000). M. tuberculosis secretes glutamine synthetase in large quantities with a membrane-permeable form similar to SOD and it appears to be essential for infection, raising the possibility that, as with SOD, it functions as an anti-apoptotic enzyme in M. tuberculosis-infected macrophages. The glutamine synthetase of M. tuberculosis has been crystallized by Gill (Gill, Pfluegl, and Eisenberg, 1999). Alignment of the amino acid sequences of multiple glutamine synthetases and correlation with the structural features of the enzyme has been reported by Liaw (Liaw and Eisenberg, 1994).

ClpC Atpases:

ClpC Atpase is a member of the Clp 100-kDa heat-shock protein family, a class of highly conserved proteins implicated in the stress tolerance of many prokaryotic and eukaryotic organisms. In addition to SOD and thioredoxin, mutants of M. tuberculosis with diminished ClpC Atpase activity also are attenuated in vivo [FIG. 6]. Having enabled a ClpC Atpase-diminished M. tuberculosis mutant, the activity of this enzyme could be diminished in a mutant already partially attenuated by either allelic inactivation or TIA of another enzyme to permit fine-tuning to improve the balance between attenuation and immunogenicity.

Finally, although biosynthetic enzymes are less preferable than the anti-oxygen intermediate enzymes, anti-apoptotic enzymes, and anti-stress enzymes discussed above as targets for TIA, TIA could still be used to improve efficacy of some of the auxotrophic vaccine candidates that have been constructed for tuberculosis and other infectious diseases. For example, genes involved in amino acid (leuD, encoding 3-Isopropylmalate dehydratase small subunit) and purine (purC, encoding phosphoribosylaminoimidazole-succinocarboxamide synthase) biosynthesis have been identified that when inactivated in a virulent M. tuberculosis strain, cause the mutant to be cleared rapidly from animal models (Hondalus, Bardarov, Russell, Chan, Jacobs, Jr., and Bloom, 2000; Jackson, Phalen, Lagranderie, Ensergueix, Chavarot, Marchal, McMurray, Gicquel, and Guilhot, 1999). Although some level of protective immunity is conferred by vaccination with these strains, it has generally been less than that exhibited following vaccination with BCG. The rapid clearance of these strains from the organs of animals in vivo has been viewed as not enabling sufficient interaction between key microbial antigens and the host immune to generate an optimal immune response. Therefore, it is likely that less severe reductions in the activity of these enzymes generated by using TIA might enable such M. tuberculosis mutants to survive longer than the allelic knockout mutant, thereby lengthening the time for interaction with the host immune system and inducing a stronger protective immune response. Furthermore, by using TIA to make a range of mutants of leuD and purC that exhibit diminished enzymatic activity (50%, 45%, 40%, 35%, 30%, 25%, 20%, 15%, 10%, 5%, 2%, 1%, etc.) compared to the wild-type enzyme, and using these mutants to replace the wild-type alleles, M. tuberculosis mutants exhibiting a range of survival times in vivo should be observed. From these, one or more mutants could be selected that is clearly sufficiently attenuated not to cause disease yet that persists long enough to generate an immune response superior to that exhibited following vaccination with an allelic knockout mutant involving the same gene. The X-ray crystal structure of a phosphoribosylaminoimidazole-succino-carboxamide synthase (purC) enzyme from yeast with strong identity with the M. tuberculosis enzyme has been determined (Levdikov et al., 1998), and can be used to help guide specific amino acid deletions and replacements to yield mutants with diminished activity.

The present invention is more particularly described in the following examples which are intended as illustrative only since numerous modifications and variations therein will be apparent to those skilled in the art.

EXAMPLE 1

Construction of Sod-Diminished M. tuberculosis (Hereafter Called "Bacillus Vanderbilt-VA", or "BVV") and Documentation of its Attenuation In Vivo Methods Bacterial Isolates, Plasmids, Chemicals, and Culture Media: Bacterial isolates and plasmids used are shown in Table 1. *E. coli* strain DH5α was used as the host for molecular genetic manipulations unless otherwise indicated and was grown in LB media (Gibco/BRL, Gaithersburg, Md.). *M. smegmatis* mc$^2$155 and *M. tuberculosis* H37Rv were grown in Middlebrook 7H9 liquid media (Difco Laboratories, Detroit, Mich.) supplemented with 0.2% glycerol and 10% Middlebrook OADC enrichment (Becton Dickinson & Co., Cockeysville, Md.) or plated on Middlebrook 7H10 agar (Difco) supplemented with glycerol and OADC. Kanamycin at a concentration of 50 µg/ml or 25 µg/ml, respectively, was used to select for transformants containing pHV202, pLUC10, or their derivative plasmids in *E. coli* DH5α or *M. tuberculosis* H37Rv.

Construction of a shuttle vector for antisense DNA overexpression: The origin of replication of the *M. fortuitum* plasmid pAL5000 was recovered as a 2.6-kb DNA fragment from pBAK14 (Zhang et al., 1991). The gene encoding resistance to kanamycin (aph) was recovered as a 1.2-kb DNA fragment from pY6002 (Aldovini, Husson, and Young, 1993). The promoter of the 65-kDa heat-shock protein (Pr-HSP) was PCR-amplified from the chromosomal DNA of *M. tuberculosis* strain H37Ra using published DNA sequence data (Shinnick, 1987) to guide the construction of two oligonucleotide primers. The sequences of the forward and reverse primers were, respectively, 5' AGGCGGCCGCTCGAAC-GAGGGGCGTGACCCG (SEQ ID NO:1) and 5' CAGTCTAGAGACGGGCCTCTTCGTCGTACG (SEQ ID NO:2). Chromosomal DNA from *M. tuberculosis* isolate H37Ra was used as the template for PCR and was obtained by using methods described by van Soolingen et al. (van Soolingen et al., 1991). ORI myc, aph, and Pr-HSP were ligated into pBCSK+ to make pHV202 [Figure 2]. Another mycobacterial-*E. coli* shuttle plasmid, pLUC10, was used as a second vector for antisense DNA.

Construction of SOD-diminished mutants of H37Rv and isogenic control strains: To make the first antisense-sodA plasmid, pHV202-AS-SOD, a 151-bp fragment of sodA (corresponding to amino acids 139 through 189 of the open reading frame) was PCR-amplified using chromosomal DNA of *M. tuberculosis* H37Ra as a template. The DNA sequence data in accession number X52861 from GenBank (Zhang et al., 1991) was used to design and construct forward and reverse oligonucleotide primers for PCR with the sequences: 5'-CAGATCGATACGCGTGCTAGCATTCCAG-GTTTACGACCACC (SEQ ID NO:3) and 5'-CAGACTAG-TATCGGCCCAGTTCACGACGTT (SEQ ID NO:4), respectively. The PCR product was ligated into pHV202 using pBCSK+ (Stratagene, La Jolla, Calif. ) as an intermediate vector and using restriction enzymes which forced a reverse orientation of the sodA fragment behind Pr-HSP compared to the sodA open reading frame on the *M. tuberculosis* chromosome.

A second antisense-sodA plasmid was made using pLUC10. First, the sodA fragment cloned in pBCSK+ was PCR-amplified with HindIII and BamHI restriction sites. Also, the HindIII fragment from pLUC10 that contains the firefly luciferase gene (Cooksey, Crawford, Jacobs, Jr., and Shinnick, 1993) was PCR-amplified, except for the proximal 75 bp, using a primer containing a BamHI restriction site at the 5' end of the luciferase gene and preserving the distal HindIII restriction site. Subsequently the sodA and luciferase PCR products were ligated together at their BamHI ends. The conjoined partial SOD-luciferase DNA was cloned into pLUC10, replacing the original luciferase-HindIII fragment, and creating pLUC10-AS-SOD.

Plasmids pHV202, pLUC10, pHV202-AS-SOD, and pLUC10-AS-SOD were electroporated into *M. tuberculosis* H37Rv using standard methods (Hondalus et al., 2000) except that when the $A_{600}$ of the mycobacterial cultures reached 0.6, they were incubated in 37° C. and 5% $CO_2$ with 1.5% glycine and 50 ug/ml m-fluoro-DL-phenylalanine (MFP) for 48 hrs to enhance electroporation efficiency. The mycobacteria were washed twice and resuspended in ice-cold 10% glycerol. The Gene Pulser apparatus with the Pulse Controller accessory (Bio-Rad Laboratories, Hercules, Calif.) was used for all electroporation at 25 F and 2.5 kV with the pulse controller set at 1000 ohms. After electroporation, 1 ml of Middlebrook 7H9 media was added to the samples, and the transformants were allowed to incubate in 37 C and 5% $CO_2$ for 24 hrs. Transformants were plated on Middlebrook 7H10 agar containing 25 µg/ml of kanamycin, and successful transformation was confirmed by PCR of DNA unique to the plasmid construct.

Northern Hybridization: Total cellular RNA from *M. smegmatis* mc$^2$155 and its transformants was harvested using the method of Cheung et al (Cheung, Eberhardt, and Fischetti, 1994). RNA was electrophoresed through 1.5% agarose-formaldehyde gel containing ethidium bromide, transferred to a Hybond nylon membrane, and hybridized with double-stranded chemiluminescent DNA probes specific for kanamycin (aph), firefly luciferase, and a 300-bp fragment of the AT-rich *S. aureus* β-lactamase gene, blaZ, that had been inserted downstream of the antisense sodA fragment in pHV202. Because there is strong homology between *M. tuberculosis* sodA and *M. smegmatis* sodA (Harth and Horwitz, 1999) that might limit the ability to discriminate between their RNA transcripts, DNA probes were constructed for the luciferase gene and blaZ gene fragment to use as surrogate genes for monitoring expression of the antisense *M. tuberculosis* sodA fragment in pLUC10-AS-SOD and pHV202-AS-SOD, respectively. It was assumed that since the antisense sodA fragment is between the promoter and the surrogate gene, that there would be a direct correlation between the expression of the sodA fragment and the probed transcript.

Western Hybridization: Samples consisting of lysed bacterial cells were adjusted to a protein concentration of 2.2 mg/ml as determined by using the Bio-Rad protein assay (Bio-Rad, Hercules, Calif.) with BSA as the protein standard. A 100 µg aliquot of these adjusted samples were run on a 12% PAGE gel and transferred to Hybond ECL nitrocellulose membranes (Amersham, Arlington Heights, Ill.). Membranes containing proteins from H37Rv-derived transformants were hybridized with a 1:24,000 dilution of polyclonal antisera against H37Rv whole cell lysate (E-293 antisera) obtained from Colorado State University under NIH, NIA/D Contract N01 AI-75320 (Tuberculosis Research Materials and Vaccine Testing). In addition, to identify the location of SOD on the membrane, they were also stripped and hybridized with polyclonal rabbit antisera at a dilution of 1:100 made by immunizing a rabbit with recombinant *M. tuberculosis* SOD produced in *E. coli* JM109 bearing sodA behind a T7 promoter (Lakey et al., 2000). Recombinant SOD was purified by nickel affinity column chromatography. The nitrocellulose membranes were incubated first with antisera at the dilutions noted above followed by incubation with a 1:1000 dilution of horseradish peroxidase-conjugated goat anti-rabbit antibodies (Boehringer Mannheim, Indianapolis, Ind.). The immunoblots were developed with ECL Western blot detection reagents (Amersham Pharmacia, Arlington Heights, Ill.).

Kill-Kinetic Assays: H37Rv transformants were exposed for 6 hours to two concentrations of hydrogen peroxide (Sigma Chemicals, St. Louis, Mo.) in Middlebrook 7H9 broth containing 10% albumin-dextrose and 0.2% glycerol but lacking oleic acid and catalase. After exposure, serial dilutions were performed in broth and 50 µl aliquots were plated on 4 quadrant plates containing 7H10 agar with OADC. After 6 weeks, colonies were counted. The average values of triplicate determinations are reported.

Murine Inoculation and Clearance Studies: To prepare inocula for injection into C57BL/6 mice, M. tuberculosis H37Rv and transformants were grown in modified Middlebrook 7H10 broth (7H10 agar formulation with malachite green and agar deleted) containing 10% OADC (Difco). The suspensions were diluted to achieve a 100 Klett unit reading (approximately $5 \times 10^7$ cfu/ml) on a Klett-Summerson Colorimeter (Klett Manufacturing, Brooklyn, N.Y.). Aliquots of the inocula were serially diluted and directly plated to 7H10 agar containing 10% OADC for backcounts to determine the precise inoculum size.

Female C57BL/6 mice aged 5-6 weeks were purchased from Jackson Laboratories, Bar Harbor, Me. Infected and uninfected control mice were maintained in a pathogen-free Biosafety Level-3 facility at the Syracuse VA Medical Center. Animal experiments were approved by the Syracuse VAMC Subcommittee on Animal Studies and performed in an AALAC-approved facility.

Two 28-day inoculation and clearance experiments were performed. C57BL/7 mice received approximately $1 \times 10^7$ du (as estimated by the spectrophotometric absorbance of the sample) of one of the six isolates via a lateral tail vein. A total of eight experimental arms involving seven strains were evaluated, with H37Rv(pLUC10-AS-SOD) being used in both experiments. Each arm included 24 mice, which were divided into 4 groups of 6 mice each and segregated by caging based on whether the group was to be sacrificed on day 1, day 7, day 14, or day 28 post-inoculation. Euthanasia was achieved by $CO_2$ inhalation. Spleens and right lungs were removed aseptically, tissues were placed in a sealed grinding assembly (IdeaWorks! Laboratory Products, Syracuse, N.Y.) attached to a Glas-Col Homogenizer (Terre Haute, Ind.) and homogenized. Viable cell counts were determined by titration on 7H10 agar plates containing 10% OADC.

Histopathologic Evaluation: Left lungs were harvested from mice and fixed in 10% formalin (Accustain, Sigma). Lungs were paraffin-embedded, cut in 4-µm sections and stained with hematoxylin and eosin, Ziehl-Neelsen, and trichome. A pathologist who was unaware of the experimental arm evaluated the lung sections from each mouse.

Results.

Construction of SOD-Diminished Mutants of H37Rv and Control Strains: To construct SOD-diminished mutants of H37Rv, a 151-bp portion of the M. tuberculosis gene encoding superoxide dismutase (sodA) was ligated into mycobacterial-E. coli shuttle vectors pHV202 [FIG. 2] and pLUC10 to yield pHV202-AS-SOD and pLUC10-AS-SOD, respectively. The ligation site was immediately behind the ATG initiation codon of the 65-kDa heat-shock protein and the sodA fragment was inserted in a direction antisense to its normal orientation behind the sodA promoter on the chromosome. Accordingly, activation of the promoter of the heat-shock protein (Pr-HSP) was expected to produce an RNA transcript that would be "antisense" to normal sodA mRNA. Each plasmid was electroporated into M. smegmatis strain mc²155 and the virulent M. tuberculosis strain H37Rv.

M. smegmatis was used as a mycobacterial host to monitor expression of the antisense sodA transcripts behind Pr-HSP. Expression of antisense sodA in the M. smegmatis transformant containing pLUC10-AS-SOD was verified by Northern hybridization [FIG. 3], however the transformant containing pHV202-AS-SOD did not produce much transcript, raising questions about promoter integrity. DNA sequencing of the promoter through the antisense sodA fragment identified a four-base alteration in the nucleotide sequence in the −10 ribosome-binding site of the heat-shock promoter. This was repaired to yield pHV203-AS-SOD.

Slow Growth Phenotype of SOD-Diminished Mutants: Whereas transformants containing pHV202 and pLUC10 grew at a rate comparable to the parent H37Rv strain and were visible as distinct colonies on agar after 3 weeks incubation, transformants containing pLUC10-AS-SOD and pHV202-AS-SOD grew much more slowly. Although visible as pinpoint colonies at 4 weeks, it took 7 to 8 weeks before they reached a colony size comparable to 3- to 4-week growth of the parent and control strains.

In Vitro Production of Superoxide Dismutase: The quantitative production of SOD by H37Rv, H37Rv(pLUC10), and H37Rv(pLUC10-AS-SOD) were compared by Western hybridization [FIG. 4]. Transformation with pLUC10 had no effect on SOD production by H37Rv. In contrast, H37Rv (pLUC10-AS-SOD) produced less SOD than the control strains, however the density of the other protein bands was comparable suggesting a specific reduction of SOD. Densitometric calculations of the relative intensity of the SOD bands produced by the strains such that H37Rv(pLUC10-AS-SOD) produced only 13% the amount of SOD as control strains.

Killing by Hydrogen Peroxide: To determine the susceptibility of SOD-diminished H37Rv to hydrogen peroxide, inocula of approximately $2 \times 10^6$ cfu of H37Rv(pLUC10) and H37Rv(pLUC10-AS-SOD) were incubated in Middlebrook 7H9 broth lacking catalase and containing 5 mM or 10 mM of hydrogen peroxide for 6 hours. The SOD-diminished mutant was much more susceptible than the control strain to killing by hydrogen peroxide [FIG. 5], with a hundred-fold greater decline in viable bacillary counts following exposure.

Kinetics of M. tuberculosis Strains in a Murine Model: To determine whether diminished SOD production affects the survival of M. tuberculosis in vivo, H37Rv and its transformants were administered to C57Bl/6 mice via a lateral tail vein. The SOD-diminished strains were markedly restricted in growth compared to the control strains [FIG. 6]. This included apparent greater initial clearance in the first 24 hours post inoculation, in most cases some modest growth in vivo up to day 14, and a subsequent fall by day 28 presumably related to the development of a cellular immune response during the $3^{rd}$ and $4^{th}$ weeks. In contrast, bacillary counts of the control strains rose steadily in the lungs and spleens over 28 days, and some of the mice infected with these strains died in the $3^{rd}$ and $4^{th}$ week. By day 28 there was nearly a 100,000-difference in the number of viable bacilli for the SOD-diminished strains versus control strains.

EXAMPLE 2

Comparison of the Attenuation of BVV to that of the Current Vaccine for Tuberculosis, BCG (Bacillus Calmette-Guerin) Methods In another experiment, the clearance of mycobacteria after infection with BCG (Tice strain) and H37Rv(pLUC10-AS-SOD) was compared. Each of the two experimental arms were divided into groups segregated by caging based on whether the group was to be sacrificed on day 1, 4 weeks, 8 weeks, 12 weeks, 16 weeks, or 72 weeks post-inoculation. Inocula were administered via a lateral tail vein. Euthanasia and the harvesting of organs were performed as described above.

Results.

Comparative Clearance of Sod-Diminished H37Rv Versus BCG (Tice): Next, it was determined whether the declines in viable bacilli observed in the first 28 days with SOD-diminished strains were sustained over a longer duration of time by comparing the clearance of H37Rv(pLUC10-AS-SOD) to the clearance of another attenuated *M. tuberculosis* complex strain, BCG Tice. Inocula of $3.8\times10^6$ cfu/mouse for each strain were administered to separate groups of mice by tail vein. Mice that had been infected with H37Rv(pLUC10-AS-SOD) gained more weight than the mice that received BCG [FIG. 9]. Over the first 16 weeks, the clearance of SOD-diminished H37Rv in the lung roughly paralleled that of BCG Tice, with both strains exhibiting a greater than 100-fold decline in bacillary counts [FIG. 10]. In contrast, the SOD-diminished strain was cleared much more rapidly in the spleen than BCG Tice over the first 16 weeks, exhibiting respectively, 10.000-fold versus 10-fold reductions compared to the day 1 enumeration values. Subsequently, the number of bacilli in the lung was nearly constant with modest falls for both strains between 16 weeks and 17 months. However, in the spleen, the numbers of viable BCG and SOD-diminished bacilli continued to decline and fell below the lower limits of detection (10 cfu) in five of the 12 mice that had received H37Rv(AS-SOD).

Gross and Histopathologic Appearance of Lungs: The lungs of mice seventeen months post-inoculation showed distinctive differences in gross appearance based upon which attenuated strain they had received. Nodular lesions and large areas of consolidation were evident in the lungs of BCG-infected mice [FIG. 11]. In contrast, the lungs of mice infected with SOD-diminished H37Rv were darker and more homogeneous in appearance.

A pathologist who was unaware of which strain each mouse had received scored various histopathologic features based on microscopic examination of each lung. There was mild interstitial and peribronchiolar infiltration that was similar for the two groups of mice [Table 2, FIG. 12]. Lungs from BCG-infected mice exhibited greater alveolar infiltration, corresponding to the areas of consolidation and nodules observed upon gross inspection. Foamy macrophages were prominent within the areas of alveolar consolidation, occasionally with AFB visible by Ziehl-Neelsen stain. The lungs from mice infected with SOD-diminished H37Rv showed larger perivenous collections of lymphocytes, macrophages, and plasma cells.

EXAMPLE 3

Comparison of the Vaccine Efficacy of BVV to BCG

Next, BVV and BCG Tice were compared as vaccines. Six weeks following IV vaccination, C57Bl/6 mice were challenged with an intranasal inoculum of the virulent Erdman strain of *M. tuberculosis*, delivering an inoculum of $10^4$ to $10^5$ cfu to the lungs as assessed by enumeration of bacilli in the lungs of mice sacrificed on Day 1 post-challenge. This was a very rigorous challenge, as vaccinated mice are much more susceptible to virulent *M. tuberculosis* administered aerogenically than by the IV route (North, LaCourse, and Ryan, 1999) and we used a large inoculum. For example, in other recent trials involving new vaccine candidates, Jackson et al. used an IV challenge (Jackson, Phalen, Lagranderie, Enserguiex, Chavarot, Marchal, McMurray, Gicquel, and Guilhot, 1999) whereas Hondalus et al. challenged with 5 to 10 cfu by aerosol (Hondalus, Bardarov, Russell, Chan, Jacobs, Jr., and Bloom, 2000). Detailed enumeration was performed over the first 10 weeks, showing marked restriction of growth of the virulent Erdman strain in both vaccinated groups compared to unvaccinated controls [FIG. 13]. By 10 weeks post-challenge there was a clear benefit of vaccination with BVV compared with BCG, with a 40-fold difference in the number of bacilli in the lung (log 4.2 versus log 5.8, respectively, $P<0.05$) and marked differences in lung appearance. At nine months post-challenge, there was a trend towards a survival advantage among mice vaccinated with BVV compared to BCG (16 out of 18 versus 12 out of 18, respectively). The gross and histopathologic differences in lung appearance were even more impressive at the time of terminal sacrifice of a few surviving mice at 15 months post-challenge [FIGS. 14 and 15].

The Mechanisms of Attenuation and Vaccine Efficacy: The observations in Examples 2 & 3 show that greater apoptosis contributed to both innate and acquired immune responses. In contrast with cell necrosis, apoptosis has traditionally been characterized as a means of quiet death to remove cells without inducing an inflammatory response or triggering the immune system. Indeed, one interpretation of the superior weight gain in mice receiving BVV compared to BCG is that there likely were diminished inflammatory cytokines (e.g., TNF-α) with the former, as might be expected if apoptosis was more prominent as a host mechanism of eradicating SOD-diminished bacilli. Also, it seemed to make more sense that the marked improvement in vaccine efficacy of BVV compared to BCG was related to enhanced antigen presentation than from differences in the antigens produced by BCG and the SOD-diminished H37Rv strain, with BCG lacking key antigens. Comparative genome analysis suggests that only about 129 of approximately 4,000 (3%) of *M. tuberculosis* open reading frames are missing from BCG (Behr, Wilson, Gill, Salamon, Schoolnik, Rane, and Small, 1999; Kaufmann, 2000), so that if antigens unique to H37Rv were responsible for the difference in vaccine efficacy, we were expecting at most a modest enhancement of protection from our attenuated *M. tuberculosis* strain. Instead we observed a much more dramatic difference in vaccine efficacy, leading us to consider that there might be important differences in the way the antigens were presented.

EXAMPLE 4

Demonstration that BVV Induces Rapid Mononuclear Cell Infiltration at the Site of Infection with Apoptosis of these Cells The considerations outlined above led us to measure apoptosis in the mouse lung sections harvested during the early course of infection by BVV and virulent H37Rv controls, which had shown such distinctive differences in the pattern of inflammatory cell infiltration [FIG. 7]. We evaluated DNA fragmentation by TUNEL (terminal deoxynucleotidyl transferase-mediated 2'-deoxyuridine 5'-triphosphate-biotin nick end labeling) to identify apoptotic cells. Moderate apoptosis was observed among the mononuclear cell infiltrate of mice infected with BVV at day 1, day 7, and day 14 which intensified as the interstitial infiltration increased at day 28 [FIG. 8]. In contrast, although apoptosis was identified at day 1 and day 7 in mice infected with virulent *M. tuberculosis*, it appeared to primarily involve cells lining the alveolar spaces and there were fewer apoptotic mononuclear cells in the interstitial space. By day 14, mice infected with virulent bacilli exhibited minimal apoptosis among the interstitial and alveolar infiltrates. So in summary, there was a marked quantitative difference in the percent of apoptotic cells observed by day 14 for the virulent and SOD-diminished strains. Furthermore, when differences in the magnitude of interstitial mononuclear cell infiltrate are also considered, it is clear that apoptosis of the inflammatory cells, which appear by a pathologist's review to be comprised primarily of macrophages, occurred almost exclusively in the mice infected with BVV and was negligible in mice infected with virulent H37Rv.

Therefore, we conclude that the abundant amount of extracellular SOD made by virulent *M. tuberculosis* strains blocks both the early recruitment of an interstitial mononuclear cell infiltrate and apoptosis among these cells. By reducing SOD production in H37Rv we converted *M. tuberculosis* infection into a more immediate inflammatory process, but with predominant mononuclear cells that generally are associated with chronic rather than acute infection. We also unmasked apoptosis as a host defense mechanism, enabling better initial control of infection, as there is growing evidence that macrophage apoptosis kills tubercle bacilli and is important in controlling mycobacterial infections (Fratazzi et al., 1999; Komfeld, Mancino, and Colizzi, 1999; Molloy, Laochumroonvorapong, and Kaplan, 1994; Oddo et al., 1998).

EXAMPLE 5

Demonstration that Vaccination with BVV Induces Greater Early Interstitial Mononuclear Cell Infiltration in the Lung than Vaccination with BCG The demonstration of rapid mononuclear cell infiltration with apoptosis supports the idea that enhanced antigen presentation via apoptosis-associated MHC Class I pathways is the basis for the vaccine efficacy of BVV.

Figure 17:
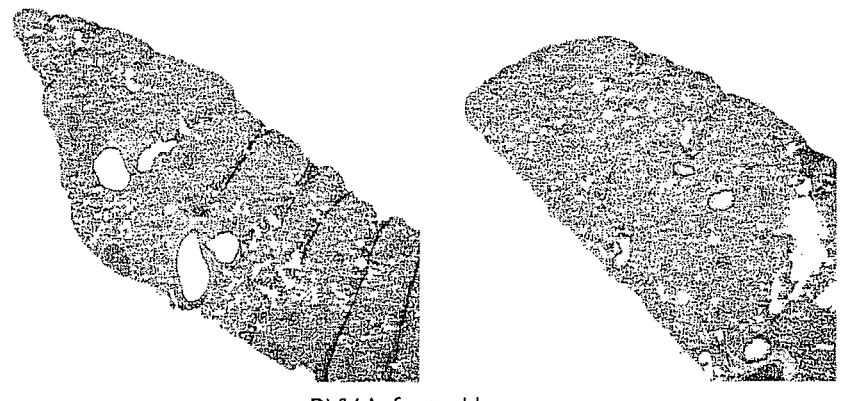
Figure 17:

To test this hypothesis, we compared the amount of interstitial lung infiltration observed following inoculation of BCG Tice versus BVV. Each bacterial inoculum had been adjusted spectrophotometrically to yield a bacterial density corresponding to $1.4 \times 10^7$ cfu. Histopathologic examination of lungs harvested on day 1 showed intense interstitial infiltration in mice that had received BVV compared to a minimal inflammatory response among recipients of BCG Tice [FIG. 17].

This shows that although BCG is an attenuated bacterium that is useful as a vaccine, it does not induce the same type of early inflammatory response as BVV. Instead, it is attenuated by other means that involve the deletion of certain chromosomal genomic elements (Behr, Wilson, Gill, Salmon, Schoolnik, Rane, and Small, 1999; Kaufmann, 2000) but do not result in a reduction in SOD production. BCG does not enhance the innate immune response the way that BVV does.

EXAMPLE 6

Demonstration that Vaccination with BVV Induces Stronger CK8+ T-Cell Responses than Vaccination with BCG Investigation into the host immune responses that mediate the enhanced vaccine efficacy of BVV have included measurements of CD4+ and CD8+ T-lymphocyte responses in BCG- and BVV-vaccinated mice, performed during repeat vaccine efficacy experiments.

Samples for FACS (fluorescence activated cell sorting) were prepared in the following manner: Individual lungs were harvested from experimental and control mice. Each lung was then perfused with DMEM+10% FCS (fetal calf serum) via pulmonary artery cannulation. Lungs were then placed in ice cold DMEM and diced in a sterile fashion into 1 mm cubes using a surgical scalpel and passed through a wire mesh to obtain a single cell suspension (SCS), and RBC lysis was performed. The SCS was then layered onto Lympholyte-M (Cedarlane Labs, Ontario, CA) and the interface was isolated after centrifugation per manufacturer's specifications. Cells were then washed with wash buffer (PBS with 2% FCS and 0.1% sodium azide) several times and counted. To isolate cells for dendritic marker analysis, lung fragments were incubated with collagenase for 30 minutes and subsequently treated with red cell lysis buffer. A lymphocyte gradient was not performed. For all cells, viabilty was assessed by trypan blue exclusion and was consistently greater than 90%. In most circumstances, $1 \times 10^6$ cells were aliquoted to samples prior to staining. For total cell preparations in which there were less than $1 \times 10^6$ cells, all cells were used. Table 3 indicates the type, source, and amount of antibodies used for FACS and Immunohistochemistry.

Individual samples were then incubated with the appropriate antibodies on ice for 30 minutes. Samples were then washed twice using wash buffer as specified above. Samples were then fixed overnight in 2% paraformaldehyde according to approved biosafety protocols and analyzed on either 3- or 4-color flow analysis using a Becton-Dickinson FACScalibur instrument with Mac Workstation.

In one experiment, C57Bl/6 mice were vaccinated via a lateral tail vein with inocula of BVV or BCG that had been adjusted spectrophotometrically to yield a bacterial density corresponding to $1.4 \times 10^7$ cfu. Six weeks after vaccination, the mice received $5 \times 10^4$ cfu of the virulent Erdman strain of *M. tuberculosis* via intranasal administration. Four month post-challenge, mice from each group were harvested and SCS prepared for FACS as described above. Analysis of cell populations showed that both vaccines induced strong CD4+ T-cells responses [FIG. 16]. In contrast, BCG induced only weak CD8+ T-cell responses, confirming the observations of other investigators regarding the poor capability of BCG to stimulate this arm of the immune response (Silva, Bonato, Lima, Faccioli, and Leao, 1999; Hess, Miko, Catic, Lebmensiek, Russell, and Kaufmann, 1998; Kaufmann, 2000). However, BVV-induced very strong CD8+ T-cell responses, such that at 16-weeks post-challenge with virulent *M. tuberculosis*, 38.4% of lymphocytes from mice vaccinated with BVV were CD8+ T-cells, compared to 18% of lymphocytes from BCG-vaccinated mice.

In a second experiment, mice were vaccinated with a smaller number of BCG or BVV, approximating $5 \times 10^5$ cfu administered via a lateral tailvein. In addition, two different BVV constructs were evaluated to demonstrate that the CD8+ T-cell responses observed above were reproducible when a different antisense-SOD plasmid was used to confer the SOD-diminished phenotype. Table 4 shows cells in lungs of mice at 24 hours after challenge with virulent *M. tuberculosis*, grouped according to the vaccine strain they had received nine weeks earlier.

In a third experiment, mice were inoculated with $5 \times 10^7$ cfu of BVV or BCG via a lateral tailvein. Mice were harvested at one month post-vaccination and SCS were prepared and analyzed by FACS as described above. Results again showed a greater CD8+ T-cell response to vaccination with BVV than vaccination with BCG [Table 5].

In summary, these results document the strong CD8+ T-cell responses induced by BVV. Furthermore, the CD4+ T-cell responses appear at least as strong as those generated following vaccination with BCG. When considered together, the results of Examples 4-6 indicate that apoptosis of macrophages infected with BVV leads to enhanced MHC Class I antigen presentation, probably via apoptosis-associated cross-presentation of mycobacterial antigens to CD8+ T-cells.

An additional implication of these results that provides insight into why BCG has not been an especially useful vaccine in controlling the pulmonary form of tuberculosis is also suggested by the present data. In essence, since CD8+ cytotoxic T-lymphocyte (CTL) responses are not prominent in the host immune response to BCG (Kaufmann, 2000), this may force the host to utilize more inflammatory and necrotizing immune mechanisms to contain both the BCG vaccine strain and any subsequent challenge with virulent *M. tuberculosis*, as exemplified in our vaccine efficacy results [FIGS. 14 and 15]. So whereas BCG induces a predominant CD4+ T-cell response, BVV provides greater protection because it induces both CD4+ and CD8+ T-cell responses. Indeed, the marked increase in apoptosis on day 28 [FIG. 8] that accompanied the renewed interstitial mononuclear cell infiltration is probably best explained by CTL responses, which can induce apoptosis via death receptors (e.g., Fas) and perforin-granzyme pathways (Seder and Hill, 2000).

EXAMPLE 7

Demonstration of a Dose-Response Effect Upon CD8+ Responses Following Vaccination with BVV To address the effect of vaccine dose upon T-cell responses, groups of mice were vaccinated with two different preparations of BVV, i.e., H37Rv(pLUC10-AS-SOD) and H37Rv(pHV203-AS-SOD). BCG Tice and H37Rv(pLUC10-AS-SOD) were administered at doses of $5 \times 10^5$ cfu via a lateral tail vein, whereas H37Rv(pHV203-AS-SOD) was given at different doses approximating $5 \times 10^4$ cfu, $5 \times 10^5$ cfu, and $5 \times 10^6$ cfu. These doses produced counts of viable bacilli in the lungs at 24 hours ranging from log 1.5 to log 3.8. At nine weeks post-vaccination, the mice were challenged with $5 \times 10^4$ cfu of the virulent Erdman strain of *M. tuberculosis*. Mice were harvested at 14 months post-challenge and T-cell populations enumerated by FACS as described above. Although the percent CD8+ values achieved following vaccination/infection were not as high in this experiment as shown in the previous experiments, there was evidence of a dose-response in both CD4+ and CD8+ T-cell responses [Table 6].

EXAMPLE 8

Demonstration that BVV Induces Early Infiltration of the Lung by Monocytes and Dendritic Cells Investigations to elucidate the mechanisms underlying the enhanced CD8+ T-cell responses induced by BVV-vaccination have focused on the hypothesis that apoptosis-associated cross-presentation of microbial antigens by dendritic cells is involved. Presumably this occurs in the first few days following infection, as the most plausible interpretation of the enhanced apoptosis and renewed interstitial infiltration observed at day 28 in BVV-vaccinated mice [FIG. 8] is that it is caused by CD8+ cytotoxic T-lymphocyte (CTL) responses. Our observations of marked interstitial lung infiltration with apoptosis within 24 hours following inoculation of BVV as shown above [FIGS. 8 and 17] are consistent with the idea that apoptosis-associated antigen cross-presentation in the early post-infection period is the mechanism for achieving enhanced MHC Class I antigen presentation, thereby leading to strong CD8+ T-cell responses.

To determine the types of cells comprising the early interstitial lung infiltrate induced by BVV, C57Bl/6 mice were inoculated with $5 \times 10^7$ cfu of either BVV or BCG via a lateral tailvein. Mice were sacrificed at 67 hours post-infection. Single cell suspensions were prepared as described above for the lymphocyte studies, except that suspension was then incubated with collagenase D as described above. The reaction was then stopped with DMEM+10% FCS. FACS was performed using methods outlined above and antibodies and conditions outlined in Table 4 to enumerate cell populations including monocytes/macrophages, granulocytes, and NK cells. This showed an increase in monocytes with corresponding fall in granulocytes for all of the infected mice compared to non-vaccinated controls, with the highest values observed in mice that had received BVV [Table 7]. There were minimal differences in lymphocyte populations at this early time-point, with the possible exception of NK cells [Table 8]. The lack of differences in the CD4+ and CD8+ T-lymphocyte subpopulations at 67 hours post-infection [Table 8] evolving into clear differences noted by 4 weeks and later time-points [Tables 4-6] is consistent with the development of adaptive cellular immune responses as a consequence of vaccination.

An experiment was performed to assess infiltration of dendritic cells into the lung post-vaccination to further determine if BVV establishes conditions conducive for apoptosis-associated antigen cross-presentation in vivo. C57Bl/6 mice were inoculated with $5 \times 10^7$ cfu of either BVV or H37Rv via a lateral tailvein. Mice were sacrificed at 20 hours post-infection. Single cell suspensions were prepared as described above. FACS was performed using methods outlined above and antibodies and conditions outlined in Table 3 to enumerate dendritic cells. This showed an increase in cells co-expressing CD11c and CD80 markers, indicative of activated dendritic cells, in mice infected with BVV compared to H37Rv [Table 9].

EXAMPLE 9

BVV Influences the Expression of Apoptosis-Associated Genes in Mouse Macrophages The mechanism of achieving the co-localization of apoptotic macrophages with dendritic cells in vivo might involve the rapid induction of both NF-κB activation and apoptosis by BVV [FIG. 19*a*].

To assess early apoptosis gene signaling induced by BVV, we have used macrophage cultures derived from mouse bone marrow monocytes and RNase protection assays (RPAs) [FIG. 19*b*]. The cell cultures are infected with BVV or virulent H37Rv at a 3:1 multiplicity of infection. Viability at day three in vitro was >90% for both cultures. These results show a down-regulation of the expression of TNF-α receptor-associated death domain (TRADD) and fas-associated death domain (FADD) by the third day post-infection in cells infected with virulent H37Rv, suggesting that this might be the mechanism of the inhibitory effect of *M. tuberculosis* infection upon macrophage apoptosis in vitro (Durrbaum-Landmann et al., 1996). In contrast, a higher level of expression of these genes was maintained in cells infected with BVV (Oddo, Renno, Attinger, Bakker, MacDonald, and Meylan, 1998).

It is likely that the iron-cofactored SOD of *M. tuberculosis* contributes to infection pathogenesis by scavenging superoxide, thereby blocking both NF-κB activation and apoptosis of mononuclear cells, thereby impairing the innate immune response to infection and allowing the organism to persist. By reducing SOD production in BVV, both NF-κB activation and apoptosis were enhanced, thereby facilitating apoptosis-associated cross-presentation in vivo.

EXAMPLE 10

Construction of SOD-Diminished Bcg

One implication of the above Examples is that reducing SOD activity by BCG might similarly enhance its antigen presentation, enabling it to become a better vaccine against tuberculosis while becoming even further attenuated and presumably better tolerated. Accordingly, the pHV203-AS-SOD plasmid has been electroporated into BCG Tice, using methods outlined in Example 1. Transformants exhibit the slow-growth phenotype that was characteristic of reducing SOD production in H37Rv. Comparisons of T-cell subpopulations in the lung at four weeks following intravenous vaccination with BCG and BCG(pHV203-AS-SOD) show that, as predicted, reducing SOD production enhances CD8+ T-cell responses [Table 10]. This demonstrates that an already attenuated bacterium that is widely used as a vaccine can have its immunogenicity enhanced by practicing this invention. Not only will this improve the performance of BCG as a vaccine against tuberculosis, but it will also enhance its usefulness as a vector for expressing heterologous antigens, including antigens from other pathogenic microbes and cancer neoantigens.

EXAMPLE 11

Generation of SOD Enzyme Mutants with Diminished SOD Activity

As noted above, the TIA strategy has been designed to deal with genes in which allelic inactivation is not feasible due to the essential nature of the microbial factor. A key feature of the TIA strategy is that it produces vaccine strains without the risk of reversion. The specific methods include standard molecular genetic strategies and produce strains for in vivo testing and for human trials. Targeted incremental attenuation (TIA) represents a new paradigm for developing live-attenuated vaccines for pathogenic microbes. Generally, the four steps involved are summarized and described below in detail.
Step 1:
Identify an enzyme that is essential for microbial survival in vivo. Antisense (AS) techniques are used to rapidly identify essential genes that attenuate the pathogen, or confer a pro-apoptotic effect. The AS/TIA strategy will work best when applied to enzymes that are essential for virulence but are not components of central metabolic pathways that cause nutrient deprivation and possibly alter bacterial gene expression in response to the stress of starvation (i.e., auxotrophs). The SOD of *M. tuberculosis* is an example of an essential enzyme, and is the target enzyme described in this Example. However it is understood that the methods described can be routinely applied to other enzymes in other pathogens.
Step 2:
Make mutated forms of the gene encoding the enzyme that either alter its primary structure, or reduce its expression by modifying the nucleotides that regulate transcription and translation or by replacing its promoter with a less efficient promoter.
Step 3:
Replace the wild-type gene with one or more mutant forms to produce an attenuated microbe. This may also be achieved by substituting a homologous but less efficient enzyme from another species. The mutants thus produced evidence an incremental reduction in enzyme efficiency or production, thus resulting in attenuation. Attenuated microbes are identified as incrementally attenuated mutants by assessing in vivo attenuation. Depending upon the enzyme, it might also be possible to measure in vitro difference such as stair-step differences in their susceptibility to hydrogen peroxide or superoxide anion for mutants with diminished SOD activity. For example, mutations in the SOD gene of *M. tuberculosis* are generated to produce microbes with stair-step reductions in SOD activity that exhibit stair-step reductions in pathogenicity in vivo are generated using the molecular methods described herein. The activity of the SOD is reduced to 35%, 25%, 15%, 10%, 5%, etc. of the activity of the wild-type enzyme by any of the described techniques for targeted incremental attenuation.
Step 4:
Screen attenuated microbes for a strain that achieves an appropriate balance between attenuation and immunogenicity for use as a vaccine. By producing multiple vaccine candidates, rather than having a single vaccine candidate, multiple mutants can be tested to identify the one with greatest efficacy as a vaccine. This identification is based on assessing immunogenicity and attenuation for each mutant to select mutants with the right balance between immunogenicity and attenuation. When the technique is applied to strains that are already sufficiently attenuated by other methods, such as BCG, and the mutations being introduced are to render a pro-apoptotic effect to enhance antigen presentation, then the goal is to optimize immunogenicity.

More specifically, the wild-type *M. tuberculosis* SOD gene has been cloned into *E. coli* vectors. Two versions of the SOD gene have been cloned: one with the native sodA promoter in pNBV-1 {Howard, Gomez, et al. 1995 370/id} and the other a promoterless sodA in the expression plasmid pKK233-2 (Pharmacia) that has a restriction site at the initiation ATG codon, such that the mature SOD product is made without being a fusion protein (Harth and Horwitz, 1999). PCR-based mutagenesis (Ho, Hunt, Horton, Pullen, and Pease, 1989) or other mutagenesis techniques is used to alter the nucleotide sequence of the cloned SOD gene to produce amino acid (AA) deletions and substitutions, which are confirmed by DNA sequencing.

Regarding deletions, the focus is on portions of SOD where AA changes are unlikely to completely eliminate enzyme function. The crystal structure of SOD is known (Cooper et al., 1995) [FIG. 21]. Therefore, the mutation process starts with target regions distant from the active site, since they are likely to yield mutant enzymes with a partial rather than complete loss of enzyme activity. Several mutants have been generated with single AA deletions and one double-deletion [FIG. 21, Table 11] in inter-domain regions (i.e., between two alpha-helices). These mutant SODs have reduced activity compared to the parent enzyme [Table 11].

To achieve greater reductions in enzyme activity, mutants that have a combination of the deletions noted in Table 11 as well as two- to three-AA deletions in the inter-domain regions can be generated. Examples of such mutants include an E54-D55 deletion mutant, a K53-E54-D55 deletion mutant, a G87-G88-D89 deletion mutant, a N86-G87-G88-D89 deletion mutant, a L133-G134 deletion mutant, a L133-G134-N135 deletion mutant, a F149-P150 deletion mutant, a F149-P150-L151 deletion mutant, a V184-V185 deletion mutant, and a N183-V184-V185 deletion mutant [see FIG. 21 to identify the positions of these deletions within SOD]. Other deletions and substitutions could also be introduced to achieve further reductions in SOD activity, or if needed, to identify mutants with greater SOD activity (e.g., 35%, 40%, 45%, 50%) than the mutants listed in Table 11.

Other changes can be made in SOD in a methodical fashion based on X-ray crystal structure data to create mutants with incrementally diminished enzyme activity, such as employing a strategy that sequentially eliminates residues in interdomain regions. For example:
1. Progressively delete amino acids between V37 and F67 (α1-α2 helices and interjoining region)
   delete G39 first, then G39-A40, then K38-A40;
   delete E54 first, then E54-D55, then K53-D55; then K53-H56, then K53-S57, then K53-A58, then K53-I59, then K53-L60, then K53-L61, then K53-N62, then K53-E63, then K53-K64, then K53-K65, then K53-L66, then K53-A67

The rationale behind this strategy is that H28, H32, Y36 are invariant, H28 is involves in binding of the iron cofactor, residues 41-50 form an immunogenic epitope in the highly homologous *M. leprae* SOD that should be maintained, and that the α1-α2 loop is important in tetramer formation in other species but not in the SOD of *M. tuberculosis*.

2. Shorten the gap between α2-α3 helices (residues S84-T92)
   delete G88 first, then G87-G88, then G87-D89, then N86-D89, then N86-K90, then P85-K90, then P85-P91, then S84-P91, then S84-T92; then continue to cut into α3 helix one amino acid at a time and do the same through α4 helix all the way through V120; This domain linker region is significantly more flexible than the rest of the protein.

3. Eliminate residues from T132-N135 stretch between β1 and β2 strands
   delete G134 first, then L133-0134, then L133-N135, then T132-N135

4. Eliminate residues from D144-G152 loop between β2 and β3 strands
   delete P150 first, then F149-P150, then F149-L151, then N148-L151, then N148-G152, then T147-G152, then T147-L153; then Q146-L153

5. Eliminate residues in interjoining region between α5-α6
   delete V184 first, then V184-V185, then N183-V185, then N183-N186 This would pull α6 up into α2 and exert steric hindrance close to catalytic site.

6. Progressively delete N-terminus
7. Progressively delete C-terminus

Regarding substitutions, there are four histidine residues in SOD that coordinate the catalytic iron co-factor, either directly or via a hydroxyl group (Cooper, McIntyre, Badasso, Wood, Mang, Garbe, and Young, 1995). These have been individually converted to lysine residues and found to have diminished activity compared to wild-type SOD [Table 11]. Other basic amino acids such as arginine can also be used. All replacement mutations involve ≧2 nucleotide substitutions so as to diminish the likelihood of a single point mutation reversion back to the wild-type enzyme.

The mutant sodA genes are cloned into pKK233-2 and pNBV-1. pKK233-2 containing a wild-type or mutant sodA alleles is transformed into a SOD double-negative (sodA-, sodB-) *E. coli* strain CK9C1891 (Danielle Touati, Institut Jacques Monod, Paris) (Carlioz and Touati, 1986). Recombinant *M. tuberculosis* SOD has previously been shown to enable SOD-deficient *E. coli* to grow in minimal media (Harth and Horwitz, 1999), and the present data confirm this observation [Table 11].

Screening for Mutants with Reduced SOD Activity:

Two screening techniques have been used and will be used to identify mutant SODs with diminished SOD activity compared to the wild-type enzyme. Growth rate is studied in M9 or M63 minimal media. Growth rates of CK9C1891 transformants containing mutant sodA alleles are calculated as shown in FIG. 22. It is expected that the ability of SOD mutants to increase the growth rate of a non-replicating SOD double-negative strain in minimal media [Table 11] will be roughly proportional to the activity of the mutant SOD.

In general, hydrogen peroxide susceptibility is more sensitive for detecting differences between SOD+ and SOD-negative strains than susceptibility to paraquat-generated superoxide (Harth and Horwitz, 1999) and is therefore more suitable as a screening test. This may be due, in part, to the irreversible inactivation of the iron SOD of *M. tuberculosis* by hydrogen peroxide (Bunting et al., 1998).

Although not essential to the invention, more precise determinations of the enzymatic activity of SOD mutants can be achieved by cloning mutant sodA alleles into *M. vaccae* to produce recombinant SOD for specific activity determinations. Others have used *M. vaccae* to produce and purify recombinant *M. tuberculosis* SOD for X-ray crystal analysis (Cooper, McIntyre, Badasso, Wood, Zhang, Garbe, and Young, 1995; Bunting, Cooper, Badasso, Tickle, Newton, Wood, Zhang, and Young, 1998). The plasmid vector (p16R1) containing the wild-type sodA allele is used. However, any mycobacterial-*E. coli* shuttle vector, for example, pHV202, can be used. To avoid hybrid enzymes representing oligomerization of *M. tuberculosis* SOD monomers with *M. vaccae* SOD monomers, modifications of the Kusunose purification procedure (Kusunose et al., 1976) that was developed to prepare SOD crystals is used. The protocol involves sonication of the *M. vaccae* cells, ammonium sulphate precipitation, and anion exchange chromatography in which the *M. tuberculosis* SOD tetramer elutes prior to 3:1, 2:2, 1:3 hybrids or the *M. vaccae* SOD tetramer. Yield is typically 1.5-2 mg per liter of *M. vaccae*. SOD assays are performed by monitoring inhibition of the reduction of cytochrome C with a recording spectrophotometer (Beyer, Jr. and Fridovich, 1987) and protein concentrations determined using a BioRad protein assay kit. The specific activity of the purified recombinant mutant SOD enzymes is compared to that of wild-type SOD. Eight to ten SOD mutants that exhibit a range of activities (e.g., from 1% to 35% of parent SOD activity) are identified. Finally, as the substitutions and deletions being introduced might alter the metal co-factor from $Fe^{3+}$ to $Mn^{3+}$, ion content will be determined by using a peroxide inhibition assay which irreversibly inhibits Fe-SOD but not Mn-SOD (Bunting, Cooper, Badasso, Tickle, Newton, Wood, Zhang, and Young, 1998).

In summary, mutants of iron-cofactored SOD that exhibit from 1% to 36% of the activity of wild-type SOD (based on their ability to complement the growth rate of SOD-negative *E. coli* in minimal media) have been constructed. In accordance with the teachings of the TIA strategy, the mutant sodA alleles can be used to replace the wild-type sodA in virulent *M. tuberculosis* to achieve attenuation while retaining/enhancing immunogenicity. They also could be placed into strains of *M. tuberculosis* or *M. bovis* that have been attenuated by other means, e.g., BCG, to enhance vaccine efficacy by increasing immunogenicity.

EXAMPLE 12

Construction of Stable SOD-Attenuated Mutants of *M. tuberculosis* and BCG

Generating Mutant *M. tuberculosis*:

The wild-type sodA in *M. tuberculosis* H37Rv is replaced with mutant sodA alleles. Replacing wild-type SOD with a less-efficient enzyme yields a viable, albeit weakened bacilli similar to what is seen with the present AS-SOD mutants.

There are several feasible ways to achieve allelic replacement. One technique involves use of the "flexible cassette method" of Parish and Stoker (Parish and Stoker, 2000) that has proven capable of yielding unmarked mutations and even double unmarked mutants. Vectors p1NIL, p2NIL, pGOAL17, and pGOAL19 can be used to undertake this work. The Parish & Stoker reference describes how to construct the vectors using genes that are widely available. A person of skill in the art will know how to reconstruct these vectors or to make similar vectors. Basically, the system uses a suicide vector to deliver the mutant allele, and is made feasible by the selection of single crossover events as an intermediate step.

To achieve allelic replacement of the wild-type sodA with mutant sodA, the full-length mutant sodA allele including the promoter region with 541-bp upstream and 155-bp downstream of the open reading frame (ORF) has been cloned into the multicloning site (MCS) on p2NIL, which also contains a gene for kanamycin resistance ($kan^R$). Subsequently, a cassette from pGOAL19 containing the gene for hygromycin resistance ($hyg^R$), lacZ under the control of the antigen 85 promoter (i.e., a well-expressed *M. tuberculosis* protein), and sacB (resulting in killing by sucrose) under the control of the promoter for heat-shock protein 60 (hyg, $P_{Ag85}$-lacZ, $P_{hsp60}$-sacB) is cloned into p2NIL to yield pBVV* series plasmids named so as to indicate the nature of the SOD mutation, i.e., pBVV-H145K, pBVV-ΔE54, etc. Plasmid DNA is pretreated with 100 mJ UV light/cm$^2$ to stimulate homologous recombination and diminish illegitimate recombination (Parish and Stoker, 2000) and electroporated into H37Rv. Transformants with the $hyg^R$ $kan^R$ phenotype have been selected on 7H10 agar plates supplemented with 10% (w/v) OADC containing kanamycin (20 μg/ml) and hygromycin (100 μg/ml) and represent single-crossover recombinants.

Colonies are plated on non-selective 7H10 media and after 3-4 weeks a loopful of cells is resuspended in 7H9 broth and dispersed to generate single cells with vortexing and 1 mm glass beads. Serial dilutions are plated onto sucrose plates and incubated for 6-8 weeks. Use of both lacZ and sacB reduces the number of colonies to be tested while enriching for double-crossover recombinants. White colonies ($suc^R$) are streaked on plates with and without kanamycin to identify $kan^S$ colonies, verifying loss of the $kan^R$ gene. A portion of the $kan^S$ colonies have progressed from a single- to a double-crossover with allelic replacement, while others have eliminated the construct altogether and maintained the wild-type sodA allele. Small colonies are a reliable phenotypic characteristic of *M. tuberculosis* with diminished SOD activity. Accordingly, the smaller colonies are preferentially tested. PCR using a primer specific for the mutant sodA allele is used to document the suspected genotype, and DNA sequencing is performed on the PCR product of the complete SOD gene for additional verification.

An alternative strategy involves a two-step replacement in which the mutant SOD is first cloned into an attB phage integration site on the *M. tuberculosis* chromosome using the integration-proficient plasmid pMH94 (Lee et al., 1991) or similar vector. This is a high-efficiency manipulation. Then the normal SOD gene is targeted and inactivated using a modification of the phasmid-based transposon inactivation system described by Bardarov et al. (Bardarov et al., 1997) that enables allelic inactivation to be achieved with high efficiency. Care should be taken to construct the knockout vector based on upstream/downstream DNA unique to the normal chromosomal sodA so as to not target the mutant sodA in the attB site. In a further alternative, the temperature-sensitive plasmid vectors described by Pelicic et al. (Pelicic et al., 1997) can be used.

To document diminished SOD production, the H37Rv mutants are evaluated by Western hybridization and their susceptibility to hydrogen peroxide assessed as described with the AS-SOD strains [Example 1]. In addition, the mutant *M. tuberculosis* strains are assayed for SOD activity directly using the nondenaturing PAGE gel method of Beauchamp and Fridovich (Beauchamp and Fridovich, 1971). A gel technique in which the activity can be correlated with a specific protein band will be preferable to an SOD activity assay in liquid media due to the possibility that other mycobacterial products such as lipoarabinomannan, etc. can confound results by scavenging and detoxifying superoxide.

Screening for Revertants:

The following is not essential to the practice of TIA but will be useful in demonstrating the safety of SOD-diminished strains of *M. tuberculosis* constructed using the TIA strategy. As the rationale to make SOD-diminished mutants with deletions and AA substitutions is to lessen the likelihood of reversion back to virulence, reversion analyses are performed. The focus is not to determine just the precise mutation rate back to the parent form of the enzyme, which should be very low given the nature of the mutations being introduced, but primarily to see if any compensatory mutations arise which improve the fitness of the mutant SOD enzyme. The SOD mutants that are sufficiently inefficient to yield H37Rv mutants that are attenuated in vivo (see below) will be studied. Two basic strategies will be employed.

The sodA mutants in pKK233-2 transformed into *E. coli* strain CK9C1891 are exposed to chemical mutagenesis with ethyl methane sulfonate (EMS) and serially subcultured in M63 minimal media. Because mutations to an enzymatically more efficient SOD should enhance the growth rate relative to the original sodA variant, a mutant with enhanced SOD activity should eventually overgrow the original and become the predominant isolate. After exposure to EMS, the mutant is serially passaged for ten 2-day cultures in M63 media, at which time an aliquot is serially-diluted and plated on solid media. Individual colonies are compared to the original mutant for growth rate in minimal media and susceptibility to hydrogen peroxide as described above. Colonies that perform better than the original defined mutant on these assays will have their complete sodA sequence determined to identify DNA sequence changes associated with enhanced activity.

Because the host background of *M. tuberculosis* is different from *E. coli*, reversion analysis is performed directly with the H37Rv mutant. The goal is to monitor the in vivo phenotype in a manner that permits detection of any enhanced fitness of the H37Rv strain bearing a sodA mutant, including any compensatory changes in the production of other enzymes. For example, some catalase (katG) negative mutants of *M. tuberculosis* exhibit increased production of alkyl hydroperoxidase C (ahpC) resulting in some restoration of in vivo pathogenicity (Wilson, de Lisle, Marcinkeviciene, Blanchard, and Collins, 1998). By analogy, in addition to the potential for reversions or compensatory mutations in the sodA allele, there could be compensatory overproduction of the zinc-copper SOD encoded by sodC that might partially restore virulence. Because of the unique secreted nature of the Fe-SOD, it is possible that even high-level non-secreted sodC overproduction might not completely complement the sodA mutants.

Screening for mutants with restored fitness is done in two ways. First, the long-term in vivo survivors from clearance studies described herein [Example 2] are reinoculated into C57Bl/6 mice to determine whether they are more virulent than during initial testing. A fresh culture from the stock of the mutant strain is used for comparison. Second, the H37Rv (sodA mutant) strains are passaged serially in broth media with subcultures every 6 to 8 weeks for six months, and it is determined whether there is a rise in the virulence of the predominant strains in cultures at six months compared to stock cultures. The full sodA and sodC genes of any isolates with reversion to virulence are determined, including their promoters. This process can determine whether some mutants are more likely to revert to a virulent phenotype than others. It should identify the mutants within the range of attenuation that produces a useful vaccine candidate that is most likely to maintain a stable SOD-diminished phenotype.

In vivo Evaluation of Mutants:

Selected mutant SOD strains are evaluated in vivo for attenuation as described herein and [FIG. 6]. For example, in an initial experiment, each of five H37Rv strains containing mutant SOD enzymes with in vitro activities approximately 35%, 25%, 15%, 10%, and 5% that of normal SOD are given by tail vein as an inoculum of $10^7$ cfu into 24 C57Bl/6 mice. Controls include normal H37Rv and AS-SOD-diminished H37Rv strains. Mice are weighed weekly and six from each group are harvested at day 1, 2 weeks, 4 weeks, and 12 weeks for enumeration and histopathologic comparisons. These results establish the association of incremental reductions in pathogenicity with incremental reductions in SOD activity, thereby confirming the presence of the attenuation component of the vaccine. Similar in vivo experiments are performed for H37Rv strains with mutant sodA alleles constructed using the alternative strategies of differences in promoters, codons, and sodA genes.

Selected mutants exhibiting attenuation in vivo comparable to or greater than that exhibited by the AS-SOD-diminished H37Rv strain are compared to BCG and an AS-SOD-diminished H37Rv strain for long-term clearance and vaccine efficacy in a manner similar to that described herein [Examples 2 and 3].

Using the mutant sodA alleles to replace wild-type sodA in virulent *M. tuberculosis* will achieve attenuation while retaining/enhancing immunogenicity. Mutant sodA alleles also can be placed into strains of *M. tuberculosis* or *M. bovis* that have been attenuated by other means, e.g., BCG, to enhance vaccine efficacy by increasing immunogenicity.

EXAMPLE 13

Construction of TRX-Diminished and TR-Diminished H37Rv and BCG

As noted above, in addition to SOD there are other microbial factors produced by intracellular pathogens that are likely to have an anti-apoptotic effect upon mammalian cells. Thioredoxin (TRX) is another prominent extracellular protein produced by *M. tuberculosis*. To determine whether TRX is anti-apoptotic and associated with the ability of *M. tuberculosis* to cause infection, we used antisense RNA expression to make a mutant of H37Rv with diminished TRX production as outlined in Example 1, calling it H37Rv(pHV203-AS-TRX). Because TRX and TRX reductase are on a polycistronic genetic element, the mutant has diminished production of both factors. When evaluated in an intravascular infection model, H37Rv(pHV203-AS-SOD) exhibited diminished virulence compared to the H37Rv parent and control strains but was more virulent than the antisense-SOD strains [FIG. 6]. It was comparable in attenuation to the antisense-ClpC mutant. On review of lung sections by microscopy, it was observed that H37Rv(pHV203-AS-TRX) induced early interstitial infiltration in manner similar to SOD-diminished H37Rv [FIG. 23]. Furthermore, at 28 days post-infection there was renewed interstitial infiltration in a manner similar to that exhibited by SOD-diminished H37Rv. These results suggest that TRX also inhibits the early innate immune response to infection with *M. tuberculosis*. Similarly, the renewed interstitial infiltration by day 28 might reflect acquired immune responses, possibly including CD8+ T-cell responses such as those induced by BVV.

Although the level of attenuation achieved with H37Rv (pHV203-AS-TRX) was less than that exhibited by BVV, the same reduction in TRX expression could be made in BCG or another attenuated mycobacterial strain to achieve further attenuation and enhance immunogenicity. Therefore, we have constructed isolates of BCG with reduced TRX expression. First, pHV203-AS-TRX was electroporated into BCG Tice to produce BCG(pHV203-AS-TRX). Also, to construct more stable mutants, 4 codons (12 nucleotides) comprising the active-site of TRX (i.e., Cys-Gly-Pro-Cys; amino acids 32 through 35 as numbered in Eklund et al. [Eklund et al., 1991] or amino acids 37 through 40 in SwissProt Accession #P52229 [GI:1729947]) were eliminated in the gene encoding TRX by using PCR-based mutagenesis (Ho et al., 1989). This mutant allele has been electroporated into BCG using the p2NIL/pGOAL19 vector system of Parish and Stoker (Parish and Stoker, 2000) to replace the wild-type gene with the mutant allele. In addition, the gene encoding TRX reductase has been modified in a similar fashion by eliminating the four amino acids comprising the active site (C-A-T-C; amino acids 135 through 138 as numbered in Dai et at [Dai et al., 1996]). Finally, a mutant DNA fragment in which both the TRX 4-codon deletion and the TRX reductase 4-codon deletion are present has been constructed. Each of these mutant genes has been electroporated into BCG to replace the wild-type genes with the mutant alleles.

EXAMPLE 14

Localization of CD8+ T-Cells in Mice Vaccinated with BVV

Figure 16:
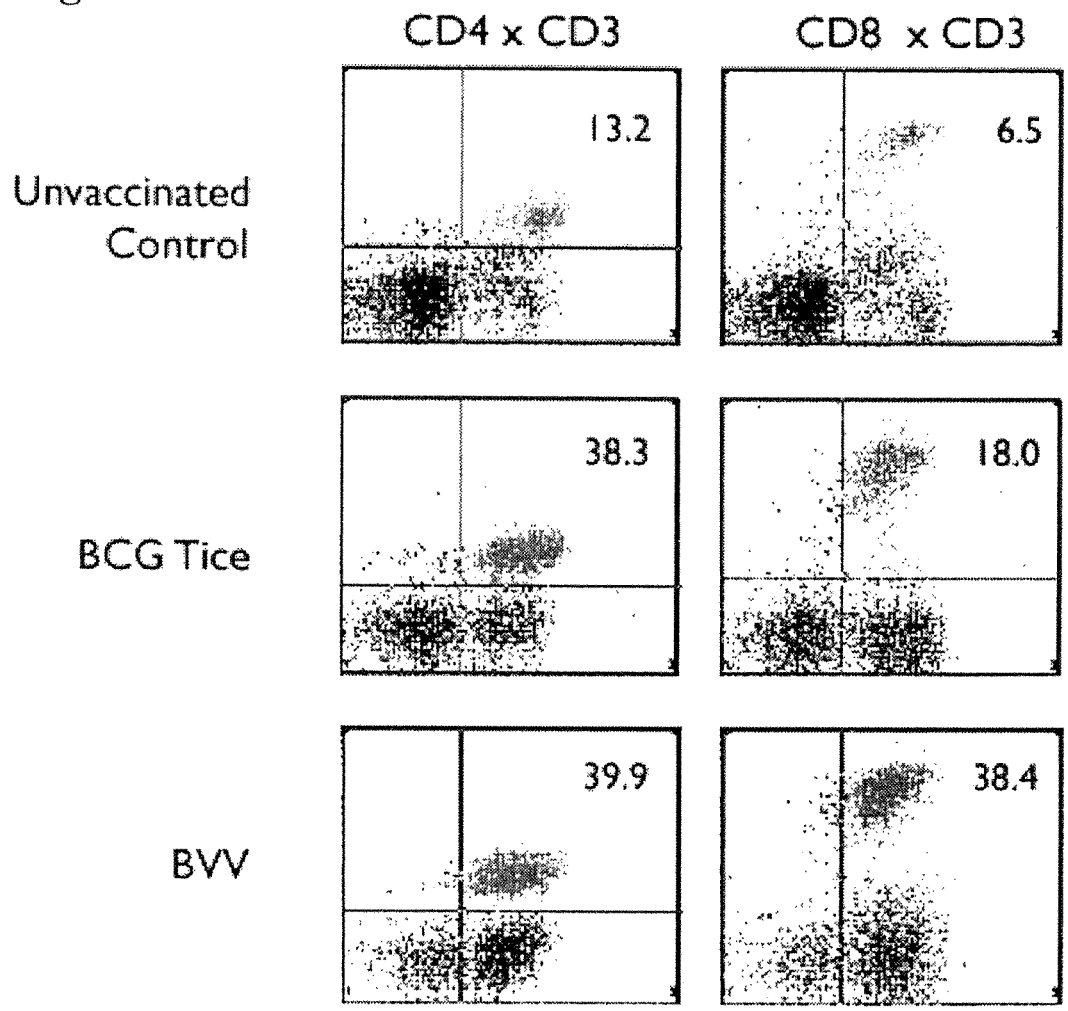

As shown above, vaccination with BVV and vaccination with SOD-diminished BCG induce a higher proportion of CD8+ T-cells among lymphocytes in the lung compared to vaccination with BCG or infection with virulent *M. tuberculosis* H37Rv [Table 4-6, Table 10, FIG. 16]. Also, as CD8+ T-cells are commonly associated with cytotoxic T-lymphocyte (CTL) responses that cause apoptosis via death receptors or perforin/granzyme-based mechanisms, the marked increase in apoptosis in the lung by day 28 post-vaccination [FIG. 8] suggests that these CD8+ T-cells might be involved in the induction of apoptosis.

To determine the location of CD8+ T-cells in the lung tissues of mice vaccinated with BVV versus BCG and strengthen the association between this subpopulation of cells and vaccine efficacy, immunohistochemistry was performed. Formalin-fixed paraffin-embedded sections of the lungs at 17 months post-vaccination from the experiment described in Example 2 [FIGS. 9-12] were cut into 5 μm slices and fixed onto microscope slides utilizing standard procedures. Individual slides were then deparaffinized by immersion of slides into two changes of histology grade p-xylene for 5 minutes each. The slides were then hydrated by sequential 5 minutes immersions into 100%, 95%, and 70% ethanol. The slides were further allowed to hydrate for 90 minutes in PBS. To release antigens from formalin fixation the slides were then microwaved in 1 mM sodium citrate/citric acid buffer for 10 min. Slides then underwent antibody staining using the ImmunoCruz Staining System (Santa Cruz Biochem, UK), using a standard protocol provided by the manufacturer. Rabbit polyclonal anti-mouse CD8 (Cat #sc-7188, Santa Cruz Biochem) was utilized for staining. Slides were blocked with peroxidase block and matching serum to eliminate peroxidase activity and non-specific antibody binding. Slides were counterstained with Mayer's haematoxolin and subsequently mounted with aqueous mounting solution.

Examination of the lung sections showed a much greater number of CD8+ T-cells in the interstitial spaces of mice vaccinated with BVV compared to mice vaccinated with BCG [FIGS. 24 and 25]. Furthermore, the prominent peribronchovascular aggregates of lymphocytes, plasma cells, and macrophages in BVV-infected mice [FIG. 12, Table 2] exhibited strong staining with the anti-CD8 antibody [Table 25], suggesting that these collections of cells are integral to the enhanced CD8+ T-cell responses in BVV-vaccinated and might even be a place where the T-cells are activated to respond to mycobacterial antigens before moving to the interstitial spaces where many of the tubercle bacilli are located. These data provide additional evidence that mice vaccinated with BVV respond to infection by M. tuberculosis with vigorous responses involving both CD4+ and CD8+ T-cells, whereas mice vaccinated with BCG lack a strong CD8+ response.

Throughout this application, various publications are referenced. The disclosures of these publications in their entireties are hereby incorporated by reference into this application in order to more fully describe the state of the art to which this invention pertains.

References

1. Albert, M. L., Sauter, B., and Bhardwaj, N. (1998) Dendritic cells acquire antigen from apoptotic cells and induce class I-restricted CTLs. *Nature* 392: 86-89.
2. Aldovini, A., Husson, R. N., and Young, R. A. (1993) The uraA locus and homologous recombination in *Mycobacterium bovis* BCG. *J. Bacteriol.* 175: 7282-7289.
3. Aliprantis, A. O., Yang, R. B., Weiss, D. S., Godowski, P., and Zychlinsky, A. (2000) The apoptotic signaling pathway activated by Toll-like receptor-2. *EMBO J.* 19: 3325-3336.
4. Arrode, G., Boccaccio, C., Lule, J., Allart, S., Moinard, N., Abastado, J. P., Alam, A., and Davrinche, C. (2000) Incoming human cytomegalovirus pp 65 (UL83) contained in apoptotic infected fibroblasts is cross-presented to CD8(+) T cells by dendritic cells. *J. Virol.* 74: 10018-10024.
5. Bardarov, S., Kriakov, J., Carriere, C., Yu, S., Vaamonde, C., McAdam, R. A., Bloom, B. R., Hatfull, G. F., and Jacobs, W. R., Jr. (1997) Conditionally replicating mycobacteriophages: a system for transposon delivery to *Mycobacterium tuberculosis. Proc. Natl. Acad. Sci. U.S.A* 94: 10961-10966.
6. Beauchamp, C., Fridovich, I. (1971) Superoxide dismutase: improved assays and an assay applicable to acrylamide gels. *Anal. Biochem.* 44: 276-287.
7. Behr, M. A., Wilson, M. A., Gill, W. P., Salamon, H., Schoolnik, G. K., Rane, S., and Small, P. M. (1999) Comparative genomics of BCG vaccines by whole-genome DNA microarray. *Science* 284: 1520-1523.
8. Beyer, W. F., Jr., Fridovich, I. (1987) Assaying for superoxide dismutase activity: some large consequences of minor changes in conditions. *Anal. Biochem.* 161: 559-566.
9. Bravo, J., Mate, M. J., Schneider, T., Switala, J., Wilson, K., Loewen, P. C., and Fita, I. (1999) Structure of catalase HPII from *Escherichia coli* at 1.9 A resolution. *Proteins* 34: 155-166.
10. Brockhaus, F., Brune, B. (1999) Overexpression of CuZn superoxide dismutase protects RAW 264.7 macrophages against nitric oxide cytotoxicity. *Biochem. J.* 338: 295-303.
11. Bunting, K., Cooper, J. B., Badasso, M. O., Tickle, I. J., Newton, M., Wood, S. P., Zhang, Y., and Young, D. (1998) Engineering a change in metal-ion specificity of the iron-dependent superoxide dismutase from *Mycobacterium tuberculosis*—X-ray structure analysis of site-directed mutants. *Eur. J. Biochem.* 251: 795-803.
12. Carlioz, A., Touati, D. (1986) Isolation of superoxide dismutase mutants in *Escherichia coli*: is superoxide dismutase necessary for aerobic life? *EMBO J.* 5: 623-630.
13. Chattergoon, M. A., Kim, J. J., Yang, J. S., Robinson, T. M., Lee, D. J., Dentchev, T., Wilson, D. M., Ayyavoo, V., and Weiner, D. B. (2000) Targeted antigen delivery to antigen-presenting cells including dendritic cells by engineered fas-mediated apoptosis. *Nat. Biotechnol.* 18: 974-979.
14. Cheung, A. L., Eberhardt, K. J., and Fischetti, V. A. (1994) A method to isolate RNA from grain-positive bacteria and mycobacteria. *Anal. Biochem.* 222: 511-514.
15. Cho, S., Mehra, V., Thoma-Uszynski, S., Stenger, S., Serbina, N., Mazzaccaro, R. J., Flynn, J. L., Barnes, P. F., Southwood, S., Celis, E., Bloom, B. R., Modlin, R. L., and Sette, A. (2000) Antimicrobial activity of MHC class I-restricted CD8+ T cells in human tuberculosis. *Proc. Natl. Acad. Sci. U.S.A* 97: 12210-12215.
16. Coleman, J., Green, P. J., and Inouye, M. (1984) The use of RNAs complementary to specific mRNAs to regulate the expression of individual bacterial genes. *Cell* 37: 429436.
17. Collins, F. M., Kelley, C. L., Pavelka, M. S., Jr., and Jacobs, W. R., Jr. Immunogenicity of a lysine auxotroph of *Mycobacterium tuberculosis* H37Rv in a mouse model of human tuberculosis. Abstract 39, In: TB 2000-ASM Conference on Tuberculosis: Past, Present, and Future, New York, N.Y. 2000. Washington, D.C., American Society for Microbiology.
18. Cooksey, R. C., Crawford, J. T., Jacobs, W. R., Jr., and Shinnick, T. M. (1993) A rapid method for screening antimicrobial agents for activities against a strain of *Mycobacterium tuberculosis* expressing firefly luciferase. *Antimicrob. Agents Chemother.* 37: 1348-1352.
19. Cooper, J. B., Driessen, H. P., Wood, S. P., Zhang, Y., and Young, D. (1994) Crystallization and preliminary X-ray analysis of the superoxide dismutase from *Mycobacterium tuberculosis. J. Mol. Biol.* 235: 1156-1158.
20. Cooper, J. B., McIntyre, K., Badasso, M. O., Wood, S. P., Zhang, Y., Garbe, T. R., and Young, D. (1995) X-ray structure analysis of the iron-dependent superoxide dismutase from *Mycobacterium tuberculosis* at 2.0 Angstroms resolution reveals novel dimer-dimer interactions. *J. Mol. Biol.* 246: 531-544.
21. Dai, S., Saarinen, M., Ramaswamy, S., Meyer, Y., Jacquot, J. P., and Eklund, H. (1996) Crystal structure of

*Arabidopsis thaliana* NADPH dependent thioredoxin reductase at 2.5 A resolution. *J. Mol. Biol.* 264: 1044-1057.
22. DasGupta, S. K., Jain, S., Kaushal, D., and Tyagi, A. K. (1998) Expression systems for study of mycobacterial gene regulation and development of recombinant BCG vaccines. *Biochem. Biophys. Res. Commun.* 246: 797-804.
23. Durrbaum-Landmann, I., Gercken, J., Flad, H. D., and Ernst, M. (1996) Effect of in vitro infection of human monocytes with low numbers of *Mycobacterium tuberculosis* bacteria on monocyte apoptosis. *Infect. Immun.* 64: 5384-5389.
24. Dussurget, O., Stewart, G., Neyrolles, O., Pescher, P., Young, D., and Marchal, G. (2001) Role of *Mycobacterium tuberculosis* Copper-Zinc Superoxide Dismutase. *Infect. Immun.* 69: 529-533.
25. Eklund, H., Gleason, F. K., and Holmgren, A. (1991) Structural and functional relations among thioredoxins of different species. Proteins 11: 13-28.
26. Escuyer, V., Haddad, N., Frehel, C., and Berche, P. (1996) Molecular characterization of a surface-exposed superoxide dismutase of *Mycobacterium avium*. *Microb. Pathog.* 20: 41-55.
27. Fan, T., Lu, H., Hu, H., Shi, L., McClarty, G. A., Nance, D. M., Greenberg, A. H., and Zhong, G. (1998) Inhibition of apoptosis in chlamydia-infected cells: blockade of mitochondrial cytochrome c release and caspase activation. *J. Exp. Med.* 187: 487-496.
28. Fang, F. C., DeGroote, M. A., Foster, J. W., Baumler, A. J., Ochsner, U., Testerman, T., Bearson, S., Giard, J. C., Xu, Y., Campbell, G., and Laessig, T. (1999) Virulent *Salmonella typhimurium* has two periplasmic Cu, Zn-superoxide dismutases. *Proc. Natl. Acad. Sci. U.S.A* 96: 7502-7507.
29. Florio, W., Freer, G., Daila, C. B., Batoni, G., Maisetta, G., Senesi, S., and Campa, M. (1997) Comparative analysis of subcellular distribution of protein antigens in *Mycobacterium bovis bacillus* Calmette-Guerin. *Can. J. Microbiol.* 43: 744-750.
30. Flynn, J. L., Goldstein, M. M., Triebold, K. J., Koller, B., and Bloom, B. R. (1992) Major histocompatibility complex class I-restricted T cells are required for resistance to *Mycobacterium tuberculosis* infection. *Proc. Natl. Acad. Sci. U.S.A* 89: 12013-12017.
31. Forest, K. T., Langford, P. R., Kroll, J. S., and Getzoff, E. D. (2000) Cu,Zn superoxide dismutase structure from a microbial pathogen establishes a class with a conserved dimer interface. *J. Mol. Biol.* 296: 145-153.
32. Fratazzi, C., Arbeit, R. D., Carini, C., Balcewicz-Sablinska, M. K., Keane, J., Kornfeld, H., and Remold, H. G. (1999) Macrophage apoptosis in mycobacterial infections. *J. Leukoc. Biol.* 66: 763-764.
33. Gao, L., Abu, K. Y. (2000) Hijacking of apoptotic pathways by bacterial pathogens. *Microbes. Infect.* 2: 1705-1719.
34. Gill, H. S., Pfluegl, G. M., and Eisenberg, D. (1999) Preliminary crystallographic studies on glutamine synthetase from *Mycobacterium tuberculosis. Acta Crystallogr. D. Biol. Crystallogr.* 55 (Pt 4): 865-868.
35. Gouet, P., Jouve, H. M., and Dideberg, O. (1995) Crystal structure of *Proteus mirabilis* PR catalase with and without bound NADPH. *J. Mol. Biol.* 249: 933-954.
36. Hanahan, D. (1983) Studies on transformation of *Escherichia coli* with plasmids *J. Mol. Biol.* 166: 557-580.
37. Harth, G., Horwitz, M. A. (1999) Export of recombinant *Mycobacterium tuberculosis* superoxide dismutase is dependent upon both information in the protein and mycobacterial export machinery. A model for studying export of leaderless proteins by pathogenic mycobacteria. *J. Biol. Chem.* 274: 4281-4292.
38. Henry, F., Boisteau, O., Bretaudeau, L., Lieubeau, B., Meflah, K., and Gregoire, M. (1999) Antigen-presenting cells that phagocytose apoptotic tumor-derived cells are potent tumor vaccines. *Cancer Res.* 59: 3329-3332.
39. Hess, J., Miko, D., Catic, A., Lehmensiek, V., Russell, D. G., and Kaufmann, S. H. (1998) *Mycobacterium bovis* Bacille Calmette-Guerin strains secreting listeriolysin of *Listeria monocytogenes. Proc. Natl. Acad. Sci. U.S.A* 95: 5299-5304.
40. Ho, S. N., Hunt, H. D., Horton, R. M., Pullen, J. K., and Pease, L. R. (1989) Site-directed mutagenesis by overlap extension using the polymerase chain reaction. *Gene* 77: 51-59.
41. Hondalus, M. K., Bardarov, S., Russell, R., Chan, J., Jacobs, W. R., Jr., and Bloom, B. R. (2000) Attenuation of and protection induced by a leucine auxotroph of *Mycobacterium tuberculosis. Infect. Immun.* 68: 2888-2898.
42. Howard, N. S., Gomez, J. E., Ko, C., and Bishai, W. R. (1995) Color selection with a hygromycin-resistance-based *Escherichia coli*-mycobacterial shuttle vector Gene 166: 181-182.
43. Igwe, E. I., Russmann, H., Roggenkamp, A., NoLL, A., Autenrieth, I. B., and Heesemann, J. (1999) Rational live oral carrier vaccine design by mutating virulence-associated genes of *Yersinia enterocolitica. Infect. Immun.* 67: 5500-5507.
44. Jabs, T. (1999) Reactive oxygen intermediates as mediators of programmed cell death in plants and animals. *Biochem. Pharmacol.* 57: 231-245.
45. Jackson, M., Phalen, S. W., Lagranderie, M., Ensergueix, D., Chavarot, P., Marchal, G., McMurray, D. N., Gicquel, B., and Guilhot, C. (1999) Persistence and protective efficacy of a *Mycobacterium tuberculosis* auxotroph vaccine. *Infect. Immun.* 67: 2867-2873.
46. Jackson, S. M., Cooper, J. B. (1998) An analysis of structural similarity in the iron and manganese superoxide dismutases based on known structures and sequences. *Biometals* 11: 159-173.
47. Kaufmann, S. H. (2000) Is the development of a new tuberculosis vaccine possible? *Nat. Med.* 6: 955-960.
48. Keane, J., Remold, H. G., and Kornfeld, H. (2000) Virulent *Mycobacterium tuberculosis* strains evade apoptosis of infected alveolar macrophages. *J. Immunol.* 164: 2016-2020.
49. Kernodle, D. S., Voladri, R. K., Menzies, B. E., Hager, C. C., and Edwards, K. M. (1997) Expression of an antisense hla fragment in *Staphylococcus aureus* reduces α-toxin production in vitro and attenuates lethal activity in a murine model. *Infect. Immun.* 65: 179-184.
50. Kornfeld, H., Mancino, G., and Colizzi, V. (1999) The role of macrophage cell death in tuberculosis. *Cell Death. Differ.* 6: 71-78.
51. Kovarova, H., Hajduch, M., and Macela, A. (1997) Natural resistance to infection with intracellular pathogens: cross-talk between Nramp1 and Lps genes. *Electrophoresis* 18: 2654-2660.
52. Kovarova, H., Radzioch, D., Hajduch, M., Sirova, M., Blaha, V., Macela, A., Stulik, J., and Hernychova, L. (1998) Natural resistance to intracellular parasites: a study by two-dimensional gel electrophoresis coupled with multivariate analysis. *Electrophoresis* 19: 1325-1331.
53. Kusunose, E., Ichihara, K., Noda, Y., and Kusunose, M. (1976) Superoxide dismutase from *Mycobacterium tuberculosis*. *J. Biochem. (Tokyo)* 80:1343-1352.
54. Lah, M. S., Dixon, M. M., Pattridge, K. A., Stallings, W. C., Fee, J. A., and Ludwig, M. L. (1995) Structure-function in *Escherichia coli* iron superoxide dismutase: comparisons with the manganese enzyme from *Thermus thermophilus*. *Biochemistry (Mosc)*. 34: 1646-1660.
55. Lakey, D. L., Voladri, R. K., Edwards, K. M., Hager, C., Samten, B., Wallis, R. S., Barnes, P. F., and Kernodle, D. S. (2000) Enhanced production of recombinant *Mycobacterium tuberculosis* antigens in *Escherichia coli* by replacement of low-usage codons. *Infect. Immun.* 68: 233-238.
56. Lalvani, A., Brookes, R., Wilkinson, R. J., Malin, A. S., Pathan, A. A., Andersen, P., Dockrell, H., Pasvol, G., and Hill, A. V. (1998) Human cytolytic and interferon gamma-secreting CD8+ T lymphocytes specific for *Mycobacterium tuberculosis Proc. Natl. Acad. Sci. U.S.A* 95: 270-275.
57. Lau, L. L., Jamieson, B. D., Somasundaram, T., and Ahmed, R. (1994) Cytotoxic T-cell memory without antigen. *Nature* 369: 648-652.
58. Lee, M. H., Pascopella, L., Jacobs, W. R., Jr., and Hatfull, G. F. (1991) Site-specific integration of mycobacteriophage L5: integration-proficient vectors for *Mycobacterium smegmatis, Mycobacteriunz tuberculosis*, and bacille Calmette-Guerin. *Proc. Natl. Acad. Sci. U.S.A* 88: 3111-3115.
59. Levdikov, V. M., Barynin, V. V., Grebenko, A. I., Melik-Adamyan, W. R., Lamzin, V. S., and Wilson, K. S. (1998) The structure of SAICAR synthase: an enzyme in the de novo pathway of purine nucleotide biosynthesis. *Structure*. 6: 363-376.
60. Liaw, S. H., Eisenberg, D. (1994) Structural model for the reaction mechanism of glutamine synthetase, based on five crystal structures of enzyme-substrate complexes. *Biochemistry (Mosc)*. 33: 675-681.
61. McAdam, R. A., Weisbrod, T. R., Martin, J., Scuderi, J. D., Brown, A. M., Cirillo, J. D., Bloom, B. R., and Jacobs, W. R., Jr. (1995) In vivo growth characteristics of leucine and methionine auxotrophic mutants of *Mycobacterium bovis* BCG generated by transposon mutagenesis. *Infect. Immun.* 63: 1004-1012.
62. Means, T. K., Wang, S., Lien, E., Yoshimura, A., Golenbock, D. T., and Fenton, M. J. (1999) Human toll-like receptors mediate cellular activation by *Mycobacterium tuberculosis*. *J. Immunol.* 163: 3920-3927.
63. Melcher, A., Gough, M., Todryk, S., and Vile, R. (1999) Apoptosis or necrosis for tumor immunotherapy: what's in a name? *J. Mol. Med.* 77: 824-833.
64. Menendez, M. C., Domenech, P., Prieto, J., and Garcia, M. J. (1995) Cloning and expression of the *Mycobacterium fortuitum* superoxide dismutase gene. *FEMS Microbiol. Lett.* 134: 273-278.
65. Mittl, P. R., Schulz, G. E. (1994) Structure of glutathione reductase (glutaredoxin) from *Escherichia coli* at 1.86 A resolution: comparison with the enzyme from human erythrocytes. *Protein Sci.* 3: 799-809.
66. Molloy, A., Laochumroonvorapong, P., and Kaplan, G. (1994) Apoptosis, but not necrosis, of infected monocytes is coupled with killing of intracellular bacillus Calmette-Guerin. *J. Exp. Med.* 180: 1499-1509.
67. Moore, K. J., Matlashewski, G. (1994) Intracellular infection by *Leishmania donovani* inhibits macrophage apoptosis. *J. Immunol.* 152: 2930-2937.
68. Murray, C. J., Salomon, J. A. (1998) Modeling the impact of global tuberculosis control strategies. *Proc. Natl. Acad. Sci. U.S.A* 95: 13881-13886.
69. Nair, S., Milohanic, E., and Berche, P. (2000) ClpC ATPase is required for cell adhesion and invasion of *Listeria monocytogenes*. *Infect. Immun.* 68: 7061-7068.
70. Nash, P. B., Purner, M. B., Leon, R. P., Clarke, P., Duke, R. C., and Curiel, T. J. (1998) *Toxoplasma gondii*-infected cells are resistant to multiple inducers of apoptosis. *J. Immunol.* 160: 1824-1830.
71. North, R. J., LaCourse, R., and Ryan, L. (1999) Vaccinated mice remain more susceptible to *Mycobacterium tuberculosis* infection initiated via the respiratory route than via the intravenous route. *Infect. Immun.* 67: 2010-2012.
72. Nouri-Shirazi, M., Banchereau, J., Fay, J., and Palucka, K. (2000) Dendritic cell based tumor vaccines *Immunol. Lett.* 74: 5-10.
73. Oddo, M., Renno, T., Attinger, A., Bakker, T., MacDonald, H. R., and Meylan, P. R. (1998) Fas ligand-induced apoptosis of infected human macrophages reduces the viability of intracellular *Mycobacterium tuberculosis*. *J. Immunol.* 160: 5448-5454.
74. Ostermeier, M., Nixon, A. E., and Benkovic, S. J. (1999) Incremental truncation as a strategy in the engineering of novel biocatalysts. *Bioorg. Med. Chem.* 7: 2139-2144.
75. Papaconstantinou, H. T., Chung, D. H., Zhang, W., Ansari, N. H., Hellmich, M. R., Townsend, C. M., Jr., and Ko, T. C. (2000) Prevention of mucosal atrophy: role of glutamine and caspases in apoptosis in intestinal epithelial cells. *J. Gastrointest. Surg.* 4: 416-423.
76. Parish, T., Stoker, N. G. (2000) Use of a flexible cassette method to generate a double unmarked *Mycobacterium tuberculosis* tlyA plcABC mutant by gene replacement. *Microbiology* 146: 1969-1975.
77. Pathan, A. A., Wilkinson, K. A., Wilkinson, R. J., Latif, M., McShane, H., Pasvol, G., Hill, A. V., and Lalvani, A. (2000) High frequencies of circulating IFN-gamma-secreting CD8 cytotoxic T cells specific for a novel MHC class I-restricted *Mycobacterium tuberculosis* epitope in *M. tuberculosis*-infected subjects without disease *Eur. J. Immunol.* 30: 2713-2721.
78. Pelicic, V., Jackson, M., Reyrat, J. M., Jacobs, W. R., Jr., Gicquel, B., and Guilhot, C. (1997) Efficient allelic exchange and transposon mutagenesis in *Mycobacterium tuberculosis*. *Proc. Natl. Acad. Sci. U.S.A* 94: 10955-10960.
79. Pesce, A., Battistoni, A., Stroppolo, M. E., Polizio, F., Nardini, M., Kroll, J. S., Langford, P. R., Sette, M., Desideri, A., and Bolognesi, M. (2000) Functional and crystallographic characterization of *Salmonella typhimurium* Cu,Zn superoxide dismutase coded by the sodCI virulence gene. *J. Mol. Biol.* 302: 465-478.
80. Powis, G., Briehl, M., and Oblong, J. (1995) Redox signalling and the control of cell growth and death. *Pharmacol. Ther.* 68: 149-173.
81. Raynaud, C., Etienne, G., Peyron, P., Laneelle, M. A., and Daffe, M. (1998) Extracellular enzyme activities potentially involved in the pathogenicity of *Mycobacterium tuberculosis*. *Microbiology* 144: 577-587.

82. Restifo, N. P. (2000) Building better vaccines: how apoptotic cell death can induce inflammation and activate innate and adaptive immunity *Curr. Opin. Immunol.* 12: 597-603.
83. Rojas, M., Barrera, L. F., Puzo, G., and Garcia, L. F. (1997) Differential induction of apoptosis by virulent *Mycobacterium tuberculosis* in resistant and susceptible murine macrophages: role of nitric oxide and mycobacterial products. *J. Immunol.* 159: 1352-1361.
84. Rojas, M., Olivier, M., Gros, P., Barrera, L. F., and Garcia, L. F. (1999) TNF-alpha and IL-10 modulate the induction of apoptosis by virulent *Mycobacterium tuberculosis* in murine macrophages. *J. Immunol.* 162: 6122-6131.
85. Rouquette, C., de Chastellier, C., Nair, S., and Berche, P. (1998) The ClpC ATPase of *Listeria monocytogenes* is a general stress protein required for virulence and promoting early bacterial escape from the phagosome of macrophages. *Mol. Microbiol.* 27: 1235-1245.
86. Sadosky, A. B., Wilson, J. W., Steinman, H. M., and Shuman, H. A. (1994) The iron superoxide dismutase of *Legionella pneumophila* is essential for viability. *J. Bacteriol.* 176: 3790-3799.
87. Saitoh, M., Nishitoh, H., Fujii, M., Takeda, K., Tobiume, K., Sawada, Y., Kawabata, M., Miyazono, K., and Ichijo, H. (1998) Mammalian thioredoxin is a direct inhibitor of apoptosis signal-regulating kinase (ASK) 1. *EMBO J.* 17: 2596-2606.
88. Seder, R. A., Hill, A. V. (2000) Vaccines against intracellular infections requiring cellular immunity *Nature* 406: 793-798.
89. Serbina, N. V., Flynn, J. L. (1999) Early emergence of CD8(+) T cells primed for production of type 1 cytokines in the lungs of *Mycobacterium tuberculosis*-infected mice. *Infect. Immun.* 67: 3980-3988.
90. Serbina, N. V., Liu, C. C., Scanga, C. A., and Flynn, J. L. (2000) CD8+CTL from lungs of *Mycobacterium tuberculosis*-infected mice express perforin in vivo and lyse infected macrophages. *J. Immunol.* 165: 353-363.
91. Shinnick, T. M. (1987) The 65-kilodalton antigen of *Mycobacterium tuberculosis*. *J. Bacteriol.* 169: 1080-1088.
92. Shrivastava, A., Aggarwal, B. B. (1999) Antioxidants differentially regulate activation of nuclear factor-kappa B, activator protein-1, c-jun amino-terminal kinases, and apoptosis induced by tumor necrosis factor: evidence that JNK and NF-kappa B activation are not linked to apoptosis. *Antioxid. Redox. Signal.* 1: 181-191.
93. Silva, C. L., Bonato, V. L., Lima, V. M., Faccioli, L. H., and Leao, S. C. (1999) Characterization of the memory/activated T cells that mediate the long-lived host response against tuberculosis after *bacillus* Calmette-Guerin or DNA vaccination. *Immunology* 97: 573-581.
94. Slauch, J. M., Mahan, M. J., and Mekalanos, J. J. (1994) In vivo expression technology for selection of bacterial genes specifically induced in host tissues. *Methods Enzymol.* 235: 481-492.
95. Snider, D. E., Jr., La Montagne, J. R. (1994) The neglected global tuberculosis problem: a report of the 1992 World Congress on Tuberculosis. *J. Infect. Dis.* 169: 1189-1196.
96. Sousa, A. O., Mazzaccaro, R. J., Russell, R. G., Lee, F. K., Turner, O. C., Hong, S., Van Kaer, L., and Bloom, B. R. (2000) Relative contributions of distinct MHC class I-dependent cell populations in protection to tuberculosis infection in mice. *Proc. Natl. Acad. Sci. U.S.A* 97: 4204-4208.
97. Tarte, K., Klein, B. (1999) Dendritic cell-based vaccine: a promising approach for cancer immunotherapy. *Leukemia* 13: 653-663.
98. Tsuji, S., Matsumoto, M., Takeuchi, O., Akira, S., Azuma, I., Hayashi, A., Toyoshima, K., and Seya, T. (2000) Maturation of human dendritic cells by cell wall skeleton of *Mycobacterium bovis bacillus* Calmette-Guerin: involvement of toll-like receptors. *Infect. Immun.* 68: 6883-6890.
99. Tumani, H., Smirnov, A., Barchfeld, S., Olgemoller, U., Maier, K., Lange, P., Bruck, W., and Nau, R. (2000) Inhibition of glutamine synthetase in rabbit pneumococcal meningitis is associated with neuronal apoptosis in the dentate gyms. *Glia* 30: 11-18.
100. Ursby, T., Adinolfi, B. S., Al Karadaghi, S., De Vendittis, E., and Bocchini, V. (1999) Iron superoxide dismutase from the archaeon *Sulfolobus solfataricus*: analysis of structure and thermostability. *J. Mol. Biol.* 286: 189-205.
101. van Soolingen, D., Hermans, P. W., de Haas, P. E., Soll, D. R., and van Embden, J. D. (1991) Occurrence and stability of insertion sequences in *Mycobacterium tuberculosis* complex strains: evaluation of an insertion sequence-dependent DNA polymorphism as a tool in the epidemiology of tuberculosis. *J. Clin. Microbiol.* 29: 2578-2586.
102. Venketeraman, V., Fratti, R., Boucher, J. C., Mudd, M., Poschet, J., and Deretic, V. Mechanisms of 1,25-dihydroxyvitamin $D_3$ (calcitriol) action in control of *Mycobacterium tuberculosis*. Abstract 217, In: TB 2000-ASM Conference on Tuberculosis: Past, Present, and Future, New York, N.Y. 2000. Washington, D.C., American Society for Microbiology.
103. Wang, S., Leonard, S. S., Castranova, V., Vallyathan, V., and Shi, X. (1999) The role of superoxide radical in TNF-alpha induced NF-kappaB activation. *Ann. Clin. Lab Sci.* 29: 192-199.
104. Wick, M. J., Ljunggren, H. G. (1999) Processing of bacterial antigens for peptide presentation on MHC class I molecules. *Immunol. Rev.* 172: 153-162.
105. Wieles, B., Nagai, S., Wiker, H. G., Harboe, M., and Ottenhoff, T. H. (1995) Identification and functional characterization of thioredoxin of *Mycobacterium tuberculosis*. *Infect. Immun.* 63: 4946-4948.
106. Wieles, B., Ottenhoff, T. H., Steenwijk, T. M., Franken, K. L., de Vries, R. R., and Langermans, J. A. (1997) Increased intracellular survival of *Mycobacterium smegmatis* containing the *Mycobacterium leprae* thioredoxin-thioredoxin reductase gene. *Infect. Immun.* 65: 2537-2541.
107. Wilson, T., de Lisle, G. W., Marcinkeviciene, J. A., Blanchard, J. S., and Collins, D. M. (1998) Antisense RNA to ahpC, an oxidative stress defense gene involved in isoniazid resistance, indicates that AhpC of *Mycobacterium bovis* has virulence properties. *Microbiology* 144: 2687-2695.
108. Yrlid, U., Wick, M. J. (2000) *Salmonella*-induced apoptosis of infected macrophages results in presentation of a bacteria-encoded antigen after uptake by bystander dendritic cells. *J. Exp. Med.* 191: 613-624.
109. Zhang, Y., Garcia, M. J., Lathigra, R., Allen, B., Moreno, C., van Embden, J. D., and Young, D. (1992) Alterations in the superoxide dismutase gene of an isoniazid-resistant strain of *Mycobacterium tuberculosis*. *Infect. Immun.* 60: 2160-2165.
110. Zhang, Y., Lathigra, R., Garbe, T., Catty, D., and Young, D. (1991) Genetic analysis of superoxide dismutase, the 23 kilodalton antigen of *Mycobacterium tuberculosis*. *Mol. Microbiol.* 5: 381-391.

111. De Groote, M. A., Ochsner, U. A., Shiloh, M. U., Nathan, C., McCord, J. M., Dinauer, M. C., Libby, S. J., Vazquez-Torres, A., Xu, Y., and Fang, F. C. (1997) Periplasmic superoxide dismutase protects *Salmonella* from products of phagocyte NADPH-oxidase and nitric oxide synthase. *Proc. Natl. Acad. Sci. U.S.A.* 94: 13997-14001.

112. Farrant, J. L., Sansone, A., Canvin, J. R., Pallen, M. J., Langford, P. R., Wallis, T. S., Dougan, G., and Kroll, J. S. (1997) Bacterial copper- and zinc-cofactored superoxide dismutase contributes to the pathogenesis of systemic salmonellosis. *Mol. Microbiol.* 25: 785-796.

113. Franzon, V. L., Arondel, J., and Sansonetti, P. J. (1990) Contribution of superoxide dismutase and catalase activities to *Shigella flexneri* pathogenesis. *Infect. Immun.* 58: 529-535.

114. Funanage, V. L., Brenchley, J. E. (1977) Characterization of *Salmonella typhimurium* mutants with altered glutamine synthetase activity. *Genetics* 86: 513-526.

115. Harth, G., Zamecnik, P. C., Tang, J. Y., Tabatadze, D., and Horwitz, M. A. (2000) Treatment of *Mycobacterium tuberculosis* with antisense oligonucleotides to glutamine synthetase mRNA inhibits glutamine synthetase activity, formation of the poly-L-glutamate/glutamine cell wall structure, and bacterial replication. *Proc. Natl. Acad. Sci. U.S.A* 97: 418-423.

116. Klose, K. E., Mekalanos, J. J. (1997) Simultaneous prevention of glutamine synthesis and high-affinity transport attenuates *Salmonella typhimurium* virulence. *Infect. Immun.* 65: 587-596.

117. Latimer, E., Simmers, J., Sriranganathan, N., Roop, R. M., Schurig, G. G., and Boyle, S. M. (1992) *Brucella abortus* deficient in copper/zinc superoxide dismutase is virulent in BALB/c mice. *Microb. Pathog.* 12: 105-113.

118. Sheehan, B. J., Langford, P. R., Rycroft, A. N., and Kroll, J. S. (2000) [Cu,Zn]-Superoxide dismutase mutants of the swine pathogen *Actinobacillus* pleuropneumoniae are unattenuated in infections of the natural host. *Infect. Immun.* 68: 4778-4781.

119. St John, G., Steinman, H. M. (1996) Periplasmic copper-zinc superoxide dismutase of *Legionella pneumophila*: role in stationary-phase survival. *J. Bacteriol.* 178: 1578-1584.

120. Storz, G., Tartaglia, L. A. (1992) OxyR: a regulator of antioxidant genes *J. Nutr.* 122: 627-630.

121. Tatum, F. M., Detilleux, P. G., Sacks, J. M., and Halling, S. M. (1992) Construction of Cu—Zn superoxide dismutase deletion mutants of *Brucella abortus*: analysis of survival in vitro in epithelial and phagocytic cells and in vivo in mice. *Infect. Immun.* 60: 2863-2869.

122. Tsolis, R. M., Baumler, A. J., and Heffron, F. (1995) Role of *Salmonella typhimurium* Mn-superoxide dismutase (SodA) in protection against early killing by J774 macrophages. *Infect. Immun.* 63: 1739-1744.

123. Brooks, D. R., McCulloch, R., Coombs, G. H., and Mottram, J. C. (2000) Stable transformation of trypanosomatids through targeted chromosomal integration of the selectable marker gene encoding blasticidin S deaminase. *FEMS Microbiol. Lett.* 186: 287-291.

124. Charest, H., Sedegah, M., Yap, G. S., Gazzinelli, R. T., Caspar, P., Hoffman, S. L., and Sher, A. (2000) Recombinant attenuated *Toxoplasma gondii* expressing the *Plasmodium yoelii* circumsporozoite protein provides highly effective priming for CD8+ T cell-dependent protective immunity against malaria. *J. Immunol.* 165: 2084-2092.

125. Chiang, C. W., Carter, N., Sullivan, W. J., Jr., Donald, R. G., Roos, D. S., Naguib, F. N., el Kouni, M. H., Ullman, B., and Wilson, C. M. (1999) The adenosine transporter of *Toxoplasma gondii*. Identification by insertional mutagenesis, cloning, and recombinant expression. *J. Biol. Chem.* 274: 35255-35261.

126. Dumas, C., Ouellette, M., Tovar, J., Cunningham, M. L., Fairlamb, A. H., Tamar, S., Olivier, M., and Papadopoulou, B. (1997) Disruption of the trypanothione reductase gene of *Leishmania* decreases its ability to survive oxidative stress in macrophages. *EMBO J.* 16: 2590-2598.

127. Durbin, A. P., McAuliffe, J. M., Collins, P. L., and Murphy, B. R. (1999) Mutations in the C, D, and V open reading frames of human parainfluenza virus type 3 attenuate replication in rodents and primates. Virology 261: 319-330.

128. Enloe, B., Diamond, A., and Mitchell, A. P. (2000) A single-transformation gene function test in diploid *Candida albicans*. *J. Bacteriol.* 182: 5730-5736.

129. Heider, J. A., Yu, Y., Shenk, T., and Alwine, J. C. (2002) Characterization of a human cytomegalovirus with phosphorylation site mutations in the immediate-early 2 protein. *J. Virol.* 76: 928-932.

130. Odberg-Ferragut, C., Renault, J. P., Viscogliosi, E., Toursel, C., Briche, I., Engels, A., Lepage, G., Morgenstern-Badarau, I., Camus, D., Tomavo, S., and Dive, D. (2000) Molecular cloning, expression analysis and iron metal cofactor characterisation of a superoxide dismutase from *Toxoplasma gondii*. *Mol. Biochem. Parasitol.* 106: 121-129.

131. Retallack, D. M., Heinecke, E. L., Gibbons, R., Deepe, G. S., Jr., and Woods, J. P. (1999) The URA5 gene is necessary for *Histoplasma capsulatum* growth during infection of mouse and human cells. *Infect. Immun.* 67: 624-629.

132. Varma, A., Kwon-Chung, K. J. (2000) Characterization of the L41 gene in *Cryptococcus neoformans*: its application as a selectable transformation marker for cycloheximide resistance. *Yeast* 16: 1397-1403.

133. Wilson, R. B., Davis, D., Enloe, B. M., and Mitchell, A. P. (2000) A recyclable *Candida albicans* URA3 cassette for PCR product-directed gene disruptions. *Yeast* 16: 65-70.

134. Woods, J. P., Heinecke, E. L., and Goldman, W. E. (1998) Electrotransformation and expression of bacterial genes encoding hygromycin phosphotransferase and beta-galactosidase in the pathogenic fungus *Histoplasma capsulatum*. *Infect. Immun.* 66: 1697-1707.

TABLE 1

Bacterial strains and plasmids used

| Strain or plasmid | Description | Reference or source |
|---|---|---|
| Strains | | |
| mc²155 | *M. smegmatis* strain | William Jacobs Jr; Albert Einstein School of Medicine (Cooksey, Crawford, Jacobs, Jr., and Shinnick, 1993) |
| H37Rv | virulent *M. tuberculosis* reference strain | ATCC 25618 |
| DH5α | *E. coli* host strain | (Hanahan, 1983) |

TABLE 1-continued

Bacterial strains and plasmids used

| Strain or plasmid | Description | Reference or source |
|---|---|---|
| BCG Tice | *Bacillus* Calmette-Guérin, substrain Tice | Organon Teknika Corp., Durham NC |
| CK9C1891 | SOD-deficient *E. coli* strain | Danielle Touati, Institut Jacques Monod, Paris |
| Plasmids | | |
| PBC SK+ pY6002 | *E. coli* phagemid vector plasmid containing aph gene from Tn903, which confers resistance to kanamycin | Stratagene, La Jolla, CA Richard Young, MIT (Aldovini, Husson, and Young, 1993) |
| PBAK14 | *E. coli*-mycobacterial shuttle plasmid containing the origin of replication from the M. fortuitum_plasmid pAL5000 | Douglas Young, Hammersmith Hospital, London (Zhang, Lathigra, Garbe, Catty, and Young, 1991) |
| PHV202* | *E. coli*-mycobacterial shuttle plasmid containing multicloning site behind Pr-HSP | this study |
| PHV202-AS-SOD | pHV202 containing a 151-bp fragment of sodA cloned in an antisense orientation behind Pr-HSP | this study |
| PLUC10 | *E. coli*-mycobacterial shuttle plasmid containing firefly luciferase gene | Robert Cooksey, Centers for Disease Control, Atlanta, GA (Cooksey, Crawford, Jacobs, Jr., and Shinnick, 1993) |
| pLUC10-AS-SOD | pLUC10 containing a 151-bp fragment of sodA cloned in an antisense orientation behind Pr-HSP orientation behind Pr-HSP | this study |
| p16R1 | *E. coli*-mycobacterial shuttle plasmid for expressing SOD in mycobacteria | Douglas Young, Hammersmith Hospital, London |
| pKK233-2 | Expression plasmid yielding recombinant proteins without fusion tag | Pharmacia |
| pNBV-1 | *E. coli*-mycobacterial shuttle vector | {Howard, Gomez, et al. 1995 370 /id} |
| p1NIL, p2NIL, pGOAL17, pGOAL19 | Plasmid vectors for use in allelic replacement in *M. tuberculosis* | {Parish & Stoker 2000 267 /id} |

Pr-HSP = the promoter of the 65-kDa heat-shock protein of *M. tuberculosis*

*Note: the terms pHV202 and pHV203 are used interchangeably: pHV203 was derived from pHV202 by repairing a mutation in the promoter region of the 65 kDa heat-shock protein that drives expression of the antisense fragment.

TABLE 2

Histopathologic scores of murine lungs seventeen months post-inoculation*

| Site of Infiltrate | BCG Tice | H37Rv(pLUC10-AS-SOD) | P value |
|---|---|---|---|
| Interstitial | 1.9 | 1.4 | 0.25 |
| Peribronchiolar | 0.9 | 0.7 | 0.45 |
| Alveolar | 2.0 | 1.0 | <.01 |
| Perivascular | 1.6 | 2.4 | <.01 |

*Lung sections from each mouse were examined microscopically and infiltration was scored on a scale of 0 to 3. Results represent mean values of determinations from eleven and twelve mice infected with BCG and H37Rv(pLUC10-AS-SOD), respectively. P values were determined using Mann-Whitney nonparametric analysis.

TABLE 3

Antibodies and Conditions used for FACS

| Antibody | Fluorochrome | Manufacturer | Amount/sample |
|---|---|---|---|
| Lymphocyte Analysis | | | |
| anti-CD3 | APC | BD Pharmingen | 0.8 ug |
| anti-CD4 | FITC or Cychrome | BD Pharmingen | 0.8 ug |
| anti-CD8 | PE | BD Pharmingen | 0.8 ug |
| anti-NK1.1 | FITC or PE | BD Pharmingen | 1 ug |
| anti-B220 | PerCP | BD Pharmingen | 0.8 ug |
| Granulocyte analysis | | | |
| anti-Ly6 | PE | BD Pharmingen | 1 ug |
| Monocyte analysis | | | |
| anti-F4/80 | FITC | Serotec | 10 ul |
| Dendritic cell analysis | | | |
| anti-Cd11c | FITC | BD Pharmingen | 1 ug |
| anti-CD80 | PE | BD Pharmingen | 0.8 ug |
| anti-Class I-a | PE | BD Pharmingen | 0.8 ug |
| Isotype Controls | | | |
| anti-Rat IgG2bk | APC | BD Pharmingen | 0.8 ug |
| anti-Rat IgG2ak | PerCP or PE | BD Pharmingen | 0.8 ug |
| anti-Hamster IgGk | FITC | BD Pharmingen | 1 ug |
| anti-Hamster IgGl | FITC | BD Pharmingen | 1 ug |
| anti-Mouse IgG2ak | Cychrome | BD Pharmingen | 0.8 ug |

In all cases the samples were incubated with Rat anti Mouse anti-CD16 (Fc Block, BD Pharmingen) for 15 minutes as directed to maintain as minimal a background as possible. In addition, in some experiments, 7AAD (BD Pharmingen) was used to evaluate viability.

TABLE 4

T-lymphocyte populations in lungs harvested from mice vaccinated with BCG Tice versus BVV at one day following pulmonary challenge with the virulent Erdman strain of *M. tuberculosis*:

| Vaccination Group | Mouse No. | CD4% | CD8% |
|---|---|---|---|
| BCG vaccinated, Erdman challenged | 1 | 24.1 | 15.8 |
| | 2 | 30 | 17 |
| H37Rv (pHV203-AS-SOD) vaccinated, Erdman challenged | 1 | 36.3 | 27.2 |
| | 2 | 44 | 23.6 |
| H37Rv (pLUC10-AS-SOD) vaccinated, Erdman challenged | 1 | 30.1 | 26.8 |
| | 2 | 33 | 14.2 |
| Unvaccinated, Erdman challenged | 1 | 20.8 | 17.8 |
| Unvaccinated, Unchallenged | 1 | 21 | 11.1 |

Single cell suspensions (SCS) were harvested at 9 week post-vaccination, and mice had been challenged with $5 \times 10^4$ of the virulent Erdman strain of *M. tuberculosis* via intranasal administration 24 hours before cells were harvested. FACS was performed using a lymphocyte gate.

TABLE 5

T-lymphocyte populations in lungs harvested from mice vaccinated with BCG Tice versus BVV at one month post-vaccination

| Vaccination Group | CD4% | CD8% |
|---|---|---|
| H37Rv (pLUC10-AS-SOD) | 33 | 28.5 |
| BCG Tice | 31 | 19.5 |
| Unvaccinated/Unchallenged Control | 15 | 9 |

Results are displayed as the percent of cells comprising the lymphocyte gate. Two mice were evaluated in each group and the mean of the two values are displayed.

TABLE 6

T-lymphocyte populations in lungs harvested from mice vaccinated with BCG Tice versus different amounts of BVV at 14 weeks post-challenge, 23 weeks post-vaccination

| Vaccination Group | Vaccination Dose | Log No. of bacilli in lung at 24 h post-vaccination | CD4% | CD8% |
|---|---|---|---|---|
| H37Rv(pLUC10-AS-SOD) | $5 \times 10^5$ cfu | 2.7 | 41.3 | 17 |
| H37Rv(pHV203-AS-SOD) | $5 \times 10^6$ cfu | 3.8 | 62 | 17.3 |
| H37Rv(pHV203-AS-SOD) | $5 \times 10^5$ cfu | 2.6 | 46 | 15.2 |
| H37Rv(pHV203-AS-SOD) | $5 \times 10^4$ cfu | 1.5 | 48.8 | 10.8 |
| BCG Tice | $5 \times 10^5$ cfu | 2.5 | 38.5 | 12.5 |
| Unvaccinated/Erdman challenged | None | None | 39 | 13.3 |
| Unvaccinated/Unchallenged | None | None | 29.8 | 8.5 |

T-cell results are displayed as the percent of cells comprising the lymphocyte gate. Two mice were evaluated in each group and the mean of the two values are displayed.

TABLE 7

Monocyte and Granulocyte populations in lungs harvested from mice vaccinated with BVV versus control strains at 67 hours post-vaccination

| Vaccination Group | Monocyte % | Granulocyte % |
|---|---|---|
| H37Rv(pLUC10-AS-SOD) | 40 | 26 |
| BCG Tice | 32.5 | 30 |
| H37Rv | 18 | 41.5 |
| Unvaccinated | 19 | 72 |

Results are displayed as the percent of cells expressing F4/80 antigens in the monocyte gate and the percent of cells expressing Ly6 antigens in the granulocyte gate. Two mice were evaluated in each study group and the mean of the two values are displayed. Results from a single mouse are shown for the unvaccinated group.

TABLE 8

Lymphocyte populations in lungs harvested from mice vaccinated with BVV versus control strains at 67 hours post-vaccination

| 8a. Vaccination Group | B220% | CD3% |
|---|---|---|
| H37Rv(pLUC10-AS-SOD) | 45.5 | 20.5 |
| BCG Tice | 44.5 | 17.5 |
| H37Rv | 54.5 | 19 |
| Unvaccinated | 48 | 8 |

| 8b. Vaccination Group | CD4% | CD8% | NK1.1% |
|---|---|---|---|
| H37Rv(pLUC10-AS-SOD) | 26 | 5 | 21 |
| BCG Tice | 27 | 6 | 16 |
| H37Rv | 26 | 5 | 27 |

Results are displayed as the percent of cells comprising the lymphocyte gate. Subtables 8a and 8b represent FACS involving different samples. For B220 cells and CD3+ cells, two mice were evaluated in each study group and the mean of the two values are displayed, except for the unvaccinated group which involved a single mouse. CD4%, CD8%, and NK1.1% values are determined from a single mouse in each group.

TABLE 9

Dendritic cells and their activation status in lungs harvested from mice vaccinated with H37Rv versus BVV at 20 hours post-vaccination

| | CD11c+/CD80+ | CD11c+/Class I-A/Dual + |
|---|---|---|
| H37Rv #1 | 9.36 | 10.4 |
| H37Rv #2 | 8.65 | 13.3 |
| BVV #1 | 21.0 | 18.1 |
| BVV #2 | 21.0 | 17.8 |

Results are displayed as the percent of cells comprising a dendritic cell gate.

TABLE 10

T-lymphocyte populations in lungs harvested from mice vaccinated with BCG Tice versus BCG(pHV203-AS-SOD) at one month post-vaccination

| Vaccination Group | CD4% | CD8% |
|---|---|---|
| H37Rv | 34.4 | 28.3 |
| BCG | 48.7 | 24.0 |
| BCG(pHV203-AS-SOD) | 38.9 | 39.3 |
| Unvaccinated/Unchallenged Control | 17 | 10.3 |

Results are displayed as the percent of cells comprising the lymphocyte gate. Mean values from two mice in the H37Rv and BCG groups, and absolute values from a single mouse in the BCG(pHV203-AS-SOD) and Unvaccinated groups are displayed.

TABLE 11

Mutants of *M. tuberculosis* SOD

| SOD mutant[1] | Rationale for alteration[2] | Doubling time[3] | % Growth rate[4] |
|---|---|---|---|
| Wild-type enzyme | | 155 min | 100% |
| No enzyme | | No growth | 0% |
| E54 deleted | In 6 AA domain linker between a1 & a2 | 4,725 min | 3% |
| G88 deleted | In 10 AA domain linker between a2 & a3 | 430 min | 36% |
| G87&G88 deleted | In 10 AA domain linker between a2 & a3 | 500 min | 31% |
| G134 deleted | In 4 AA domain linker between β1 & β2 | 1,240 min | 13% |
| P150 deleted | In the 144-152 domain linker between β2 & β3 that is implicated in dimer formation | 1,700 min | 9% |
| V184 deleted | In 3 AA domain linker between a5 & a6 | 980 min | 16% |

TABLE 11-continued

Mutants of *M. tuberculosis* SOD

| SOD mutant[1] | Rationale for alteration[2] | Doubling time[3] | % Growth rate[4] |
|---|---|---|---|
| H28K substitution | cac to aag; H28 binds to the catalytic iron | 13,000 min | 1% |
| H76K substitution | cac to aag; H76 binds to the catalytic iron | 1,080 min | 14% |
| H145K substitution | cac to aag; H145 interacts with hydroxide ion that binds to the catalytic iron | 910 min | 17% |
| H164K substitution | cac to aag; H164 binds to the catalytic iron | 965 min | 16% |

[1]Refers to the SOD enzyme transformed into the SOD-negative *E. coli* strain CK9C1891. Amino acid numbering per Jackson and Cooper (Jackson and Cooper, 1998), see FIG. 21 to identify amino acid position relative to important structural features of *M. tuberculosis* SOD as well as proximity to the Fe3+ cofactor.

[2]Position and functional significance per Cooper et al. (Cooper, McIntyre, Badasso, Wood, Zhang, Garbe, and Young, 1995) and Bunting et al. (Bunting, Cooper, Badasso, Tickle, Newton, Wood, Zhang, and Young, 1998); AA = amino acid

[3]To obtain more precise comparisons of relative growth rates, M9 minimal media was inoculated with each strain to yield an initial A600 value of 0.05 and incubated at 37° C. with agitation. A600 values were monitored hourly for 8 hours, and doubling times determined by plotting A600 versus minutes as shown in FIG. 22.

[4]Growth of the transformant containing the mutant *M. tuberculosis* sodA gene as a percent of the growth rate of the *E. coli* transformant containing the wild-type *M. tuberculosis* sodA gene, based on doubling times.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein.

What is claimed is:

1. A method of modifying a bacterium to enhance the immunogenicity of the bacterium, comprising reducing the activity of an anti-apoptotic enzyme produced by the bacterium, wherein the bacterium is an intracellular bacterium selected from the group consisting of an *M. tuberculosis* strain or an *M. bovis* strain, and wherein the enzyme is selected from the group consisting of iron-manganese superoxide dismutase, thioredoxin-like protein superfamily, thioredoxin reductase-like protein superfamily, glutathione reductase-like protein superfamily, glutamine synthetase, thiol reductases, and protein disulphide oxidoreductases, whereby the bacterium has enhanced immunogenicity in a subject, wherein the reduced activity level of the anti-apoptotic enzyme is 15% or less of normal levels.

2. The method of claim 1, wherein the reduced activity level of the anti-apoptotic enzyme is 3% or less of normal levels.

3. The method of claim 1, wherein the enzyme activity is reduced, but is still present.

4. A modified bacterium produced with the method of claim 1.

5. The modified bacterium of claim 4, wherein the bacterium is attenuated.

6. An immunogenic composition comprising the modified bacterium of claim 4.

7. A method of producing an immune response in a subject, comprising administering to the subject an effective amount of the composition of claim 6.

8. The method of claim 7, wherein the subject is a mammal.

9. The method of claim 8, wherein the mammal is human.

10. The method of claim 1, wherein the strain of *M. bovis* is BCG.

11. A modified intracellular bacterium having been modified to reduce the activity of an anti-apoptotic enzyme produced by the bacterium, wherein the bacterium is an intracellular bacterium selected from the group consisting of an *M. tuberculosis* strain or an *M. bovis* strain, and wherein the enzyme is selected from the group consisting of iron-manganese superoxide dismutase, thioredoxin-like protein superfamily, thioredoxin reductase-like protein superfamily, glutathione reductase-like protein superfamily, glutamine synthetase, thiol reductases, and protein disulphide oxidoreductases, whereby the bacterium has enhanced immunogenicity in a subject, wherein the reduced activity level of the anti-apoptotic enzyme is 15% or less of normal levels.

12. The method of claim 11, wherein the reduced activity level of the anti-apoptotic enzyme is 3% or less of normal levels.

13. The method of claim 11, wherein the enzyme activity is reduced, but is still present.

14. The method of claim 11, wherein the strain of *M. bovis* is BCG.

15. A method of modifying a bacterium to enhance the immunogenicity of the bacterium, comprising reducing the activity of an anti-apoptotic enzyme produced by the bacterium, wherein the bacterium is *M. avium*, and wherein the enzyme is selected from the group consisting of iron-manganese superoxide dismutase, thioredoxin-like protein superfamily, thioredoxin reductase-like protein superfamily, glutathione reductase-like protein superfamily, glutamine synthetase, thiol reductases, and protein disulphide oxidoreductases, whereby the bacterium has enhanced immunogenicity in a subject, wherein the reduced activity level of the anti-apoptotic enzyme is 15% or less of normal levels.

16. A modified intracellular bacterium having been modified to reduce the activity of an anti-apoptotic enzyme produced by the bacterium, wherein the bacterium is *M. avium*, or an *M. bovis* strain, and wherein the enzyme is selected from the group consisting of iron-manganese superoxide dismutase, thioredoxin-like protein superfamily, thioredoxin reductase-like protein superfamily, glutathione reductase-like protein superfamily, glutamine synthetase, thiol reductases, and protein disulphide oxidoreductases, whereby the bacterium has enhanced immunogenicity in a subject, wherein the reduced activity level of the anti-apoptotic enzyme is 15% or less of normal levels.

* * * * *

UNITED STATES PATENT AND TRADEMARK OFFICE
CERTIFICATE OF CORRECTION

PATENT NO. : 8,481,056 B2
APPLICATION NO. : 13/236325
DATED : July 9, 2013
INVENTOR(S) : Douglas S. Kernodle and Markian R. Bochan Page 1 of 1

It is certified that error appears in the above-identified patent and that said Letters Patent is hereby corrected as shown below:

In the Specification

In column 1, lines 14-17, please amend the specification as follows:

-- This invention was made with government support under NIH Grant AI035250, NIH Grant AI051561, NIH Grant AI057157, NIH Grant AI037871, and a Merit Review Award from the Department of Veterans Affairs. The government has certain rights in the invention. --

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1
aggcggccgc tcgaacgagg ggcgtgaccg 30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
cagtctagag acgggcctct tcgtcgtacg 30

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
cagatcgata cgcgtgctag cattccaggt ttacgaccac c 41

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

```
<400> SEQUENCE: 4
cagactagta tcggcccagt tcacgacgtt                                    30
```